United States Patent
Simpson et al.

(10) Patent No.: US 9,788,766 B2
(45) Date of Patent: Oct. 17, 2017

(54) ANALYTE SENSING BIOINTERFACE

(71) Applicant: DexCom, Inc., San Diego, CA (US)

(72) Inventors: Peter C. Simpson, Cardiff, CA (US); James H. Brauker, Addison, MI (US)

(73) Assignee: DexCom, Inc., San Diego, CA (US)

(*) Notice: Subject to any disclaimer, the term of this patent is extended or adjusted under 35 U.S.C. 154(b) by 708 days.

(21) Appl. No.: 14/281,697

(22) Filed: May 19, 2014

(65) Prior Publication Data

US 2014/0303465 A1    Oct. 9, 2014

Related U.S. Application Data

(63) Continuation of application No. 13/285,880, filed on Oct. 31, 2011, now abandoned, which is a continuation of application No. 11/404,929, filed on Apr. 14, 2006, now Pat. No. 8,060,174.

(60) Provisional application No. 60/671,622, filed on Apr. 15, 2005, provisional application No. 60/683,923, filed on May 23, 2005.

(51) Int. Cl.
| | | |
|---|---|---|
| *A61B 5/05* | (2006.01) | |
| *A61B 5/145* | (2006.01) | |
| *A61B 5/1486* | (2006.01) | |
| *C12Q 1/00* | (2006.01) | |
| *B33Y 80/00* | (2015.01) | |
| *A61B 5/00* | (2006.01) | |

(52) U.S. Cl.
CPC ........ *A61B 5/14532* (2013.01); *A61B 5/1486* (2013.01); *A61B 5/14865* (2013.01); *C12Q 1/001* (2013.01); *C12Q 1/006* (2013.01); *A61B 5/0031* (2013.01); *B33Y 80/00* (2014.12)

(58) Field of Classification Search
CPC ............. A61B 5/14532; A61B 5/1486; A61B 5/14865
See application file for complete search history.

(56) References Cited

U.S. PATENT DOCUMENTS

| | | |
|---|---|---|
| 3,775,182 A | 11/1973 | Patton et al. |
| 3,898,984 A | 8/1975 | Mandel et al. |
| 3,943,918 A | 3/1976 | Lewis |

(Continued)

FOREIGN PATENT DOCUMENTS

| | | |
|---|---|---|
| EP | 0 098 592 | 1/1984 |
| EP | 0 127 958 | 12/1984 |

(Continued)

OTHER PUBLICATIONS

Aalders et al. 1991. Development of a wearable glucose sensor; studies in healthy volunteers and in diabetic patients. The International Journal of Artificial Organs 14(2): 102-108.

(Continued)

*Primary Examiner* — Christian Jang
(74) *Attorney, Agent, or Firm* — Knobbe Martens Olson & Bear, LLP

(57) ABSTRACT

Disclosed herein is an analyte sensing biointerface that comprises a sensing electrode incorporated within a non-conductive matrix comprising a plurality of passageways extending through the matrix to the sensing electrode. Also disclosed herein are methods of manufacturing a sensing biointerface and methods of detecting an analyte within tissue of a host using an analyte sensing biointerface.

5 Claims, 17 Drawing Sheets

(56) References Cited

U.S. PATENT DOCUMENTS

| | | | |
|---|---|---|---|
| 4,197,840 A | 4/1980 | Beck et al. |
| 4,225,410 A | 9/1980 | Pace |
| 4,240,889 A | 12/1980 | Yoda et al. |
| 4,253,469 A | 3/1981 | Aslan |
| 4,255,500 A | 3/1981 | Hooke |
| 4,260,725 A | 4/1981 | Keogh et al. |
| 4,353,368 A | 10/1982 | Slovak et al. |
| 4,403,984 A | 9/1983 | Ash et al. |
| 4,436,094 A | 3/1984 | Cerami |
| 4,442,841 A | 4/1984 | Uehara et al. |
| 4,477,314 A | 10/1984 | Richter et al. |
| 4,494,950 A | 1/1985 | Fischell |
| RE31,916 E | 6/1985 | Oswin et al. |
| 4,554,927 A | 11/1985 | Fussell |
| 4,571,292 A | 2/1986 | Liu et al. |
| 4,603,152 A | 7/1986 | Laurin et al. |
| 4,680,268 A | 7/1987 | Clark, Jr. |
| 4,703,756 A | 11/1987 | Gough et al. |
| 4,721,677 A | 1/1988 | Clark, Jr. |
| 4,731,726 A | 3/1988 | Allen |
| 4,757,022 A | 7/1988 | Shults et al. |
| 4,805,624 A | 2/1989 | Yao et al. |
| 4,805,625 A | 2/1989 | Wyler |
| 4,813,424 A | 3/1989 | Wilkins |
| 4,852,573 A | 8/1989 | Kennedy |
| 4,883,057 A | 11/1989 | Broderick |
| 4,927,407 A | 5/1990 | Dorman |
| 4,953,552 A | 9/1990 | DeMarzo |
| 4,970,145 A | 11/1990 | Bennetto et al. |
| 4,986,271 A | 1/1991 | Wilkins |
| 4,988,341 A | 1/1991 | Columbus et al. |
| 5,019,096 A | 5/1991 | Fox, Jr. et al. |
| 5,050,612 A | 9/1991 | Matsumura |
| 5,108,819 A | 4/1992 | Heller et al. |
| 5,127,405 A | 7/1992 | Alcala et al. |
| 5,130,231 A | 7/1992 | Kennedy et al. |
| 5,137,028 A | 8/1992 | Nishimura |
| 5,160,418 A | 11/1992 | Mullen |
| 5,165,407 A | 11/1992 | Wilson et al. |
| 5,171,689 A | 12/1992 | Kawaguri et al. |
| 5,190,041 A | 3/1993 | Palti |
| 5,222,980 A | 6/1993 | Gealow |
| 5,249,576 A | 10/1993 | Golberger et al. |
| 5,264,104 A | 11/1993 | Gregg et al. |
| 5,269,891 A | 12/1993 | Colin |
| 5,282,848 A | 2/1994 | Schmitt |
| 5,299,571 A | 4/1994 | Mastrototaro |
| 5,316,008 A | 5/1994 | Suga et al. |
| 5,322,063 A | 6/1994 | Allen et al. |
| 5,324,322 A | 6/1994 | Grill et al. |
| 5,328,451 A | 7/1994 | Davis et al. |
| 5,331,555 A | 7/1994 | Hashimoto et al. |
| 5,368,028 A | 11/1994 | Palti |
| 5,372,133 A | 12/1994 | Hogen Esch |
| 5,382,514 A | 1/1995 | Passaniti et al. |
| 5,384,028 A | 1/1995 | Ito |
| 5,387,327 A | 2/1995 | Khan |
| 5,390,671 A | 2/1995 | Lord et al. |
| 5,391,250 A | 2/1995 | Cheney, II et al. |
| 5,422,246 A * | 6/1995 | Koopal | A61L 31/10 204/403.1 |
| 5,428,123 A | 6/1995 | Ward et al. |
| 5,429,735 A | 7/1995 | Johnson et al. |
| 5,431,160 A | 7/1995 | Wilkins |
| 5,458,631 A | 10/1995 | Xavier et al. |
| 5,462,051 A | 10/1995 | Oka et al. |
| 5,464,013 A | 11/1995 | Lemelson |
| 5,466,356 A | 11/1995 | Schneider et al. |
| 5,480,711 A | 1/1996 | Ruefer |
| 5,494,562 A | 2/1996 | Maley et al. |
| 5,497,772 A | 3/1996 | Schulman et al. |
| 5,507,288 A | 4/1996 | Bocker et al. |
| 5,513,636 A | 5/1996 | Palti |
| 5,518,601 A | 5/1996 | Foos et al. |
| 5,529,066 A | 6/1996 | Palti |
| 5,531,878 A | 7/1996 | Vadgama et al. |
| 5,564,439 A | 10/1996 | Picha |
| 5,568,806 A | 10/1996 | Cheney, II et al. |
| 5,569,186 A | 10/1996 | Lord et al. |
| 5,569,462 A | 10/1996 | Martinson et al. |
| 5,571,395 A | 11/1996 | Park et al. |
| 5,582,184 A | 12/1996 | Ericson et al. |
| 5,584,813 A | 12/1996 | Livingston et al. |
| 5,584,876 A | 12/1996 | Bruchman et al. |
| 5,586,553 A | 12/1996 | Halili et al. |
| 5,589,133 A | 12/1996 | Suzuki |
| 5,624,537 A | 4/1997 | Turner et al. |
| 5,628,890 A | 5/1997 | Carter et al. |
| 5,640,954 A | 6/1997 | Pfeiffer |
| 5,681,572 A | 10/1997 | Seare |
| 5,683,562 A | 11/1997 | Schaffar et al. |
| 5,695,623 A | 12/1997 | Michel et al. |
| 5,704,354 A | 1/1998 | Priedel et al. |
| 5,706,807 A | 1/1998 | Picha |
| 5,711,861 A | 1/1998 | Ward et al. |
| 5,741,330 A | 4/1998 | Brauker et al. |
| 5,743,262 A | 4/1998 | Lepper, Jr. et al. |
| 5,749,832 A | 5/1998 | Vadgama et al. |
| 5,756,632 A | 5/1998 | Ward et al. |
| 5,773,270 A | 6/1998 | D'Orazio et al. |
| 5,776,324 A | 7/1998 | Usala |
| 5,791,344 A | 8/1998 | Schulman et al. |
| 5,800,420 A | 9/1998 | Gross |
| 5,804,048 A | 9/1998 | Wong et al. |
| 5,807,375 A | 9/1998 | Gross et al. |
| 5,820,622 A | 10/1998 | Gross et al. |
| 5,833,603 A | 11/1998 | Kovacs et al. |
| 5,837,728 A | 11/1998 | Purcell |
| 5,858,365 A | 1/1999 | Feller |
| 5,863,400 A | 1/1999 | Drummond et al. |
| 5,882,494 A | 3/1999 | Van Antwerp |
| 5,914,026 A | 6/1999 | Blubaugh, Jr. et al. |
| 5,931,814 A | 8/1999 | Alex et al. |
| 5,944,661 A | 8/1999 | Swette et al. |
| 5,957,854 A | 9/1999 | Besson et al. |
| 5,961,451 A | 10/1999 | Reber et al. |
| 5,964,804 A | 10/1999 | Brauker et al. |
| 5,964,993 A | 10/1999 | Blubaugh et al. |
| 5,967,986 A | 10/1999 | Cimochowski et al. |
| 5,972,199 A | 10/1999 | Heller |
| 5,985,129 A | 11/1999 | Gough et al. |
| 6,001,067 A | 12/1999 | Shults et al. |
| 6,011,984 A | 1/2000 | Van Antwerp et al. |
| 6,049,727 A | 4/2000 | Crothall |
| 6,051,389 A | 4/2000 | Ahl et al. |
| 6,059,946 A | 5/2000 | Yukawa et al. |
| 6,066,083 A | 5/2000 | Slater et al. |
| 6,091,975 A | 7/2000 | Daddona et al. |
| 6,093,172 A | 7/2000 | Funderburk et al. |
| 6,117,290 A | 9/2000 | Say |
| 6,119,028 A | 9/2000 | Schulman et al. |
| 6,122,536 A | 9/2000 | Sun et al. |
| 6,134,461 A | 10/2000 | Say et al. |
| 6,144,871 A | 11/2000 | Saito et al. |
| 6,175,752 B1 | 1/2001 | Say et al. |
| 6,212,416 B1 | 4/2001 | Ward et al. |
| 6,233,471 B1 | 5/2001 | Berner et al. |
| 6,268,161 B1 | 7/2001 | Han et al. |
| 6,275,717 B1 | 8/2001 | Gross et al. |
| 6,285,897 B1 | 9/2001 | Kilcoyne et al. |
| 6,296,615 B1 | 10/2001 | Brockway et al. |
| 6,330,464 B1 | 12/2001 | Colvin, Jr. et al. |
| 6,343,225 B1 | 1/2002 | Clark, Jr. |
| 6,366,794 B1 | 4/2002 | Moussy et al. |
| 6,368,274 B1 | 4/2002 | Van Antwerp et al. |
| 6,400,974 B1 | 6/2002 | Lesho |
| 6,406,066 B1 | 6/2002 | Uegane |
| 6,409,674 B1 | 6/2002 | Brockway et al. |
| 6,424,847 B1 | 7/2002 | Mastrototaro et al. |
| 6,442,413 B1 | 8/2002 | Silver |
| 6,447,448 B1 | 9/2002 | Ishikawa et al. |
| 6,454,710 B1 | 9/2002 | Ballerstadt et al. |
| 6,466,810 B1 | 10/2002 | Ward et al. |
| 6,484,046 B1 | 11/2002 | Say et al. |

(56) References Cited

U.S. PATENT DOCUMENTS

| | | |
|---|---|---|
| 6,497,729 B1 | 12/2002 | Moussy et al. |
| 6,517,508 B1 | 2/2003 | Utterberg et al. |
| 6,528,584 B2 | 3/2003 | Kennedy et al. |
| 6,546,268 B1 | 4/2003 | Ishikawa et al. |
| 6,565,509 B1 | 5/2003 | Say et al. |
| 6,587,705 B1 | 7/2003 | Kim et al. |
| 6,591,125 B1 | 7/2003 | Buse et al. |
| 6,618,934 B1 | 9/2003 | Feldman et al. |
| 6,666,821 B2 | 12/2003 | Keimel |
| 6,702,857 B2 | 3/2004 | Brauker et al. |
| 6,702,972 B1 | 3/2004 | Markle |
| 6,721,587 B2 | 4/2004 | Gough |
| 6,741,877 B1 | 5/2004 | Shults et al. |
| 6,773,565 B2 | 8/2004 | Kunimoto et al. |
| 6,793,632 B2 | 9/2004 | Sohrab |
| 6,793,802 B2 | 9/2004 | Lee et al. |
| 6,804,544 B2 | 10/2004 | van Antwerp et al. |
| 6,862,465 B2 | 3/2005 | Shults et al. |
| 6,895,263 B2 | 5/2005 | Shin et al. |
| 6,936,006 B2 | 8/2005 | Sabra |
| 6,952,604 B2 | 10/2005 | DeNuzzio et al. |
| 6,965,791 B1 | 11/2005 | Hitchcock et al. |
| 6,991,643 B2 | 1/2006 | Saadat |
| 7,058,437 B2 | 6/2006 | Buse et al. |
| 7,081,195 B2 | 7/2006 | Simpson et al. |
| 7,110,803 B2 | 9/2006 | Shults et al. |
| 7,134,999 B2 | 11/2006 | Brauker et al. |
| 7,136,689 B2 | 11/2006 | Shults et al. |
| 7,153,265 B2 | 12/2006 | Vachon |
| 7,166,074 B2 | 1/2007 | Reghabi et al. |
| 7,169,289 B2 | 1/2007 | Schulein et al. |
| 7,192,450 B2 | 3/2007 | Brauker et al. |
| 7,225,535 B2 | 6/2007 | Feldman et al. |
| 7,329,239 B2 | 2/2008 | Safabash et al. |
| 7,344,499 B1 | 3/2008 | Prausnitz et al. |
| 7,364,592 B2 | 4/2008 | Carr-Brendel et al. |
| 7,417,164 B2 | 8/2008 | Suri |
| 7,426,408 B2 | 9/2008 | DeNuzzio et al. |
| 7,632,228 B2 | 12/2009 | Brauker et al. |
| 7,657,297 B2 | 2/2010 | Simpson et al. |
| 8,060,174 B2 | 11/2011 | Simpson et al. |
| 2001/0044413 A1 | 11/2001 | Pierce et al. |
| 2001/0053933 A1 | 12/2001 | Phaneuf et al. |
| 2002/0019330 A1 | 2/2002 | Murray et al. |
| 2002/0055673 A1 | 5/2002 | Van Antwerp et al. |
| 2002/0128546 A1 | 9/2002 | Silver |
| 2002/0151816 A1 | 10/2002 | Rich et al. |
| 2002/0169369 A1 | 11/2002 | Ward et al. |
| 2002/0185384 A1 | 12/2002 | Leong et al. |
| 2002/0188185 A1 | 12/2002 | Sohrab |
| 2003/0023317 A1 | 1/2003 | Brauker et al. |
| 2003/0032874 A1 | 2/2003 | Rhodes et al. |
| 2003/0059631 A1 | 3/2003 | Al-Lamee |
| 2003/0065254 A1 | 4/2003 | Schulman et al. |
| 2003/0070548 A1 | 4/2003 | Clausen |
| 2003/0125613 A1 | 7/2003 | Enegren et al. |
| 2003/0130616 A1 | 7/2003 | Steil et al. |
| 2003/0181794 A1 | 9/2003 | Rini et al. |
| 2003/0199745 A1 | 10/2003 | Burson et al. |
| 2003/0211625 A1 | 11/2003 | Cohan |
| 2003/0225361 A1 | 12/2003 | Sabra |
| 2003/0235817 A1 | 12/2003 | Bartkowiak et al. |
| 2004/0015063 A1 | 1/2004 | DeNuzzio et al. |
| 2004/0087671 A1 | 5/2004 | Tamada et al. |
| 2004/0106857 A1 | 6/2004 | Gough |
| 2004/0186362 A1 | 9/2004 | Brauker et al. |
| 2005/0008671 A1 | 1/2005 | Van Antwerp |
| 2005/0031689 A1 | 2/2005 | Shults et al. |
| 2005/0033132 A1* | 2/2005 | Shults ............... A61B 5/14532 600/347 |
| 2005/0059871 A1 | 3/2005 | Gough et al. |
| 2005/0096519 A1 | 5/2005 | DeNuzzio et al. |
| 2005/0121322 A1 | 6/2005 | Say |
| 2005/0211571 A1 | 9/2005 | Schulein et al. |
| 2005/0242479 A1 | 11/2005 | Petisce et al. |
| 2005/0245795 A1 | 11/2005 | Goode et al. |
| 2005/0245799 A1 | 11/2005 | Brauker et al. |
| 2005/0251083 A1 | 11/2005 | Carr-Brendel et al. |
| 2005/0272989 A1 | 12/2005 | Shah et al. |
| 2006/0016700 A1 | 1/2006 | Brister et al. |
| 2006/0036140 A1 | 2/2006 | Brister et al. |
| 2006/0198864 A1 | 9/2006 | Shults et al. |
| 2006/0200022 A1 | 9/2006 | Brauker et al. |
| 2006/0204536 A1 | 9/2006 | Shults et al. |
| 2006/0211921 A1 | 9/2006 | Brauker et al. |
| 2006/0224108 A1 | 10/2006 | Brauker et al. |
| 2006/0257995 A1 | 11/2006 | Simpson et al. |
| 2006/0257996 A1 | 11/2006 | Simpson et al. |
| 2006/0263763 A1 | 11/2006 | Simpson et al. |
| 2006/0270922 A1 | 11/2006 | Brauker et al. |
| 2006/0270923 A1 | 11/2006 | Brauker et al. |
| 2006/0281985 A1 | 12/2006 | Ward et al. |
| 2007/0027370 A1 | 2/2007 | Brauker et al. |
| 2007/0032718 A1 | 2/2007 | Shults et al. |
| 2007/0045902 A1 | 3/2007 | Brauker et al. |
| 2007/0088208 A1* | 4/2007 | Yasuzawa ............ A61N 1/05 600/345 |
| 2007/0173711 A1* | 7/2007 | Shah ............... A61B 5/14532 600/347 |
| 2007/0235331 A1 | 10/2007 | Simpson et al. |
| 2008/0045824 A1 | 2/2008 | Tapsak et al. |
| 2008/0187655 A1 | 8/2008 | Markle et al. |
| 2008/0188722 A1 | 8/2008 | Markle et al. |
| 2008/0188725 A1 | 8/2008 | Markle et al. |
| 2008/0228051 A1 | 9/2008 | Shults et al. |
| 2008/0228054 A1 | 9/2008 | Shults et al. |
| 2008/0242961 A1 | 10/2008 | Brister et al. |
| 2008/0305009 A1 | 12/2008 | Gamsey et al. |
| 2008/0305506 A1 | 12/2008 | Suri |
| 2009/0018418 A1 | 1/2009 | Markle et al. |
| 2009/0018426 A1 | 1/2009 | Markle et al. |
| 2009/0036763 A1 | 2/2009 | Brauker et al. |
| 2009/0061528 A1 | 3/2009 | Suri |
| 2009/0062633 A1 | 3/2009 | Brauker et al. |
| 2009/0081803 A1 | 3/2009 | Gamsey et al. |
| 2009/0177143 A1 | 7/2009 | Markle et al. |
| 2009/0264719 A1 | 10/2009 | Markle et al. |
| 2010/0087724 A1 | 4/2010 | Brauker et al. |
| 2010/0160760 A1 | 6/2010 | Shults et al. |

FOREIGN PATENT DOCUMENTS

| | | |
|---|---|---|
| EP | 0 320 109 | 6/1989 |
| EP | 0 353 328 | 2/1990 |
| EP | 0 390 390 | 10/1990 |
| EP | 0 534 074 | 3/1993 |
| EP | 0 563 795 | 10/1993 |
| FR | 2656423 | 6/1991 |
| FR | 2760962 | 9/1998 |
| GB | 2149918 | 6/1985 |
| WO | WO 89/02720 | 4/1989 |
| WO | WO 92/07525 | 5/1992 |
| WO | WO 92/13271 | 8/1992 |
| WO | WO 93/14693 | 8/1993 |
| WO | WO 96/14026 | 5/1996 |
| WO | WO 96/25089 | 8/1996 |
| WO | WO 97/01986 | 1/1997 |
| WO | WO 97/43633 | 11/1997 |
| WO | WO 98/24358 | 6/1998 |
| WO | WO 99/56613 | 4/1999 |
| WO | WO 00/13003 | 3/2000 |
| WO | WO 00/19887 | 4/2000 |
| WO | WO 00/32098 | 6/2000 |
| WO | WO 00/33065 | 6/2000 |
| WO | WO 00/74753 | 12/2000 |
| WO | WO 01/12158 | 2/2001 |
| WO | WO 01/43660 | 6/2001 |
| WO | WO 2006/122553 | 11/2006 |

OTHER PUBLICATIONS

Abe et al. 1992. Characterization of glucose microsensors for intracellular measurements. Analytical Chemistry 64(18):2160-2163.

(56) References Cited

OTHER PUBLICATIONS

Abel et al. 1984. Experience with an implantable glucose sensor as a prerequisite of an artificial beta cell Biomedica et Biochimica Acta 43(5):577-584.

Abel et al, 2002. Biosensors for in vivo glucose measurement: can we cross the experimental stage. Biosensors & Bioelectronics 17:1059-1070.

Alcock & Turner, 1994. Continuous Analyte Monitoring to Aid Clinical Practice. IEEE Engineering in Medicine & Biology 13:319-325.

American Heritage Dictionary 4th Edition. 2000. Houghton Mifflin, Company p. 82.

Amin et al. 2003. Hypoglycemia prevalence in prepubertal children with type 1 diabetes on standard insulin regimen: Use of continuous glucose monitoring system. Diabetes Care 26(3):662-667.

Answers.com. "xenogenic," The American Heritage Stedman's Medical Dictionary. Houghton Mifflin Company 2002. Answers. com Nov. 7, 2006 http://www. Answers.com/topic/xenogenic.

Armour et al. Dec. 1990. Application of Chronic Intravascular Blood Glucose Sensor in Dogs. Diabetes 39:1519-1526.

Asberg et al. 2003. Hydrogels of a Conducting Conjugated Polymer as 3-D Enzyme Electrode. Biosensors &Bioelectronics pp. 199-207.

Atanasov et al. 1994. Biosensor for continuous glucose monitoring. Biotechnology and Bioengineering 43:262-266.

Atanasov et al. 1997. Implantation of a refillable glucose monitoring-telemetry device. Biosensors & Bioelectronics 12:669-680.

Aussedat et al. 1997. A user-friendly method for calibrating a subcutaneous glucose sensor-based hypoglycaemic alarm. Biosensors & Bioelectronics 12(11): 1061-1071.

Bailey et al. 2007. Reduction in hemoglobin A1c with real-time continuous glucose monitoring: results from a 12-week observational study. Diabetes Technology & Therapeutics 9(3):203-210.

Beach et al. 1999. Subminiature implantable potentiostat and modified commercial telemetry device for remote glucose monitoring. IEEE Transactions on Instrumentation and Measurement 48(6):1239-1245.

Bellucci et al. Jan. 1986. Electrochemical behaviour of graphite-epoxy composite materials (GECM) in aqueous salt solutions. Journal of Applied Electrochemistry 16(1):15-22.

Bessman et al. 1973. Progress toward a glucose sensor for the artificial pancreas Proceedings of a Workshop on Ion-Selective Microelectrodes Jun. 4-5, 1973, Boston MA 189-197.

Biermann et al. 2008. How would patients behave if they were continually informed of their blood glucose levels? A simulation study using a "virtual" patient. Diabetes Technology & Therapeutics 10:178-187.

Bindra et al. 1989. Pulsed amperometric detection of glucose in biological fluids at a surface-modified gold electrode. Analytical Chemist 61:2566-2570.

Bindra et al. 1991. Design and In Vitro Studies of a Needle-Type Glucose Senso for Subcutaneous Monitoring. Analytical Chemistry 63:1692-96.

Bisenberger et al. 1995. A triple-step potential waveform at enzyme multisensors with thick-film gold electrodes for detection of glucose and sucrose. Sensors and Actuators B 28:181-189.

Bland et al. 1990. A note on the use of the intraclass correlation coefficient in the evaluation of agreement between two methods of measurement. Computing in Biologicai Medicine 20(5):337-340.

Bobbioni-Harsch et al. 1993. Lifespan of subcutaneous glucose sensors and their performances during dynamic glycaemia changes in rats. Journal of Biomedical Engineering 15:457-463.

Bode B. W. 2000. Clinical utility of the continuous glucose monitoring system. Diabetes Technology & Therarpeutics 2 (Suppl 1):S35-41.

Bode et al. 1999. Continuous glucose monitoring used to adjust diabetes therapy improves glycosylated hemoglobin: A pilot study. Diabetes Research and Clinical Practice 46:183-190.

Bode et al. 2000. Using the continuous glucose monitoring system to improve the management of type 1 diabetes. Diabetes Technology & Therapeutics 2(Suppl 1):S43-48.

Boedeker Plastics Inc. 2009. Polyethylene Specifications Data Sheet http://www.boedeker.com/polye_p.htm [Aug. 19, 2009 3:36:33 PM].

Boland et al. 2001. Limitations of conventional methods of self-monitoring of blood glucose. Diabetes Care 24(11):1858-1862.

Bott A. W. 1997. A Comparison of Cyclic Voltammetry and Cyclic Staircase Voltammetry. Current Separations 16(1):23-26.

Bowman L.; Meindl J. D. 1986. The packaging of implantable integrated sensors, IEEE Transactions on Biomedical Engineering BME 33(2)248-255.

Brauker et al. 1995. Neovascularization of synthetic membranes directed by membrane Microarchitecture. Journal of Biomedical Materials Research 29:1517-1524.

Brauker et al. 1998. Sustained expression of high levels of human factor IX from human cells implanted within an immunoisolation device into athymic rodents. Human Gene Therapy 9:879-888.

Brauker et al. 2001. Unraveling Mysteries at the Biointerface: Molecular Mediator of Inhibition of Blood vessel Formation in the Foreign Body Capsule Revealed. Surfacts Biomaterials 6. 1,5.

Brauker et al. Jun. 27, 1996. Local Inflammatory Response Around Diffusion Chambers Containing Xenografts. Transplantation 61(12): 1671-1677.

Braunwald 2008. Biomarkers in heart failure. N. Engl. J. Med. 358:2148-2159.

Bremer et al. 2001. Benchmark data from the literature for evaluation of new glucose sensing technologies. Diabetes Technology & Therapeutics 3(3):409-418.

Brooks et al. 1987/1988. Development of an on-line glucose sensor for fermentation monitoring. Biosensors 3:45-56.

Bruckel et al. 1989. In vivo measurement of subcutaneous glucose concentrations with an enzymatic glucose sensor and a wick method. Klin Wochenschr 67:491-495.

Brunner et al. 1998. Validation of home blood glucose meters with respect to clinical and analytical approaches. Diabetes Care 21(4):585-590.

Cai et al. 2004. A wireless remote query glucose biosensor based on a pH-sensitive polymer. Analytical Chemistry 76(4):4038-4043.

Campanella et al. 1993. Biosensor for direct determination of glucose and lactate in undiluted biological fluids. Biosensors & Bioelectronics 8:307-314.

Candas et al (1994). An adaptive plasma glucose controller based on on a nonlinear insulin/glucose model. IEEE Transactions on Biomedical Engineering 41(2):116-124.

Cass et al. 1984. Ferrocene-mediated enzyme electrodes for amperometric determination of glucose. Analytical Chemistry 36:667-71.

Cassidy et al. Apr. 1993. Novel electrochemical device for the detection of cholesterol or glucose. Analyst 118:415-418.

Cellulose Acetate Product Description Product No. 419028 Sigma-Aldrich Corp. St. Louis MO. 2005.

Chase et al. 2001. Continuous subcutaneous glucose monitoring in children with type 1 diabetes. Pediatrics 107:222-226.

Chatterjee et al. 1997. Poly(ether Urethane) and poly(ether urethane urea) membranes with high H2S/CH4 selectivity. Journal of Membrane Science 135:99-106.

Chen et al. 2006. A noninterference polypyrrole glucose biosensor. Biosensors and Bioelectronics 22:639-643.

Ciba® Irgacure 2959 Photoinitiator Product Description Ciba Specialty Chemicals Inc. Basel Switzerland.

Claremont et al. 1986. Subcutaneous implantation of a ferrocene-mediated glucose sensor in pigs. Diabetologia 29:817-821.

Claremont et al. Jul. 1986. Potentially-implantable ferrocene-mediated glucose sensor. Journal of Biomedical Engineering 8:272-274.

Clark et al. 1981. One-minute electrochemical enzymic assay for cholesterol in biological materials. Clinical Chemistry 27(12):1978-1982.

Clark et al. 1987. Configurational cyclic voltammetry: increasing the specificity and reliability of implanted electrodes IEEE/Ninth Annual Conference of the Engineering in Medicine and Biology Society pp. 0782-0783.

(56) References Cited

OTHER PUBLICATIONS

Clark et al. 1988. Long-term stability of electroenzymatic glucose sensors implanted in mice. Transactions of the American Society of Artificial Internal Organs 34:259-265.
CLSI. Performance metrics for continuous interstitial glucose monitoring; approved guideline CLSI document POCT05-A. Wayne PA; Clinical and Laboratory Standards Institute: 2008 28(33) 72 pp.
Colangelo et al. 1967. Corrosion rate measurements in vivo. Journal of Biomedical Materials Research 1:405-414.
Colowick et al. 1976. Methods in Enzymlology vol. XLIV Immobilized Enzymes. New York: Academic Press.
Cox et al. 1985. Accuracy of perceiving blood glucose in IDDM. Diabetes Care 8(6):529-536.
Csoregi et al. 1994. Design characterization and one-point in vivo calibration of a subcutaneously implanted glucose electrode. Analytical Chemistry 66(19):3131-3138.
Dai et al. 1999. Hydrogel Membranes with Mesh Size Asymmetry Based on the Gradient Crosslink of Poly(vinyl alcohol). Journal of Membrane Science 156:67-79.
Danielsson et al. 1988. Enzyme thermistors. Methods in Enzymology 137:181-197.
D'Arrigo et al. 2003. Porous-Si based bioreactors for glucose monitoring and drugs production. Proceedings of SPIE 4982:178-184.
Dassau et al. 2009. In silico evaluation platform for artifical pancreatic (3-cell development—a dynamic simulator for closed loop control with hardware-in-the-loop, Diabetes Technology & Therapeutics 11(3):1-8.
Davies et al. 1992. Polymer membranes in clinical sensor applications. I. An overview of membrane function. Biomaterials 13(14):971-978.
Davis et al. 1983. Bioelectrochemical fuel cell and sensor based on a quinoprotein alcohol dehydrogenase. Enzyme Microb. Technol. vol. 5:383-388.
Direct 30/30® Blood Glucose Sensor (Markwell Medical) Catalog © 1990 ELCO Diagnostics Company.
Dixon et al. 2002. Characterization in vitro and in vivo of the oxygen dependence of an enzyme/polymer biosensor for monitoring brain glucose. Journal of Neuroscience Methods 119:135-142.
DuPont[1] Dimension AR® (Catalog) 1998.
Durliat et al. 1976. Spectrophotometric and electrochemical determinations of L(+)-lactate in blood by use of lactate dehydrogenase from yeast. Clinical Chemistry 22(11):1802-1805.
Edwards Lifesciences 2002. Accuracy for your and your patients. Marketing materials 4 pp.
El Degheidy et al. 1986. Optimization of an implantable coated wire glucose sensor. Journal of Biomedical Engineering 8: 121-129.
El-Khatib et al. 2007. Adaptive closed-loop control provides blood-glucose regulation using dual subcutaneous insulin and glucagon infusion in diabetic swine. Journal of Diabetes Science and Technology 1(2):181-192.
El-Sa'ad et al. 1990. Moisture Absorption by Epoxy Resins: the Reverse Thermal Effect. Journal of Materials Science 25:3577-3582.
Ernst et al. 2002. Reliable glucose monitoring through the use of microsystem technology. Analytical and Bioanalytical Chemistry 373:758-761.
Fahy et al. 2008. An analysis: hyperglycemic intensive care patients need continuous glucose monitoring—easier said than done. Journal of Diabetes Science and Technology 2(2):201-204.
Fare et al. 1998. Functional characterization of a conducting polymer-based immunoassay system. Biosensors & Bioelectronics 13(3-4):459-470.
Feldman et al. 2003. A continuous glucose sensor based on wired enzyme technology—results from a 3-day trial in patients with type 1 diabetes. Diabetes Technology & Therapeutics 5(5):769-779.
Fischer et al. 1987. Assessment of subcutaneous glucose concentration: validation of the wick technique as a reference for implanted electrochemical sensors in normal and diabetic dogs. Diabetologia 30:940-945.
Fischer et al. 1989. Oxygen Tension at the Subcutaneous Implantation Site of Glucose Sensors. Biomedica et Biochimica Acta 11/12:965-972.
Fischer et al. 1995. Hypoglycaemia-warning by means of subcutaneous electrochemical glucose sensors: an animal study. Horm. Metabolism Research 27:53.
Freedman et al. 1991. Statistics Second Edition W.W. Norton & Company p. 74.
Frohnauer et al. 2001. Graphical human insulin time-activity profiles using standardized definitions. Diabetes Technology & Therapeutics 3(3):419-429.
Frost et al. 2002. Implantable chemical sensors for real-time clinical monitoring: Progress and challenges. Current Opinion in Chemical Biology 6:633-641.
Gabbay et al. 2008. Optical coherence tomography-based continuous noninvasive glucose monitoring in patients with diabetes. Diabetes Technology & Therapeutics 10:188-193.
Ganesan et al. 2005. Gold layer-based dual crosslinking procedure of glucose oxidase with ferrocene monocarboxylic acid provides a stable biosensor. Analytical Biochemistry 343:188-191.
Ganesh et al. 2008. Evaluation of the VIA® blood chemistry monitor for glucose in healthy and diabetic volunteers Journal of Diabetes Science and Technology 2(2):182-193.
Gao et al. 1989. Determination of Interfacial parameters of cellulose acetate membrane materials by HPLC. Journal of Liquid Chromatography 12(11):2083-2092.
Garg et al. 2004. Improved Glucose Excursions Using an Implantable Real-Time continuous Glucose Sensor in Adults with Type I Diabetes. Diabetes Care 27:734-738.
Geller et al. 1997. Use of an immunoisolation device for cell transplantation and tumor immunotherapy. Ann NY Academy of Science 831:438-451.
Gerritsen et al. 1999. Performance of subcutaneously implanted glucose sensors for continuous monitoring. The Netherlands Journal of Medicine 54:167-179.
Gerritsen et al. 2001. Influence of inflammatory cells and serum on the performance of implantable glucose sensors. Journal of Biomedical Materials Research 54:69-75.
Gerritsen M. 2000. Problems associated with subcutaneously implanted glucose sensors. Diabetes Care 23(2):143-145.
Gilligan et al. 1994. Evaluation of a subcutaneous glucose sensor out to 3 months in a dog model. Diabetes Care 17(8):882-887.
Gilligan et al. 2004. Feasibility of continuous long-term glucose monitoring from a subcutaneous glucose sensor in humans. Diabetes Technology & Therapeutics 6:378-386.
Godsland et al. 2001. Maximizing the Success Rate of Minimal Model Insulin Sensitivity Measurement in Humans: The Importance of Basal Glucose Levels. The Biochemical Society and the Medical Research Society 1-9.
Gouda et al. Jul. 4, 2003. Thermal inactivation of glucose oxidase. The Journal of Biological Chemistry 278(27):24324-24333.
Gough et al. 2000. Immobilized glucose oxidase in implantable glucose sensor technology. Diabetes Technology & Therapeutics 2(3):377-380.
Gough et al. 2003. Frequency characterization of blood glucose dynamics. Annals of Biomedical Engineering 31:91-97.
Gregg et al. 1990. C ross-Linked Redox Gels Contaning Glucose Oxidase for Amperometric Biosensor Applications. Analytical Chemistry 62:258-263.
Gross et al. 2000. Efficacy and reliability of the continuous glucose monitoring system. Diabetes Technology & Therapeutics 2(Suppl 1):S19-26.
Gross et al. 2000. Performance evaluation of the MiniMed® continuous glucose monitoring system during patient home use. Diabetes Technology & Therapeutics 2(1):49-56.
Guerci et al. Clinical performance of CGMS in type 1 diabetic patents treated by continuous subcutaneous insulin infusion using insulin analogs. Diabetes Care 26:582-589 2003.
Guo et al. 1998. Modification of cellulose acetate ultrafiltration membrane by gamma ray radiation, Shuichuli Jishi Bianji Weiyuanhui 23(6):315-318 (Abstract only).

(56) References Cited

OTHER PUBLICATIONS

Hall et al. 1998. Electrochemical oxidation of hydrogen peroxide at platinum electrodes. Part I: An adsorption controlled mechanism. Electrochimica Acta 43(5-6):579-588.

Hall et al. 1998. Electrochemical oxidation of hydrogen peroxide at platinum electrodes. Part II: Effect of potential. Electrochimica Acta 43(14-15):2015-2024.

Hall et al. 1999. Electrochemical oxidation of hydrogen peroxide at platinum electrodes. Part III: Effect of temperature. Electrochimica Acta 44:2455-2462.

Hall et al. 1999. Electrochemical oxidation of hydrogen peroxide at platinum electrodes. Part IV: Phosphate buffer dependence. Electrochimica Acta 44:4573-4582.

Hall et al. 2000. Electrochemical oxidation of hydrogen peroxide at platinum electrodes. Part V: Inhibition by chloride. Electrochimica Acta 45:3573-3579.

Hamilton Syringe Selection Guide. 2006. Syringe Selection www.hamiltoncompany.com.

Harrison et al. 1988. Characterization of perfluorosulfonic acid polymer coated enzyme electrodes and a miniaturized integrated potentiostat for glucose analysis in whole blood. Analytical Chemistry 60:2002-2007.

Hashiguchi et al. (1994). Development of a miniaturized glucose monitoring system by combining a needle-type glucose sensor with microdialysis sampling method: Long-term subcutaneous tissue glucose monitoring in ambulatory diabetic patients. Diabetes Care 17(5):387-396.

Heller 1990. Electrical wiring of redox enzymes. Acc. Chem. Res. 23:128-134 (1990).

Heller A. 1992. Electrical Connection of Enzyme Redox Centers to Electrodes. Journal of Physical Chemistry 96:3579-3587.

Heller A. 1999. Implanted electrochemical glucose sensors for the management of diabetes. Annual Review of Biomedical Engineering 1:153-175.

Heller A. 2003. Plugging metal connectors into enzymes. Nature Biotechnology 21:631-2.

Hicks 1985. In Situ Monitoring. Clinical Chemistry 31 (12): 1931-1935.

Hitchman M. L. 1978. Measurement of Dissolved Oxygen. In Elving et al. (Eds.). Chemical Analysis vol. 49 Chap. 3 pp. 34-49 59-123. New York: John Wiley & Sons.

Hoel Paul G. 1976. Elementary Statistics Fourth Edition. John Wiley & Sons Inc.. pp. 113-114.

Hrapovic et al. 2003. Picoamperometric detection of glucose at ultrasmall platinum-based biosensors: preparation and characterization. Analytical Chemistry 75:3308-3315.

http://www.merriam-webster.com/dictionary definition for "aberrant" Aug. 19, 2008 p. 1.

Hu et al. 1993. A needle-type enzyme-based lactate sensor for in vivo monitoring, Analytica Chimica Acta 281:503-511.

Huang et al. Aug. 1975. Electrochemical Generation of Oxygen. 1: The Effects of Anions and Cations on Hydrogen Chemisorption and Aniodic Oxide Film Formation on Platinum Electrode. 2: The Effects of Anions and Cations on Oxygen Generation on Platinum . . . U.S. Department of Commerce, National Technical Information Service, Case Western Reserve University, Cleveland, OH.

Huang et al. Sep. 1997. A 0.5mW Passive Telemetry IC for Biomedical Applications. Proceedings of the 23rd European Solid-State Circuits Conference (ESSCIRC '97) pp. 172-175 Southampton UK.

Hunter et al. 2000. Minimally Invasive Glucose Sensor and Insulin Delivery System. MIT Home Automation and Healthcare Consortium. Progress Report No. 25.

Ishikawa et al. 1998. Initial evaluation of a 290-mm diameter subcutaneous glucose sensor: Glucose monitoring with a biocompatible flexible-wire enzyme-based amperometric microsensor in diabetic and nondiabetic humans. Journal of Diabetes and Its Complications 12:295-301.

Jaffari et al. 1995. Recent advances in amperometric glucose biosensors for in vivo monitoring. Physiological Measurement 16:1-15.

Jensen et al. 1997. Fast wave forms for pulsed electrochemical detection of glucose by incorporation of reductive desorption of oxidation products. Analytical Chemistry 69(9):1776-1781.

Jeutter D. C. 1982. A transcutaneous implanted battery recharging and biotelemeter power switching system. IEEE Transactions in Biomedical Engineering 29:314-321.

Johnson (1991). Reproducible electrodeposition of biomolecules for the fabrication of miniature electroenzymatic biosensors. Sensors and Actuators B 5:85-89.

Johnson et al. 1992. In vivo evaluation of an electroenzymatic glucose sensor implanted in subcutaneous tissue. Biosensors & Bioelectronics 7:709-714.

Johnson R.C. et al. 1997. Abstract: Neovascularization of cell transplantation devices: Role of membrane architecture and encapsulated tissue Abstracts of Papers, American Chemistry Society 214:2 P 305-PMSE.

Jovanovic L. 2000. The role of continuous glucose monitoring in gestational diabetes mellitus. Diabetes Technology & Therapeutics ( Suppl 1):S67-S71.

Kacaniklic 1994. Amperometric Biosensors for Detection of L- and D-Amino Acids Based on Coimmobilized Peroxidase and L- and D-Amino Acid Oxidases in Carbon Paste Electrodes. Electroanalysis 6(5-6)381-390.

Kamath et al. 2008. Calibration of a continuous glucose monitor: effect of glucose rate of change. Eighth Annual Diabetes Technology Meeting Nov. 13-15, 2008, p. A88.

Kang et al. 2003. In vitro and short-term in vivo characteristics of a Kel-F thin film modified glucose sensor. Analytical Sciences 19:1481-1486.

Kargol et al. 2001. Studies on the structural properties of porous membranes: measurement of linear dimensions of solutes. Biophysical Chemistry 91:263-271.

Karube et al. 1993. Microbiosensors for acetylcholine and glucose. Biosensors & Bioelectronics 8:219-228.

Kaufman et al. 2001. A pilot study of the continuous glucose monitoring system. Diabetes Care 24(12):2030-2034.

Kaufman. 2000. Role of the continuous glucose monitoring system in pediatric patients. Diabetes Technology & Therapeutics 2(1):S-49-S-52.

Kawagoe et al. 1991. Enzyme-modified organic conducting salt microelectrode. Analytical Chemistry 63:2961-2965.

Keedy et al. 1991. Determination of urate in undiluted whole blood by enzyme electrode. Biosensors & Bioelectronics 6: 491-499.

Kerner et al. 1988. A potentially implantable enzyme electrode for amperometric measurement of glucose. Horm Metabolism Research Suppl. 20:8-13.

Kerner et al. 1993. The function of a hydrogen peroxide-detecting electroenzymatic glucose electrode is markedly impaired in human sub-cutaneous tissue and plasma. Biosensors & Bioelectronics 8:473-482.

Kiechle F.L. 2001. The impact of continuous glucose monitoring on hospital point-of-care testing programs. Diabetes Technology & Therapeutics 3:647-649.

Klueh et al. 2003. Use of Vascular Endothelia Cell Growth Factor Gene Transfer to Enhance Implantable Sensor Function In Vivo. Biosensor Function and Vegf-Gene Transfer pp. 1072-1086.

Klueh et al. 2007. Inflammation and glucose sensors: use of dexamethasone to extend glucose sensor function and life span in vivo. Journal of Diabetes Science and Technology 1 (4):496-504.

Ko Wen H. 1985. Implantable Sensors for Closed-Loop Prosthetic Systems Futura Pub. Co. Inc. Mt. Kisco NY Chapter 15:197-210.

Kondo et al. 1982. A miniature glucose sensor implantable in the blood stream. Diabetes Care. 5(3):218-221.

Koschinsky et al. 1988. New approach to technical and clinical evaluation of devices for self-monitoring of blood glucose. Diabetes Care 11(8): 619-619.

Koschinsky et al. 2001. Sensors for glucose monitoring: Technical and clinical aspects. Diabetes Metababolism Research Reviews 17:113-123.

(56) References Cited

OTHER PUBLICATIONS

Kost et al. 1985. Glucose-sensitive membranes containing glucose oxidase: activity swelling and permeability studies. Journal of Biomedical Materials Research 19:1117-1133.
Koudelka et al. 1989. In vivo response of microfabricated glucose sensors to glycemia changes in normal rats. Biomed Biochim Acta 48(11-12):953-956.
Koudelka et al. 1991. In-vivo behaviour of hypodermically implanted microfabricated glucose sensors. Biosensors & Bioelectronics 6:31-36.
Kraver et al. 2001. A mixed-signal sensor interface microinstrument. Sensors and Actuators A 91:266-277.
Kruger et al. 2000. Psychological motivation and patient education: A role for continuous glucose monitoring. Diabetes Technology & Therapeutics, 2(Suppl 1):S93-97.
Kulys et al. 1994. Carbon-paste biosensors array for long-term glucose measurement. Biosensors& Bioelectronics 9:491-500.
Kunjan et al. Automated blood sampling and glocuse sensing in critical care settings. Journal of Diabetes Science and Technology 2(3):194-200.
Kunzler et al. 1993. Hydrogels based on hydrophilic side chain siloxanes. Poly Mat Sci and Eng 69:226-227.
Kunzler et al. Aug. 21, 1995. Contact lens materials. Chemistry & Industry. 651-655.
Kurtz et al. 2005. Recommendations for blood pressure measurement in humans and experimental animals Part 2: Blood pressure measurement in experimental animals A statement for professionals from the subcommittee of professional and public education . . . Hypertension 45:299-310.
Kusano H. 1989. Glucose enzyme electrode with percutaneous interface which operates indepently of dissolved oxygen. Clin Phys Physiol Meas.10(1): 1-9.
Ladd et al. 1995. Structure Determination by X-ray Crystallography 3rd ed. Plenum 1996 Ch. 1 pp. xxi-xxiv and -58.
Lee et al. 1999. Effects of pore size void volume and pore connectivity on tissue responses. Society for Biomaterials 25th Annual Meeting 171.
Lehmann et al. May 1994. Retrospective valication of a physiological model of glucose-iunsulin interaaction in tyhpe 1 diabetes mellitus. Med. Eng. Phys. 16:193-202.
Lerner et al. 1984. An implantable electrochemical glucose sensor. Ann. N. Y. Academy of Science 428:263-278.
Lewandowski et al. 1988. Evaluation of a miniature blood glucose sensor. Transactions of the American Society of Artifical Internal Organs 34:255-258.
Leypoldt et al. 1984. Model of a two-substrate enzyme electrode for glucose. Analytical Chemistry 56:2896-2904.
Linke et al. 1994. Amperometric biosensor for in vivo glucose sensing based on glucose oxidase immobilized in a redox hydrogel. Biosensors & Bioelectronics 9:151-158.
Loffler et al. 1995. Separation and determination of traces of ammonia in air by means of chromatomembrane cells. Fresenius Journal of Analytical Chemistry 352:613-614.
Lowe 1984. Biosensors. Trends in Biotechnology 2(3):59-65.
Luong et al. 2004. Solubilization of Multiwall Carbon Nanotubes by 3-Aminopropyltriethoxysilane Towards the Fabrication of Electrochemical Biosensors with Promoted Electron Transfer. Electronanalysis 16(1-2):132-139.
Lyandres et al. (2008). Progress toward an in vivo surface-enhanced raman spectroscopy glucose sensor. Diabetes Technology & Therapeutics 10(4): 257-265.
Lyman D. 1960. Polyurethanes. I. The Solution Polymerization of Diisocyanates with Ethylene Glycol. Journal of Polymer Science XLV:45:49.
Madaras et al. 1996. Microfabricated amperometric creatine and creatinine biosensors. Analytica Chimica Acta 319:335-345
Maidan et al. 1992. Elimination of Electrooxidizable Interferent-Produced Currents in Amperometric Biosensors. Analytical Chemistry 64:2889-2896.

Makale et al. 2003. Tissue window chamber system for validation of implanted oxygen sensors. Am. J. Physiol. Heart Circ. Physiol. 284:H2288-2294.
Malin et al. 1999. Noninvasive Prediction of Glucose by Near-Infrared Diffuse Reflectance Spectroscopy, Clinical Chemistry 45:9 1651-1658.
Maran et al. 2002. Continuous subcutaneous glucose monitoring in diabetic patients: A multicenter analysis. Diabetes Care 25(2):347-352.
March W. F. 2002. Dealing with the delay. Diabetes Technology & Therapeutics 4(1):49-50.
Marena et el. 1993. The artifical endocrine pancreas in clinical practice and research. Panminerva Medica 35(2):67-74.
Mascini et al. 1989. Glucose electrochemical probe with extended linearity for whole blood. J Pharm Biomed Anal 7(12): 1507-1512.
Mastrototaro et al. 1991. An electroenzymatic glucose sensor fabricated on a flexible substrate. Sensors and Actuators B 5:139-44.
Mastrototaro et al. 2003. Reproducibility of the continuous glucose monitoring system matches previous reports and the intended use of the product. Diabetes Care 26:256; author reply p. 257.
Mastrototaro J. J. 2000. The MiniMed continuous glucose monitoring system. Diabetes Technology & Therapeutics 2(Suppl 1):S13-8.
Matsumoto et al. 1998. A micro-planar amperometeric glucose sensor unsusceptible to interference species. Sensors and Actuators B 49:68-72 352:613-614.
Matsumoto et al. 2001. A long-term lifetime amperometric glucose sensor with a perfluorocarbon polymer coating. Biosensors & Bioelectronics 16:271-276.
Matthews et al. 1988. An amperometric needle-type glucose sensor testing in rats and man. Diabetic Medicine 5:248-252.
Mazze et al. 2008. Characterizing glucose exposure for individuals with normal glucose tolerance using continuous glucose monitoring and ambulatory glucose profile analysis. Diabetes Technology & Therapeutics 10:149-159.
McCartney et al. 2001. Near-infrared fluorescence lifetime assay for serum glucose based on allophycocyanin-labeled concanavalin A. Analytical Biochemistry 292:216-221.
McGrath et al. 1995. The use of differential measurements with a glucose biosensor for interference compensation during glucose determinations by flow injection analysis. Biosensors & Bioelectronics 10:937-943.
McKean et al. Jul. 7, 1988. A Telemetry Instrumentation System for Chronically Implanted Glucose and Oxygen Sensors. Transactions on Biomedical Engineering 35:526-532.
Memoli et al. 2002. A comparison between different immobilised glucoseoxidase-based electrodes. Journal of Pharmaceutical and Biomedical Analysis 29:1045-1052.
Merriam-Webster Online Dictionary. Definition of "acceleration". http://www.merriam-webster.com/dictionary/Acceleration Jan. 11, 2010.
Merriam-Webster Online Dictionary. Definition of "nominal." http://www.mw.com/dictionary/nominal4/23/2007.
Merriam-Webster Online Dictionary. Definition of "system". http://www.merriam-webster.com/dictionary/System Jan. 11, 2010.
Merriam-Webster Online Dictionary. The term "nominal." http://www.mw.com/dictionary/nominal.
Meyerhoff et al. 1992. On line continuous monitoring of subcutaneous tissue glucose in men by combining portable glucosensor with microdialysis. Diabetologia 35:1087-1092.
Miller A. 1988. Human monocyte/macrophage activation and interleukin 1 generation by biomedical polymers. Journal Biomedical Materials Research 23:713-731.
Miller et al. 1989. Generation of IL1-like activity in response to biomedical polymer implants: a comparison of in vitro and in vivo models. Journal of Biomedical Materials Research 23:1007-1026.
Miller et al. 1989. In vitro stimulation of fibroblast activity by factors generated from human monocytes activated by biomedical polymers. Journal of Biomedical Materials Research 23:911-930.
Moatti-Sirat et al. 1992. Evaluating in vitro and in vivo the interference of ascorbate and acetaminophen on glucose detection by a needle-type glucose sensor. Biosensors & Bioelectronics 7:345-352.

(56) References Cited

OTHER PUBLICATIONS

Moatti-Sirat et al. 1992. Towards continuous glucose monitoring: in vivo evaluation of a miniaturized giucose sensor implanted for several days in rat subcutaneous tissue. Diabetologia 35:224-230.
Moatti-Sirat et al. 1994. Reduction of acetaminophen interference in glucose sensors by a composite Nafion membrane: demonstration in rats and man. Diabetologia 37(6):610-616.
Morff et al. 1990. Microfabrication of reproducible economical electroenzymatic glucose sensor. Annual International Conference of the IEEE Engineering in Medicine and Biology Society 12(2):0483-0484.
Mosbach et al. 1975. Determination of heat changes in the proximity of immobilized enzymes with an enzyme termistor and its use for the assay of metabolites. Biochimca & Biophysica Acta (Enzymology) 403:256-265.
Motonaka et al. 1993. Determination of cholesteral and cholesteral ester with novel enzyme microsensors. Analytical Chemistry 65:3258-3261.
Moussy et al. 2000. Biomaterials community examines biosensor biocompatibility. Diabetes Technology & Therapeutics 2:473-477.
Mowery et al. 2000. Preparation and characterization of hydrophobic polymeric films that are thromboresistant via nitric oxide release. Biomaterials 21:9-21.
Murphy et al. 1992. Polymer membranes in clinical sensor applications. II. The design and fabrication of permselective hydrogels for electrochemical devices. Biomaterials 13(14):979-990.
Muslu. 1991. Trickling filter performance. Applied Biochemistry and Biotechnology 37:211-224.
Myler et al. 2002. Ultra-thin-polysiloxane-film-composite membranes for the optimisation of amperometric oxidase enzyme electrodes. Biosensors & Bioelectronics 17:35-43.
Nafion® 117 Solution Product Description Product No. 70160 Sigma-Aldrich Corp. St. Louis MO. Apr. 7, 2005.
Nakayama et al. 1992. Surface fixation of hydrogels: heparin and glucose oxidase hydrogelated surfaces. ASAIO Journal M421-M424.
Nam et al. 2000. A novel fabrication method of macroporous biodegradable polymer scaffolds using gas foaming salt as a porogen additive. Journal of Biomedical Materials Research 53:1-7.
Ohara et al. 1994. "Wired" enzyme electrodes for amperometric determination of glucose or lactate in the presence of interfering substances. Analytical Chemistry 66:2451-2457.
Ohara et al. Dec. 1993. Glucose electrodes based on cross-linked bis(22'-bipyridine)chlorooosmium(+/2+) complexed poly(l-vinylimidazole) films. Analytical Chemistry 65:3512-3517.
Okuda et al. 1971. Mutarotase effect on micro determinations of D-glucose and its anomers with p-D-glucose oxidase. Analytical Biochemistry 43:312-315.
Oxford English Dictionary Online. Definition of "impending". http://www.askoxford.com/results/?view=dev dict&field-12668446 Impending&branch= Jan. 11, 2010.
Palmisano et al. 2000. Simultaneous monitoring of glucose and lactate by an interference and cross-talk free dual electrode amperometric biosensor based on electropolymerized thin films. Biosensors & Bioelectronics 15:531-539.
Panetti 2002. Differential effects of sphingosine 1-phosphate and lysophosphatidic acid on endothelial cells. Biochimica et Biophysica Acta 1582:190-196.
Park et al. 2002. Gas separation properties of polysiloxane/polyether mixed soft segment urethane urea membranes. Journal of Membrane Science 204: 257-269.
Patel et al. 2003. Amperometric glucose sensors based on ferrocene containing polymeric electron transfer systems—a preliminary report. Biosensors & Bioelectronics 18:1073-6.
Peacock et al. 2008. Cardiac troponin and outcome in acute heart failure. N. Engl. J. Med. 358: 2117-2126.
Pegoraro et al. 1995. Gas transport properties of siloxane polyurethanes. Journal of Applied Polymer Science 57:421-429.
Pfeiffer E.F. 1990. The glucose sensor: the missing link in diabetes therapy. Horn Metababolism Research Suppl. 24:154-164.
Pfeiffer et al. 1992. On line continuous monitoring of subcutaneous tissue glucose is feasible by combining portable glucosensor with microdialysis. Horm. Metabolism Research 25:121-124.
Phillips and Smith. 1988. Bromedical Applications of Polyurethanes: Implications of Failure Mechanisms. Journal of Biomat. Appl. 3:202-227.
Pichert et al. 2000. Issues for the coming age of continuous glucose monitoring. Diabetes Educator 26(6):969-980.
Pickup et al. 1987/1988. Implantable glucose sensors: choosing the appropriate sensor strategy. Biosensors 3:335-346.
Pickup et al. 1988. Progress towards in vivo glucose sensing with a ferrocene-mediated amperometric enzyme electrode, in Ferrocene-Mediated Glucose Sensor, pp. 34-36.
Pickup et al. 1989. In vivo molecular sensing in diabetes mellitus: an implantable glucose sensor with direct electron transfer. Diabetologia 32:213-217 (1989).
Pickup et al. 1989. Potentially-implantable amperometric glucose sensors with mediated electron transfer: improving the operating stability. Biosensors 4:109-119.
Pickup et al. 1993. Developing glucose sensors for in vivo use. TIBTECH vol. 11: 285-291.
Pineda et al. 1996. Bone regeneration with resorbable polymeric membranes. III. Effect of poly(L-lactide) membrane pore size on the bone healing process in large defects. Journal of Biomedical Materials Research 31:385-394.
Pinner et al. 1959. Cross-linking of cellulose acetate by ionizing radiation. Nature vol. 184 1303-1304.
Pishko et al. 1991. Amperometric glucose microelectrodes prepared through immobilization of glucose oxidase in redox hydrogels. Analytical Chemistry 63:2268-72.
Pitzer et al. 2001. Detection of hypoglycemia with the GlucoWatch biographer. Diabetes Care 24(5):881-885.
Poitout et al. 1991. In Vitro and In Vivo Evaluation in Dogs of a Miniaturized Glucose Sensor. ASAIO Transactions 37:M298-M300.
Poitout et al. 1993. A glucose monitoring system for on line estimation in man of blood glucose concentration using a miniaturized glucose sensor implanted in the subcutaneous tissue and a wearable control unit. Diabetologia 36:658-663.
Poitout et al. 1994. Development of a glucose sensor for glucose monitoring in man: the disposable implant concept. Clinical Materials 15:241-246.
Postlethwaite et al. 1996. Interdigitated array electrode as an alternative to the rotated ring-disk electrode for determination of the reaction products of dioxygen reduction. Analytical Chemistry 68:2951-2958.
Prabhu et al. 1981. Electrochemical studies of hydrogen peroxide at a platinum disc electrode. Electrochimica Acta 26(6):725-729.
Quinn et al. 1995. Kinetics of glucose delivery to subcutaneous tissue in rats measured with 0.3-mm amperometric microsensors. The American Physiological Society E155-E161.
Quinn et al. 1997. Biocompatible glucose-permeable hydrogel for in situ coating of implantable biosensors. Biomaterials 18:1665-1670.
Rabah et al. 1991. Electrochemical wear of graphite anodes during electrolysis of brine. Carbon 29(2):165-171.
Ratner B.D. 2002. Reducing capsular thickness and enhancing angiogenesis around implant drug release systems. Journal of Controlled Release 78:211-218.
Reach et al. 1986. A Method for Evaluating in vivo the Functional Characteristics of Glucose Sensors. Biosensors 2:211-220.
Reach et al. 1992. Can continuous glucose monitoring be used for the treatment of diabetes? Analytical Chemistry 64(5):381-386.
Reach G. 2001. Which threshold to detect hypoglycemia? Value of receiver-operator curve analysis to find a compromise between sensitivity and specificity. Diabetes Care 24(5):803-804.
Reach Gerard. 2001. Letters to the Editor Re: Diabetes Technology & Therapeutics 2000;2:49-56. Diabetes Technology & Therapeutics 3(1):129-130.
Rebrin et al. 1989. Automated feedback control of subcutaneous glucose concentration in diabetic dogs. Diabetologia 32:573-76.
Rebrin et al. 1992. Subcutaneous glucose monitoring by means of electrochemical sensors: fiction or reality? Journal of Biomedical Engineering 14:33-40.

(56) References Cited

OTHER PUBLICATIONS

Reusch. 2004. Chemical Reactivity. Organometallic Compounds. Virtual Textbook of Organic Chem. pp. 1-16 http://www.cem.msu.edu/~reusch/VirtualText/orgmetal.htm.

Rhodes et al. 1994. Prediction of pocket-portable and implantable glucose enzyme electrode performance from combined species permeability and digital simulation analysis. Analytical Chemistry 66(9):1520-1529.

Rigla et al. 2008. Real-time continuous glucose monitoring together with telemedical assistance improves glycemic control and glucose stability in pump-treated patients. Diabetes Technology & Therapeutics 10:194-199.

Rivers et al. 2001. Central venous oxygen saturation monitoring in the critically ill patient. Current Opinion in Critical Care 7:204-211.

Sachlos et al. 2003. Making Tissue Engineering Scaffolds Work. Review on the Application of Sold Freeform Fabrication Technology to the Production of Tissue Engineering Scaffolds. European Cells and Materials 5:29-40.

Sakakida et al. 1992. Development of Ferrocene-Mediated Needle-Type Glucose Sensor as a Measure of True Subcutaneous Tissue Glucose Concentrations. Artificial Organs Today 2(2):145-158.

Sakakida et al. 1993. Ferrocene-Mediated Needle Type Glucose Sensor Covered with Newly Designed Biocompatible Membrane. Sensors and Actuators B 13-14:319-322.

Salardi et al. 2002. The glucose area under the profiles obtained with continuous glucose monitoring system relationships with HbA1c in pediatric type 1 diabetic patients. Diabetes Care 25(10):1840-1844.

San Diego Plastics Inc. 2009. Polyethylene Data Sheet http://www.sdplastics.com/polyeth.html.

Sanders et al. 2003. Fibrous Encapsulation of Single Polymer Microfibers Depends on their Vertical Dimension in subcutaneous Tissue. Polymer Microfibers pp. 1181-1187.

Sansen et al. 1985. Glucose sensor with telemetry system. In Ko W. H. (Ed.). Implantable Sensors for Closed Loop Prosthetic Systems. Chap. 12 pp. 167-175 Mount Kisco NY: Futura Publishing Co.

Sansen et al. 1990. A smart sensor for the voltammetric measurement of oxygen or glucose concentrations. Sensors and Actuators B 1:298-302.

Schmidt et al. 1993. Glucose concentration in subcutaneous extracellular space. Diabetes Care 16(5):695-700.

Schmidtke et al. 1998. Measurement and modeling of the transient difference between blood and subcutaneous glucose concentrations in the rat after injection of insulin. Proc Natl Acad Sci U S A 95 294-299.

Schoemaker et al. 2003. The SCGM1 system: Subcutaneous continuous glucose monitoring based on microdialysis technique. Diabetes Technology & Therapeutics 5(4):599-608.

Schoonen et al. 1990 Development of a potentially wearable glucose sensor for patients with diabetes mellitus: design and in-vitro evaluation. Biosensors & Bioelectronics 5:37-46.

Schuler et al. 1999. Modified gas-permeable silicone rubber membranes for covalent immobilisation of enzymes and their use in biosensor development. Analyst 124:1181-1184.

Selam J. L. 1997. Management of diabetes with glucose sensors and implantable insulin pumps. From the dream of the 60s to the realities of the 90s. ASAIO J 43:137-142.

Service et al. 1970. Mean amplitude of glycemic excursions a measure of diabetic instability, Diabetes 19:644-655.

Service et al. 1987. Measurements of glucose control, Diabetes Care 10: 225-237.

Service R. F. 2002. Can sensors make a home in the body? Science 297:962-3.

Sharkawy et al. 1996, Engineering the tissue which encapsulates subcutaneous implants. I. Diffusion properties. Journal of Biomedical Materials Research 37:401-412.

Shaw et al. 1991. In vitro testing of a simply constructed highly stable glucose sensor suitable for implantation in diabetic patients. Biosensors & Bioelectronics 6:401-406.

Shichiri et al. 1982. Wearable artificial endocrine pancreas with needle-type glucose sensor. Lancet 2:1129-1131.

Shichiri et al. 1983. Glycaemic Control in Pancreatectomized Dogs with a Wearable Artificial Endocrine Pancreas. Diabetologia 24:179-184.

Shichiri et al. 1985. Needle-type Glucose Sensor for Wearable Artificial Endocrine Pancreas. Implantable Sensors 197-210.

Shichiri et al. 1986. Telemetry Glucose Monitoring Device with Needle-Type Glucose Sensor: A Useful Tool for Blood Glucose Monitoring in Diabetic Individuals. Diabetes Care Inc. 9(3):298-301.

Shichiri et al. 1989. Membrane Design for Extending the Long-Life of an Implantable Glucose Sensor. Diabetes Nutrition Metabolism 2:309-313.

Shults et al. 1994. A telemetry-instrumentation system for monitoring multiple subcutaneously implanted glucose sensors. IEEE Transactions on Biomedical Engineering 41(10):937-942.

Sieminski et al. 2000. Biomaterial-microvasculature interactions. Biomaterials 21:2233-2241.

Skyler J. S. 2000. The economic burden of diabetes and the benefits of improved glycemic control: The potential role of a continuous glucose monitoring system. Diabetes Technology & Therapeutics 2(Suppl 1):S7-S12.

Slater-Maclean et al. 2008. Accuracy of glycemic measurements in the critically ill. Diabetes Technology & Therapeutics 10:169-177.

Sokol et al. 1980. Immobilized-enzyme rate-determination method for glucose analysis. Clinical Chemistry 26(1):89-92.

Sriyudthsak et al. 1996. Enzyme-epoxy membrane based glucose analyzing system and medical applications. Biosensors & Bioelectronics 11:735-742.

Steil et al. 2003. Determination of plasma glucose during rapid glucose excursions with a subcutaneous glucose sensor. Diabetes Technology & Therapeutics 5(1 ):27-31.

Stern et al. 1957. Electrochemical polarization: 1. A theoretical analysis of the shape of polarization curves. Journal of the Electrochemical Society 104(1):56-63.

Sternberg et al. 1988. Covalent enzyme coupling on cellulose acetate membranes for glucose sensor development. Analytical Chemistry 69:2781-2786.

Sternberg et al. 1988. Study and Development of Multilayer Needle-type Enzyme-based Glucose Microsensors. Biosensors 4:27-40.

Stokes. 1988. Polyether Polyurethanes: Biostable or Not? Journal of Biomaterials Applications 3:228-259.

Suh et al. 2002. Behavior of fibroblasts on a porous hyaluronic acid incorporated collagen matrix. Yonsei Medical Journal 43(2):193-202.

Sumino T. et al. 1998. Preliminary study of continuous glucose monitoring with a microdialysis technique. Proceedings of the IEEE 20(4):1775-1778.

Takegami et al. 1992. Pervaporation of ethanol water mixtures using novel hydrophobic membranes containing polydimethylsiloxane. Journal of Membrane Science 75(93-105).

Tanenberg et al. 2000. Continuous glucose monitoring system: A new approach to the diagnosis of diabetic gastroparesis. Diabetes Technology & Therapeutics 2(Suppl)1 :S73-80.

Tang et al. 1993. Fibrin(ogen) mediates acute inflammatory responses to biomaterials. J Experimental Medicine 178:2147-2156.

Tang et al. 1995. Inflammatory responses to biomaterials. American Journal of Clinical Pathology 103:466-471.

Tang et al. 1996. Molecular determinants of acute inflammatory responses to biomaterials. Journal of Clinical Investigation 97:1329-1334.

Tang et al. 1998. Mast cells mediate acute inflammatory responses to implanted biomaterials. Proc Natl Acad Sci U S A 95:8841-8846.

Tatsuma et al. 1991. Oxidase/peroxidase bilayer-modified electrodes as sensors for lactate pyruvate cholesteral and uric acid. Analytica Chimica Acta 242:85-89.

Thome et al. 1995. Abstract—Can the decrease in subcutaneous glucose concentration precede the decrease in blood glucose level? Proposition for a push-pull kinetics hypothesis. Horm. Metabolism Research 27:53.

Thome-Duret et al. 1996. Modification of the sensitivity of glucose sensor implanted into subcutaneous tissue. Diabetes Metabolism 22:174-178.

(56) References Cited

OTHER PUBLICATIONS

Thome-Duret et al. 1996. Use of a subcutaneous glucose sensor to detect decreases in glucose concentration prior to observation in blood. Analytical Chemistry 68:3822-3826.
Thome-Duret et al. 1998. Continuous glucose monitoring in the free-moving rat. Metabolism 47:799-803.
Thompson et al. 1986. In Vivo Probes: Problems and Perspectives Department of Chemistry University of Toronto Canada pp. 255-261.
Tibell et al. 2001. Survival of macroencapsulated allogeneic parathyroid tissue one year after transplantation in nonimmunosuppressed humans. Cell Transplant 10:591-9.
Tierney et al. 2000. Effect of acetaminophen on the accuracy of glucose measurements obtained with the GlucoWatch biographer. Diabetes Technology & Therapeutics 2:199-207.
Tierney et al. 2000. The GlucoWatch® biographer: A frequent automatic and noninvasive glucose monitor. Ann. Med. 32:632-641.
Torjman et al. 2008. Glucose monitoring in acute care: technologies on the horizon. Journal of Diabetes Science and Technology 2(2):178-181.
Trecroci D. 2002. A Glimpse into the Future—Continuous Monitoring of Glucose with a Microfiber. Diabetes Interview 42-43.
Tse and Gough. 1987. Time-Dependent Inactivation of Immobilized Glucose Oxidase and Catalase. Biotechnology & Bioengineering 29:705-713.
Turner A.P.F. 1988. Amperometric biosensor based on mediator-modified electrodes. Methods in Enzymology 137:90-103.
Turner and Pickup, 1985. Diabetes mellitus: biosensors for research and management. Biosensors 1:85-115.
Turner et al. 1984. C arbon Monoxide: Acceptor Oxidoreductase from Pseudomonas Thermocarboxydovorans Strain C2 and its use in a Carbon Monoxide Sensor. Analytica Chimica Acta 163: 161-174.
Unger et al. 2004, Glucose control in the hospitalized patient. Emergency Medicine 36(9):12-18.
Updike et al. 1967. The enzyme electrode, Nature 214:986-988.
Updike et al. 1988. Laboratory Evaluation of New Reusable Blood Glucose Sensor. Diabetes Care 11:801-807.
Updike et al. 1994. Enzymatic glucose sensor: Improved long-term performance in vitro and in vivo. ASAIO Journal 40(2):157-163.
Updike et al. 1997. Principles of long-term fully implanted sensors with emphasis on radiotelemetric monitoring of blood glucose form inside a subcutaneous foreign body capsule (FBC). In Fraser ed., Biosensors in the Body. New York. John Wiley & Sons pp. 117-137.
Updike et al. 2000. A subcutaneous glucose sensor with improved longevity dynamic range and stability of calibration. Diabetes Care 23(2):208-214.
Utah Medical Products Inc. Blood Pressure Tranducers product specifications. 6 pp. 2003-20062003.
Vadgama P. Nov. 1981. Enzyme electrodes as practical biosensors. Journal of Medical Engineering & Technology 5(6)293-298.
Vadgama. 1988. Diffusion limited enzyme electrodes. NATO ASI Series: Series C Math and Phys. Sci. 226:359-377.
Van den Berghe 2004. Tight blood glucose control with insulin in "real-life" intensive care. Mayo Clin Proc 79(8):977-978.
Velho et al. 1989. In vitro and in vivo stability of electrode potentials in needle-type glucose sensors. Influence of needle material. Diabetes 38:164-171.
Velho et al. 1989. Strategies for calibrating a subcutaneous glucose sensor. Biomedica et Biochimica Acta 48(11/12):957-964.
von Woedtke et al. 1989. In situ calibration of implanted electrochemical glucose sensors. Biomedica et Biochimica Acta 48(11/12)943-952.
Wade Jr. L.G. Organic Chemistry Chapter 17 Reactions of Aromatic Compounds pp. 762-7631987.
Wagner et al, 1998. Continuous amperometric monitoring of glucose in a brittle diabetic chimpanzee with a miniature subcutaneous electrode. Proc. Natl. Acad. Sci. A 95:6379-6382.
Wang et al. 1994. Highly Selective Membrane-Free Mediator-Free Glucose Biosensor. Analytical Chemistry 66:3600-3603.
Wang et al. 1997. Improved ruggedness for membrane-based amperometric sensors using a pulsed amperometric method. Analytical Chemistry 69:4482-4489.
Ward et al. 2000. Rise in background current overtime in a subcutaneous glucose sensor in the rabbit: Relevance to calibration and accuracy. Biosensors & Bioelectronics 15:53-61.
Ward et al. 2000. Understanding Spontaneous Output Fluctuations of an Amperometric Glucose Sensor: Effect of Inhalation Anesthesia and Use of a Nonenzyme Containing Electrode. ASAIO Journal 540-546.
Ward et al. 2002. A new amperometric glucose microsensor: In vitro and short-term in vivo evaluation. Biosensors & Bioelectronics 17:181-189.
Wientjes, K. J. C. 2000. Development of a glucose sensor for diabetic patients (Ph.D. Thesis).
Wikipedia 2006. "Intravenous therapy" http://en.wikipedia.org/wiki/Intravenous_therapy Aug. 15, 2006 6 pp.
Wiley Electrical and Electronics Engineering Dictionary. 2004. John Wiley & Sons Inc. pp. 141142 548 549.
Wilkins et al. 1988. The coated wire electrode glucose sensor Horm Metabolism Research Suppl. 20:50-55.
Wilkins et al. 1995. Glucose monitoring: state of the art and future possibilities. Med Eng Phys 18:273-288.
Wilkins et al. 1995. Integrated implantable device for long-term glucose monitoring. Biosensors & Bioelectronics 10:485-494.
Wilson et al. 1992. Progress toward the development of an implantable sensor for glucose. Clinical Chemistry 38(9):1613-1617.
Wilson et al. 2000. Enzyme-based biosensors for in vivo measurements. Chemistry Review 100:2693-2704.
Wood W. et al. Mar. 1990. Hermetic Sealing with Epoxy. Mechanical Engineering 1-3.
Woodward. 1982. How Fibroblasts and Giant Cells Encapsulate Implants: Considerations in Design of Glucose Sensor. Diabetes Care 5:278-281.
Worsley et al. 2008. Measurement of glucose in blood with a phenylboronic acid optical sensor. Journal of Diabetes Science and Technology 2(2):213-220.
Wright et al. 1999. Bioelectrochemical dehalogenations via direct electrochemistry of poly(ethylene oxide)-modified myoglobin. Electrochemistry Communications 1:603-611.
Wu et al. 1999. In situ electrochemical oxygen generation with an immunoisolation device. Annals New York Academy of Sciences pp. 105-125.
Yamasaki et al. 1989. Direct measurement of whole blood glucose by a needle-type sensor. Clinica Chimica Acta. 93:93-98.
Yamasaki Yoshimitsu. Sep. 1984. The development of a needle-type glucose sensor for wearable artificial endocrine pancreas. Medical Journal of Osaka University 35(1-2):25-34.
Yang et al 1996. A glucose biosensor based on an oxygen electrode: In-vitro performances in a model buffer solution and in blood plasma. Biomedical Instrumentation & Technology 30:55-61.
Yang et al. 1998. Development of needle-type glucose sensor with high selectivity. Science and Actuators B 46:249-256.
Yang et al. 2004. A Comparison of Physical Properties and Fuel Cell Performance of Nafion and Zirconium Phosphate/Nafion Composite Membranes. Journal Of Membrane Science 237:145-161.
Ye et al. 1993. High Current Density 'Wired' Quinoprotein Glucose Dehydrogenase Electrode. Analytical Chemistry 65:238-241.
Zamzow et al. 1990. Development and evaluation of a wearable blood glucose monitor. ASAIO Transactions; 36(3): pp. M588-M591.
Zethelius et al. 2008. Use of multiple biomarkers to improve the prediction of death from cardiovascular causes. N. Engl. J. Med. 358: 2107-2116.
Zhang et al 1993. Electrochemical oxidation of H202 on Pt and Pt + Ir electrodes in physiological buffer and its applicability to H202-based biosensors. Journal of Electroanalytical Chemistry 345:253-271.
Zhang et al. 1993. In vitro and in vivo evaluation of oxygen effects on a glucose oxidase based implantable glucose sensor. Analytica Chimica Acta 281:513-520.

(56) References Cited

OTHER PUBLICATIONS

Zhang et al. 1994. Elimination of the acetaminophen interference in an implantable glucose sensor. Analytical Chemistry 66(7):1183-1188.
Zhu et al. 1994. Fabrication and characterization of glucose sensors based on a microarray H2O2 electrode. Biosensors & Bioelectronics 9: 295-300.
Zhu et al. 2002. Planar amperometric glucose sensor based on glucose oxidase immobilized by chitosan film on Prussian blue layer. Sensors 2:127-136.
PCT US2006/014403, filed Apr. 14, 2006: International Search Report and Written Opinion dated Sep. 6, 2006.
PCT/US2006/014403, filed Apr. 14, 2006: International Preliminary Report on Patentability daed Oct. 16, 2007.

* cited by examiner

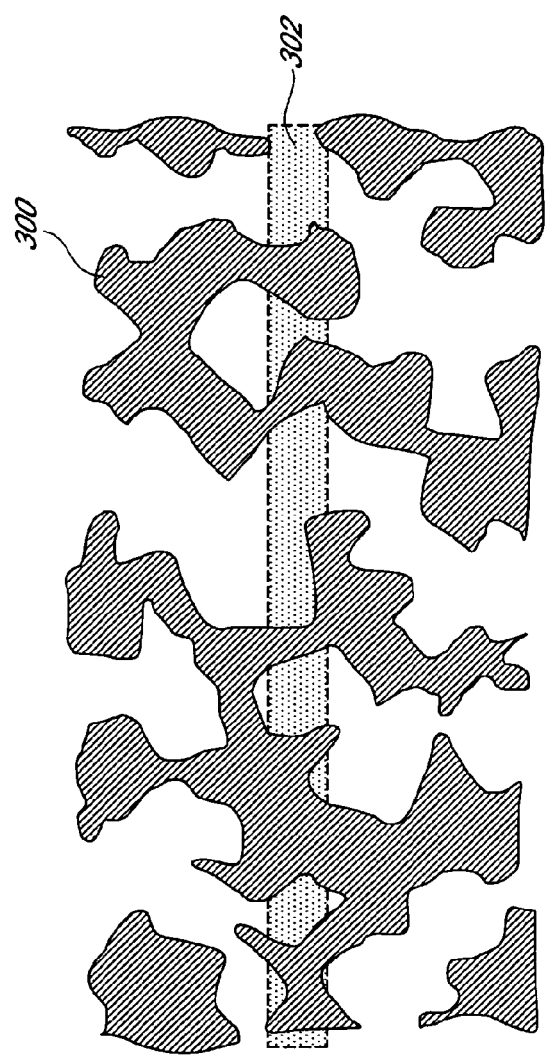
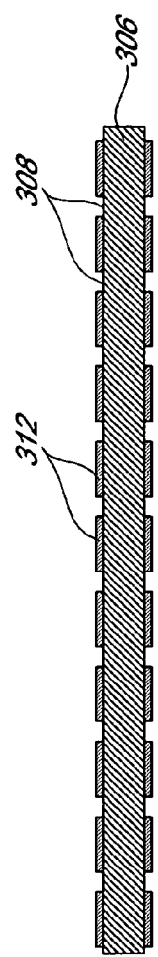
FIG. 9A
FIG. 9B

ANALYTE SENSING BIOINTERFACE

INCORPORATION BY REFERENCE TO RELATED APPLICATIONS

Any and all priority claims identified in the Application Data Sheet, or any correction thereto, are hereby incorporated by reference under 37 CFR 1.57. This application is a continuation of U.S. application Ser. No. 13/285,880, filed Oct. 31, 2011, which is a continuation of U.S. application Ser. No. 11/404,929, filed Apr. 14, 2006, now U.S. Pat. No. 8,060,174, which claims the benefit of U.S. Provisional Application No. 60/671,622, filed Apr. 15, 2005, and U.S. Provisional Application No. 60/683,923, filed May 23, 2005. Each of the aforementioned applications is incorporated by reference herein in its entirety, and each is hereby expressly made a part of this specification.

FIELD OF THE INVENTION

The present invention relates to the field of biosensing. More particularly, the present invention relates to analyte sensors for implantation into a host.

BACKGROUND OF THE INVENTION

Biosensors are devices that can be used to detect the presence or amount of analytes, such as biomolecules, in a biological sample. Some biosensors are designed to detect analytes in a living host. Such detection can advantageously be done through the use of implantable biosensors, which are implanted intravascularly or within tissue to detect the presence or amount of analyte at the implantation location. One practical application of implantable biosensors is implantable glucose sensors that continuously monitor a patient's blood glucose level.

One type of implantable glucose sensor utilizes glucose oxidase that catalyzes the reaction between glucose and oxygen to produce gluconic acid and hydrogen peroxide. The hydrogen peroxide can be detected by measuring the electrochemical oxidation of the hydrogen peroxide at an appropriate electrode, such as a platinum electrode. The current generated by this oxidation can be related to the amount of hydrogen peroxide in the vicinity of the electrode, and hence, the amount of glucose in the vicinity of the sensor. In some glucose sensors, the electrode is coated with an analyte membrane system. The analyte membrane system may contain the glucose oxidase enzyme as well as one or more polymeric membranes that control the diffusion of glucose or block or limit certain undesired species from reaching the electrode, such as is described further in U.S. application Ser. No. 10/153,356, filed on May 22, 2002, which is incorporated herein by reference in its entirety.

One difficulty encountered with implantable biosensors, such as implantable glucose sensors, is that many of these devices tend to lose their function with time after implantation. While not being bound by any particular theory, this decrease in function can at least partially be attributed to the host's foreign body response (FBR) to the implant. Typical FBR response to an implantable biosensor is illustrated in FIG. 1. FBR is a local inflammatory response that results in the formation of a barrier cell layer 40 around the surface of the implant 47. This layer generally consists of macrophages and foreign body giant cells 41. An intermediate layer 42, consisting of fibroblasts 43 and a fibrous matrix 44, typically form over the barrier cell layer 40. Finally, an outer layer 46 consisting of loose connective granular tissue and new blood vessels 45 forms over the intermediate layer. The barrier cell layer 40 can have the adverse effect of blocking transport of the analyte to the analyte sensor 47. Furthermore, lack of vascularization in the intermediate 42 and barrier cell 40 layers decreases analyte availability to the sensor. Thus, once the FBR acts to induce the above-described tissue growth around the implanted biosensor, sensing ability decreases.

SUMMARY OF THE INVENTION

Devices and methods are needed that address the FBR's negative effects on biosensing. The devices and methods of the preferred embodiments address these negative effects, and offer other benefits and advantages, as described herein.

Accordingly, in a first aspect, an implantable analyte sensor is provided, comprising an electrically non-conductive biocompatible matrix comprising a plurality of passageways extending from openings in an exterior surface of the matrix into an interior portion of the matrix; a working electrode comprising an electrically conductive material, wherein an electroactive surface of the working electrode is within the matrix; and electronics electrically coupled to the working electrode, the electronics configured to detect a current flowing through the working electrode or a voltage of the working electrode, wherein the current or voltage is indicative of a quantity of an analyte within the passageways.

In an embodiment of the first aspect, the implantable sensor comprises a membrane coating surfaces of at least some of the passageways in the interior portion of the matrix, the membrane comprising a component that affects a rate of diffusion of the analyte through the membrane.

In an embodiment of the first aspect, the implantable sensor comprises a membrane coating surfaces of at least some of the passageways in the interior portion of the matrix, the membrane comprising a component that is capable of reacting with the analyte to produce a species that is capable of electrochemically reacting at a surface of the working electrode.

In an embodiment of the first aspect, the implantable sensor comprises a reference electrode disposed within the matrix, wherein an electroactive surface of the reference electrode is within the matrix, and wherein at least a portion of the matrix electrically insulates the reference electrode from the working electrode.

In an embodiment of the first aspect, the implantable sensor comprises a reference electrode disposed on an exterior surface of the matrix, wherein at least a portion of the matrix electrically insulates the reference electrode from the working electrode.

In an embodiment of the first aspect, the implantable sensor comprises a counter electrode disposed within the matrix, wherein an electroactive surface of the counter electrode is within the matrix, and wherein at least a portion of the matrix electrically insulates the counter electrode from the working electrode.

In an embodiment of the first aspect, the implantable sensor comprises a counter electrode disposed on an exterior surface of the matrix, wherein at least a portion of the matrix electrically insulates the counter electrode from the working electrode.

In an embodiment of the first aspect, the matrix is a substantially solid material and the passageways comprise pores within the substantially solid material. The matrix can be a mesh of fibers. The fibers can comprise an electrically non-conductive material or an electrically conductive material. The fibers can further comprise a membrane coating the fibers.

In an embodiment of the first aspect, the working electrode has a membrane coating disposed thereon.

In a second aspect, a sensor is provided for measuring an analyte in a host, the sensor comprising a biointerface comprising a porous biocompatible matrix, wherein electroactive surfaces are distributed within at least some pores in the biointerface.

In an embodiment of the second aspect, the electroactive surfaces have a membrane coating disposed thereon.

In an embodiment of the second aspect, the porous biocompatible matrix is configured to support tissue ingrowth and comprises a plurality of interconnected cavities and a solid portion, and wherein a substantial number of the interconnected cavities are greater than or equal to about 20 microns in at least one dimension.

In an embodiment of the second aspect, the porous biocompatible matrix comprises a length of greater than one cavity in each of three dimensions substantially throughout the matrix.

In an embodiment of the second aspect, the cavities and a plurality of cavity interconnections are formed in a plurality of layers, wherein each layer has different cavity dimensions.

In an embodiment of the second aspect, the porous biocompatible matrix is configured to promote vascularization and interfere with barrier cell layer formation within the matrix, whereby the biocompatible matrix is suitable for long-term analyte transport in vivo.

In an embodiment of the second aspect, the porous biocompatible matrix comprises a plurality of fibers.

In an embodiment of the second aspect, the plurality of fibers are selected from the group consisting of woven fibers and non-woven fibers.

In an embodiment of the second aspect, at least a portion of the plurality of fibers comprise an electrode core.

In an embodiment of the second aspect, the fibers comprising an electrode core comprise a membrane surrounding the electrode core.

In an embodiment of the second aspect, the electroactive surfaces comprise an electroactive surface of at least one working electrode.

In an embodiment of the second aspect, the electroactive surfaces further comprise an electroactive surface of at least one reference electrode.

In an embodiment of the second aspect, the sensor further comprises sensor electronics operably connected to the electroactive surfaces.

In an embodiment of the second aspect, the sensor is configured to measure glucose.

In a third aspect, a sensor for measuring an analyte in a host is provided, the sensor comprising an analyte sensing mechanism disposed within a porous biocompatible matrix.

In an embodiment of the third aspect, dimensions of the porous biocompatible matrix comprising the sensing mechanism are less than about 1000 microns.

In an embodiment of the third aspect, the porous biocompatible matrix and the sensing mechanism are configured to resist barrier cell layer formation.

In an embodiment of the third aspect, the sensing mechanism comprises a working electrode.

In an embodiment of the third aspect, the working electrode is a wire electrode.

In an embodiment of the third aspect, the working electrode is a substantially planar electrode.

In an embodiment of the third aspect, the sensing mechanism further comprises an enzyme domain disposed over the working electrode.

In an embodiment of the third aspect, the sensing mechanism further comprises an electrode domain disposed between the enzyme domain in the working electrode.

In an embodiment of the third aspect, the sensing mechanism further comprises a resistance domain disposed over the enzyme domain.

In an embodiment of the third aspect, the sensing mechanism further comprises a bioprotective domain disposed over the enzyme domain.

In an embodiment of the third aspect, the sensing mechanism further comprises a resistance domain disposed between the enzyme domain and the bioprotective domain.

In a fourth aspect, a method of detecting an analyte within tissue of a host is provided, comprising implanting an analyte sensor according to the first aspect within the tissue; allowing tissue to grow within at least a portion of some of the passageways; and detecting current flowing through the working electrode or a voltage of the working electrode, thereby detecting the quantity of an analyte within the passageways.

In an embodiment of the fourth aspect, allowing tissue to grow within at least a portion of some of the passageways comprises formation of one or more host tissue materials within the passageways, the host tissue materials selected from the group consisting of a fibrous matrix, blood vessels, fibroblasts, connective granular tissue, macrophages, and foreign body giant cells.

In a fifth aspect, a method of manufacturing an analyte sensor according to the first aspect is provided, comprising forming a first layer of an electrically non-conductive material; depositing a layer of an electrically conductive material on the first layer of the electrically non-conductive material; depositing a second layer of electrically non-conductive material onto the layer of electrically conductive material; and etching the deposited layers to form interconnected pores in the layers, at least some of the pores extending from an exterior surface of the electrically non-conductive material to the electrically conductive material.

In an embodiment of the fifth aspect, at least one of the forming and depositing steps comprises dip coating.

In an embodiment of the fifth aspect, at least one of the forming and depositing steps comprises vapor deposition.

In an embodiment of the fifth aspect, at least one of the forming and depositing steps comprises lamination.

In an embodiment of the fifth aspect, at least one of the forming and depositing steps comprises spin coating.

In an embodiment of the fifth aspect, the method further comprises coating the pores' interior surfaces with an analyte membrane system, the analyte membrane system comprising at least one of a component that affects the analyte's rate of diffusion through the analyte membrane system and a component that reacts with the analyte to produce a species that electrochemically reacts at the surface of the electrically conductive material.

In an embodiment of the fifth aspect, coating comprises dip coating.

In an embodiment of the fifth aspect, coating comprises vapor deposition.

In an embodiment of the fifth aspect, coating comprises spin coating.

In a sixth aspect, a method of manufacturing an analyte sensor according to the first aspect is provided, comprising depositing a first layer of an electrically non-conductive material onto a substrate; depositing a first layer of an electrically conductive material onto the first layer of the electrically non-conductive material; depositing a second layer of electrically non-conductive material onto the first layer of electrically conductive material; depositing a second layer of electrically conductive material onto the second layer of electrically non-conductive material; depositing a third layer of electrically non-conductive material onto the second layer of electrically conductive material; depositing a third layer of electrically conductive material onto the third layer of electrically non-conductive material; depositing a fourth layer of electrically non-conductive material onto the third layer of electrically conductive material; and etching the deposited layers to form pores in the layers, at least some of the pores extending from an exterior surface of the electrically non-conductive material and contacting all three layers of electrically conductive material.

In an embodiment of the sixth aspect, at least one of the depositing steps comprises dip coating.

In an embodiment of the sixth aspect, at least one of the depositing steps comprises vapor deposition.

In an embodiment of the sixth aspect, at least one of the depositing steps comprises lamination.

In an embodiment of the sixth aspect, the method further comprises coating the pores' interior surfaces with an analyte membrane system, the analyte membrane system comprising at least one of a component that affects the analyte's rate of diffusion through the analyte membrane system and a component that reacts with the analyte to produce a species that electrochemically reacts at the surface of the electrically conductive material.

In an embodiment of the sixth aspect, coating comprises dip coating.

In an embodiment of the sixth aspect, coating comprises vapor deposition.

In a seventh aspect a method of manufacturing an analyte sensor according to the first aspect is provided, comprising depositing a first layer of an electrically conductive material onto a substrate; depositing a first layer of an electrically non-conductive material onto the first layer of electrically conductive material; depositing a second layer of electrically conductive material onto the first layer of electrically non-conductive material; depositing a second layer of electrically non-conductive material onto the second layer of electrically conductive material; depositing a third layer of electrically conductive material onto the second layer of electrically non-conductive material; and etching the deposited layers to form pores in the layers, at least some of the pores extending from an exterior surface of either the first or third layers of electrically conductive material and contacting the second layer of electrically conductive material and the other first or third layers of electrically conductive material.

In an embodiment of the seventh aspect, at least one of the depositing steps comprises dip coating.

In an embodiment of the seventh aspect, at least one of the depositing steps comprises vapor deposition.

In an embodiment of the seventh aspect, at least one of the depositing steps comprises lamination.

In an embodiment of the seventh aspect, at least one of the depositing steps comprises spin coating.

In an embodiment of the seventh aspect, the method further comprises coating the pores' interior surfaces with an analyte membrane system, the analyte membrane system comprising at least one of a component that affects the analyte's rate of diffusion through the analyte membrane system and a component that reacts with the analyte to produce a species that electrochemically reacts at the surface of the electrically conductive material.

In an embodiment of the seventh aspect, coating comprises dip coating.

In an embodiment of the seventh aspect, coating comprises vapor deposition.

BRIEF DESCRIPTION OF THE DRAWINGS

FIG. 9A depicts a schematic surface view of a sensing biointerface that includes a biointerface matrix surrounding a sensing mechanism.

FIG. 9B depicts a wire-like analyte sensing mechanism in one exemplary embodiment, which can be incorporated into the biointerface matrix to form the sensing biointerface.

DETAILED DESCRIPTION OF THE PREFERRED EMBODIMENT

Described herein are structures for use in implantable analyte sensors. The term "analyte" as used herein is a broad term, and is to be given its ordinary and customary meaning to a person of ordinary skill in the art (and is not to be limited to a special or customized meaning), and refers without limitation to a substance or chemical constituent in a biological fluid (e.g., blood, urine, extracellular fluid) that is intended to be analyzed. In one embodiment, the analyte is blood glucose. The term "detection" of an analyte as used herein is a broad term, and is to be given its ordinary and customary meaning to a person of ordinary skill in the art (and is not to be limited to a special or customized meaning), and refers without limitation to detecting the presence of an analyte and/or detecting the amount of an analyte present. In one embodiment, detection of an analyte provides a measure of the concentration of the analyte in a biological fluid.

Figure 1:
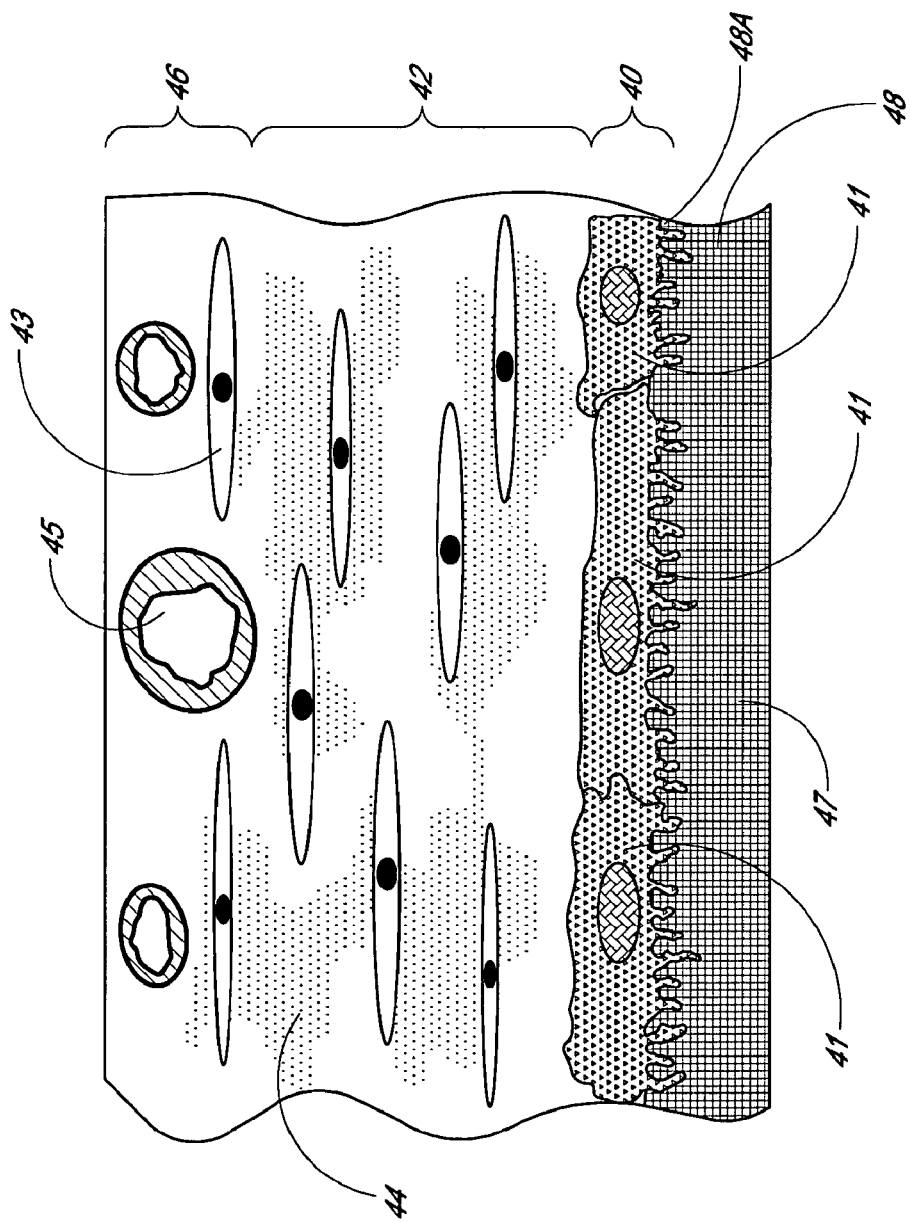
FIG. 1 depicts foreign body response near the surface of an implanted biosensor.
Figure 2:
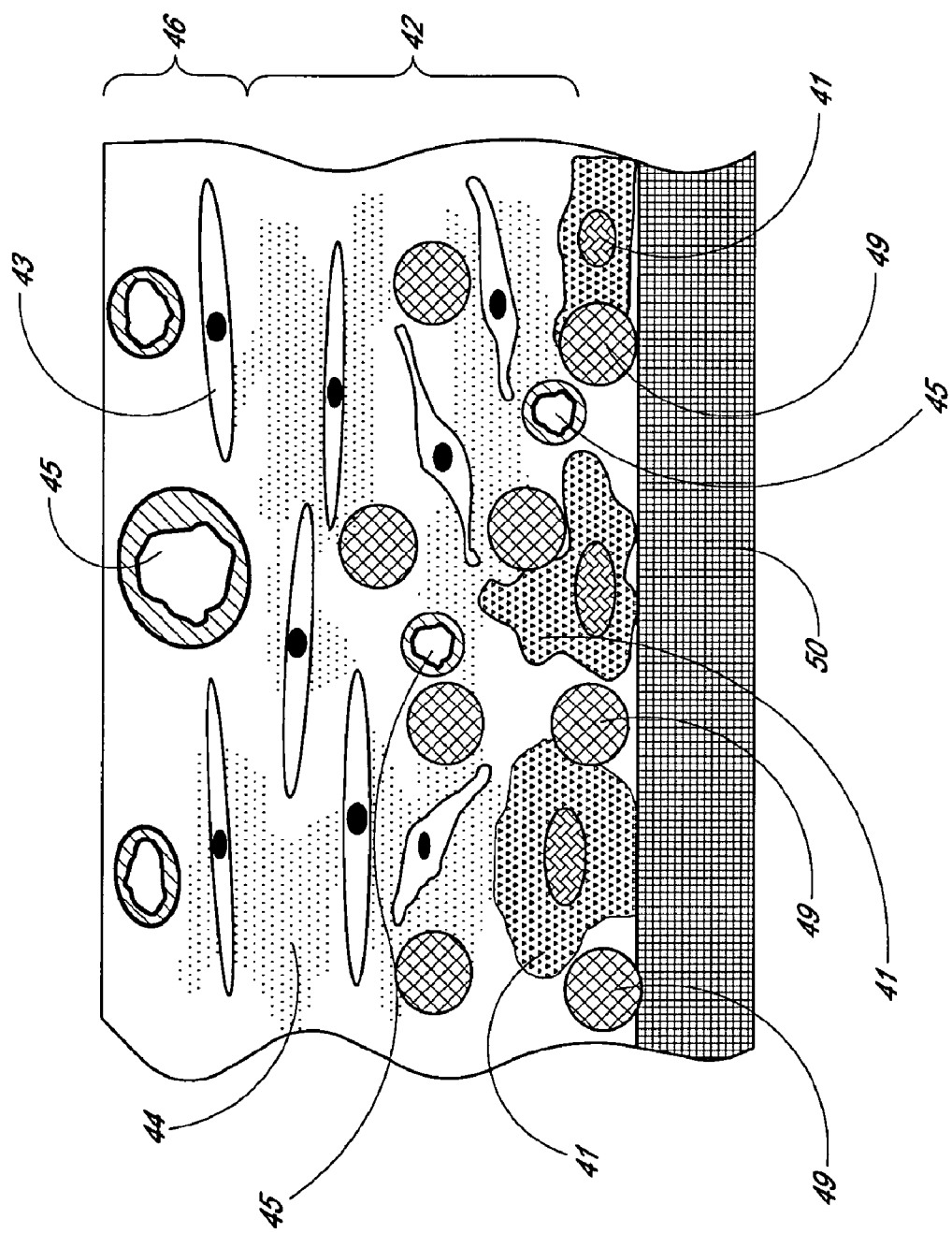
FIG. 2 depicts foreign body response near the surface of an implanted biosensor in the presence of a cell-disruptive biointerface.

One method of addressing foreign body response to implanted biosensors is illustrated in FIG. 2, which depicts FBR in the presence of a biointerface. The biointerface is constructed of a barrier cell disruptive material 49 that is incorporated on the surface of the biosensor 50. The material 49 disrupts the continuity of cells 41 so that an impermeable barrier cell layer does not form. All of the FBR cells and materials may be present, such as foreign body giant cells 41, fibroblasts 43, fibrous matrix 44, blood vessels 45, and connective granular tissue; however, orderly formation of the barrier cell, intermediate, and outer layers is inhibited. Thus, transport of the analyte to the sensor is not blocked and blood vessels can grow closer to the biosensor 50.

Figure 3:
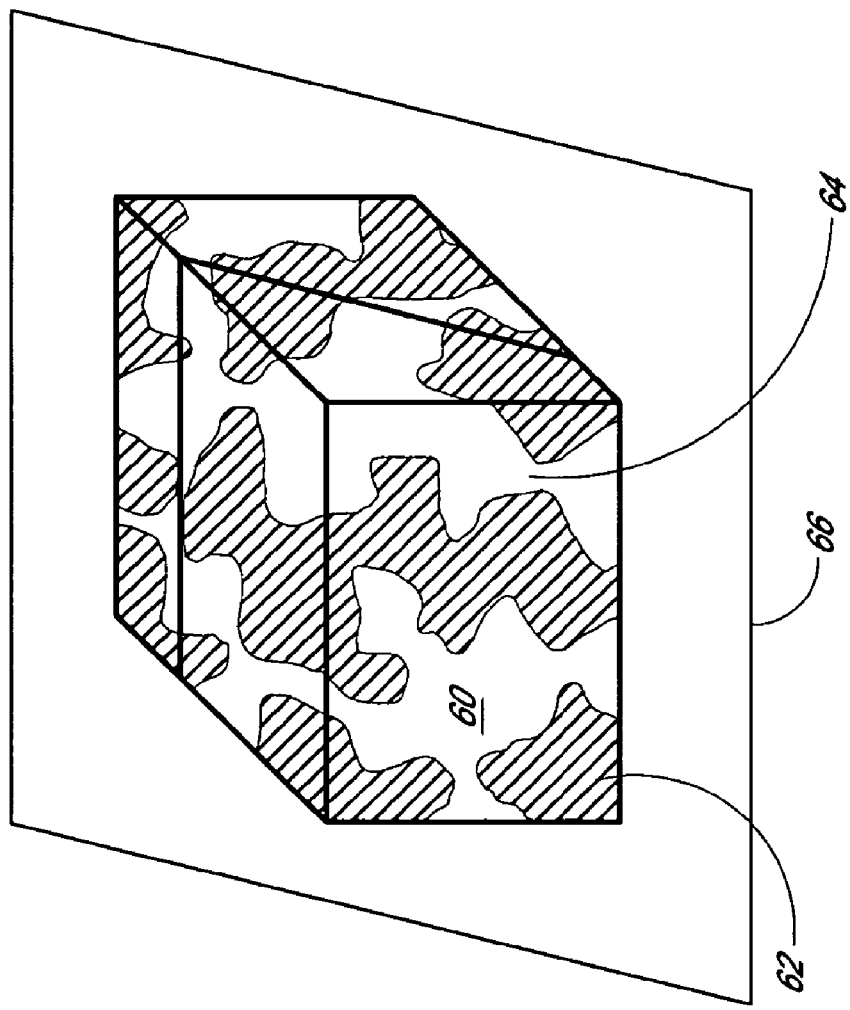
FIG. 3 depicts cell disruptive material comprising a solid matrix with cavities therein.

The biointerface comprising barrier cell disruptive material 49 may be constructed from non-woven fibers, such as illustrated in FIG. 2. Alternatively, the biointerface may be woven fiber mesh. FIG. 3 depicts another barrier cell disruptive layer 66. The barrier cell disruptive layer 66 consists of a solid material 62 in which cavities 64 are formed as depicted in FIG. 3. In order to ensure that the analyte can pass from the tissue side of the barrier cell disruptive layer 66 to the sensor side, it is advantageous that at least some cavities 64 extend uninterrupted from the tissue side to the sensor side.

Figure 4:
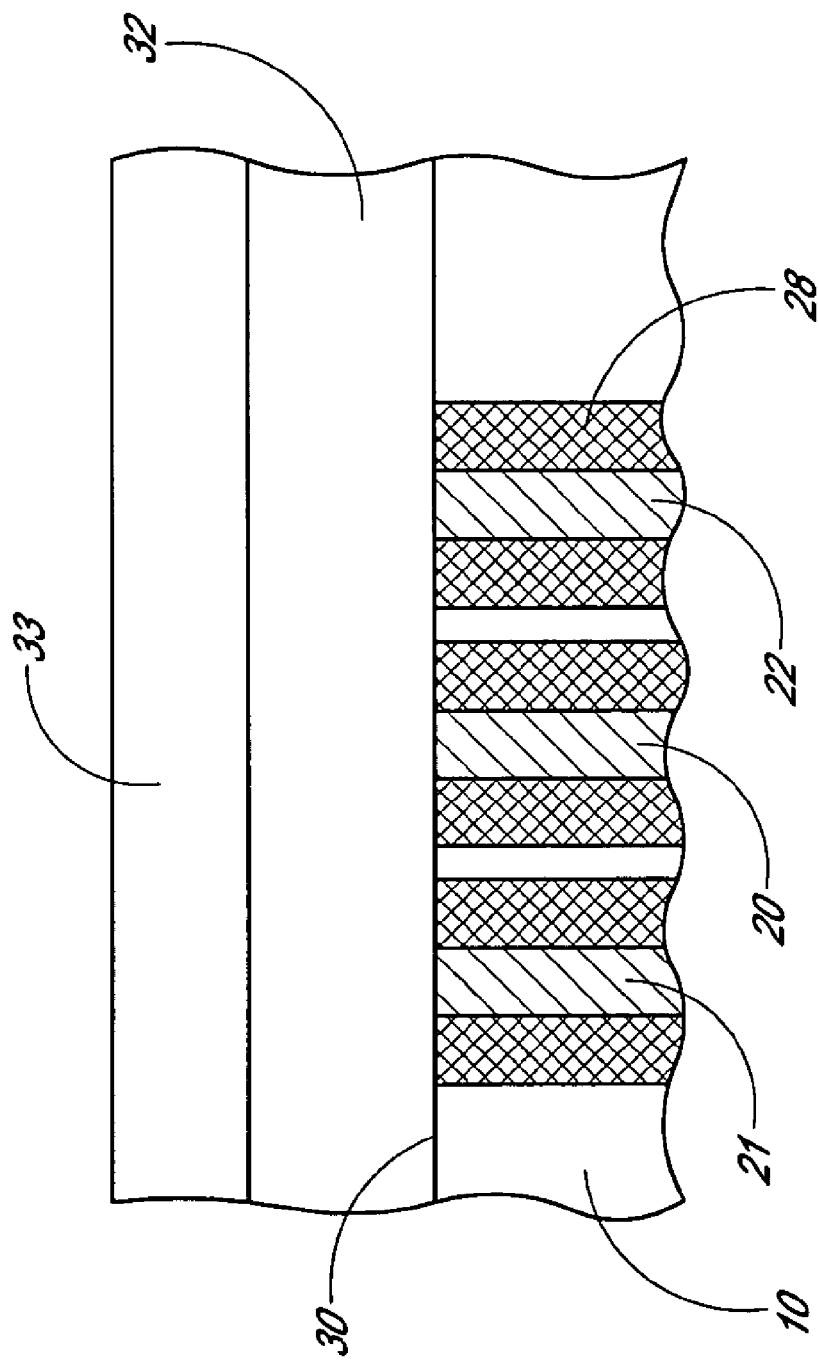
FIG. 4 depicts an implantable analyte sensor comprising a membrane system and a cell-disruptive biointerface.

FIG. 4 depicts an implantable analyte sensor configuration that makes use of a barrier cell disruptive biointerface 33. The sensor typically comprises a working electrode 21, a reference electrode 20, and an optional counter electrode 22. These electrodes may be insulated from each other by insulative layers 28 and further be housed in housing 10. The reference electrode 20 provides a stable-voltage electrode relative to which the voltage of the working electrode 21 can be controlled or detected. The optional counter electrode 22 draws the current flowing through the working electrode 20 so that the current through the reference electrode 20 is kept at a minimum, thus maintaining its voltage stability. The end surfaces of all three electrodes are advantageously coated with membrane system 32, which may comprise a layer of glucose oxidase enzyme. The membrane system 32 may then be coated with the barrier cell disruptive biointerface 33.

Biointerfaces for promoting tissue in-growth adjacent to a biosensor are described in more detail in U.S. Pat. No. 6,702,857, which is incorporated herein by reference in its entirety.

The Sensing Biointerface

Some embodiments of the present invention comprise combining the sensor electrodes and membrane system into the cell-disruptive biointerface (for example, a porous biointerface material). Thus, the cell-disruptive biointerface becomes a sensing biointerface. This combination may be embodied by providing an electrically non-conductive biocompatible matrix within which at least the working electrode can be incorporated, which together function as the biointerface. However, in some alternative embodiments, the biocompatible matrix comprises electrically conductive materials, for example, that function as a working electrode, without a requirement for a non-conductive material within the matrix. Passageways (e.g., interconnected pores or cavities) can be formed within the matrix or designed into the matrix to provide openings for FBR tissue in-growth near to the working electrode and provide analyte access to the working electrode.

The term "electrically non-conductive" material as used herein is a broad term, and is to be given its ordinary and customary meaning to a person of ordinary skill in the art (and is not to be limited to a special or customized meaning), and refers without limitation to material that allows no current or little current to flow under the voltages typically applied to the electrodes in biosensors. Non-limiting examples of electrically non-conductive materials include insulators such as plastics and other non-conductive polymers, non-conductive inorganics such as oxides, and semi-conductors exhibiting low conductivity such as un-doped silicon.

The term "electrically conductive" material as used herein is a broad term, and is to be given its ordinary and customary meaning to a person of ordinary skill in the art (and is not to be limited to a special or customized meaning), and refers without limitation to material through which readily detectable current flows under the voltages typically applied to the electrodes in biosensors. Non-limiting examples of electrically conductive material include metallic conductors, conductive polymers, and semi-conductors with appreciable conductivity.

Thus, some embodiments provide a porous biointerface, also referred to as a biointerface matrix, comprising a biocompatible matrix material wherein electroactive surfaces, with or without a membrane system coating, are distributed within at least some pores in the biointerface. In one embodiment, the sensing mechanism, being within the biointerface, includes a morphology substantially similar, complementary, or integral with the morphology of the cell disruptive biointerface, thereby enabling manipulation of the foreign body response to the sensing mechanism in a manner substantially similar to that of a porous biointerface material (e.g., cell-disruptive biointerface). While not wishing to be bound by theory, it is believed that by providing a sensing mechanism integrated throughout the biointerface, the cellular mechanisms of the foreign body response will not substantially attack or attempt to block the sensing mechanism as a foreign body as happens with conventional analyte sensors. A few exemplary embodiments are provided herein, however one skilled in the art will appreciate the variety of systems and methods that can be implemented in order to form the sensing biointerface described herein.

The biocompatible matrix, also referred to as biointerface matrix, can comprise a variety of porous structures. In one embodiment, the biocompatible matrix comprises a plurality of woven or non-woven fibers, one example of which is described with reference to FIGS. 5A to 5C. In another embodiment, the biocompatible matrix comprises a solid structure with interconnected pores or cavities formed therein, one example of which is described with reference to FIGS. 6A to 6C. In another example, the biocompatible matrix comprises a scaffolding defined by uniform or non-uniform mesh, wire, or fiber layers, formed with a through-porosity, one example of which is described with reference to FIGS. 8A and 8B.

In some embodiments, the interconnected cavities (also referred to as pores or passageways) are dimensioned such that fibrous matrix, blood vessels, fibroblasts, connective granular tissue, macrophages, and/or foreign body giant cells can migrate through or grow therein. In some embodiments, the interconnected cavities can be defined by one dimension (for example, shortest, average, or longest) of the cavity. In some embodiments, the dimensions can be defined by measuring techniques known in the art of porous materials (for example, bubble point test). It should be noted, that the term "nominal pore size" in the context of the biocompatible matrix in certain embodiments is derived from methods of analysis common to the membrane trade, such as the ability of the membrane to filter particles of a particular size, or the resistance of the membrane to the flow of fluids. It is noted, however that the term "nominal pore size" may not actually indicate the size or shape of the cavities, which in reality may have some degree of variability. Accordingly, in some embodiments, the term "nominal pore size" is a manufacturer's convention used to identify a particular membrane of a particular commercial source which can have a certain bubble point. One example of a bubble point measurement is described in Pharmaceutical Technology May 1983 pp. 36 to 42, which is incorporated herein by reference in its entirety.

In some embodiments, a substantial number of the cavities defined using any of the methods described above, are greater than or equal to about 20 microns in one dimension. In some other embodiments, a substantial number of the cavities are greater than or equal to about 30, 40, 50, 60, 70, 80, 90, 100, 120, 140, 160, 180, 200, 240, 280, 320, 360, 400, 500, 600, 700 microns in one dimension.

In some embodiments, a substantial number of the cavities, defined using any of the methods described above, are less than or equal to about 1000 microns in one dimension. In other embodiments, a substantial number of the cavities are less than or equal to about 900, 800, 700, 600, 500, 400, 360, 320, 280, 240, 200, 180, 160, 140, 120, 100 microns in one dimension.

In one alternative embodiment, wherein a substantial number of cavities are greater than or equal to about 20 microns in one dimension, there can be additional cavities that are less than or equal to about 20 microns in their shortest dimension interspersed therein. In another alternative embodiment, wherein a substantial number of cavities are greater than or equal to about 20 microns in one dimension, cavity dimensions can be gradually increased or decreased progressively through the layer, including some cavities that are less than or equal to about 20 microns in one dimension.

In some embodiments, the biocompatible matrix includes non-woven materials, woven materials, or other such materials, such that a porous structure is formed from the cavities between the fibers. In these embodiments, for example, the fibers are formed by structural elements that provide the three-dimensional conformation. Therefore in these embodiments, the biocompatible matrix may be defined by a fiber size of between about 1 and 100 microns in all but the longest dimension and a sufficient number of cavities of a size and structure to allow inflammatory cells (for example, macrophages) to completely enter therein through the apertures that define the cavities.

In some alternative embodiments, a bioactive agent is incorporated into the above described biocompatible matrix, which then diffuses out into the environment adjacent to the sensing region in order to modify the tissue response of the host to the device, for example, such as is described in U.S. Publication No. US-2005-0031689-A1. Additionally or alternately, a bioactive agent can be administered locally at the exit-site or implantation-site. Suitable bioactive agents are those that modify the host's tissue response to the sensor, for example anti-inflammatory agents, anti-infective agents, anesthetics, inflammatory agents, growth factors, immunosuppressive agents, antiplatelet agents, anti-coagulants, anti-proliferates, ACE inhibitors, cytotoxic agents, anti-barrier cell compounds, vascularization-inducing compounds, anti-sense molecules, or mixtures thereof, such as are described in more detail in co-pending U.S. Patent Publication No. US-2005-0031689-A1.

In embodiments wherein the biocompatible matrix is designed to enhance short-term (e.g., from about 1 to about 30 days) lifetime or performance of the sensor, a suitable bioactive agent can be chosen to ensure that tissue ingrowth does not substantially occur within the cavities of the biocompatible matrix. For example, by providing a tissue modifying bioactive agent, such as an anti-inflammatory agent (for example, Dexamethasone), substantial tissue ingrowth can be inhibited, at least in the short term, in order to maintain sufficient glucose transport through the pores of the biocompatible matrix to maintain a stable sensitivity.

In embodiments wherein the biocompatible matrix is designed to enhance long-term (e.g., from about a day to about a year or more) lifetime or performance of the sensor, a suitable bioactive agent, such as a vascularization-inducing compound or anti-barrier cell compound, can be chosen to encourage tissue ingrowth without barrier cell formation.

The architectures of the first and second domains may support vascularized tissue growth in or around the sensing biointerface, interfere with and resist barrier cell layer formation, and allow the transport of analytes through the porous biocompatible matrix to the sensing mechanism. However, certain outside influences, for example, faulty surgical techniques, acute or chronic movement of the implant, or other surgery-, patient-, and/or implantation site-related conditions, can create acute and/or chronic inflammation at the implant site. When this occurs, the sensing biointerface architecture alone may not be sufficient to overcome the acute and/or chronic inflammation. Accordingly, in some embodiments, the membrane architecture can benefit from additional mechanisms that aid in reducing this acute and/or chronic inflammation that can produce a barrier cell layer and/or a fibrotic capsule surrounding the implant, resulting in compromised solute transport through the membrane.

In general, the inflammatory response to biomaterial implants can be divided into two phases. The first phase consists of mobilization of mast cells and then infiltration of predominantly polymorphonuclear (PMN) cells. This phase is termed the acute inflammatory phase. Over the course of days to weeks, chronic cell types that comprise the second phase of inflammation replace the PMNs. Macrophage and lymphocyte cells predominate during this phase. While not wishing to be bound by any particular theory, it is believed that short-term stimulation of vascularization, or short-term inhibition of scar formation or barrier cell layer formation, provides protection from scar tissue formation, thereby providing a stable platform for sustained maintenance of the altered foreign body response.

Accordingly, bioactive intervention can modify the foreign body response in the early weeks of foreign body capsule formation, thereby fundamentally altering the long-term behavior of the foreign body capsule. Additionally, it is believed that the sensing biointerfaces of the preferred embodiments can advantageously benefit from bioactive intervention to overcome sensitivity of the membrane to implant procedure, motion of the implant, or other factors, which are known to otherwise cause inflammation, scar formation, and hinder device function in vivo.

In general, bioactive agents that are believed to modify tissue response include anti-inflammatory agents, anti-infective agents, anesthetics, inflammatory agents, growth factors, angiogenic (growth) factors, adjuvants, wound factors, resorbable device components, immunosuppressive agents, antiplatelet agents, anticoagulants, ACE inhibitors, cytotoxic agents, anti-barrier cell compounds, vascularization compounds, anti-sense molecules, and the like. In some embodiments, preferred bioactive agents include S1P (Sphingosine-1-phosphate), Monobutyrin, Cyclosporin A, Anti-thrombospondin-2, Rapamycin (and its derivatives), and Dexamethasone. However, other bioactive agents, biological materials (for example, proteins), or even non-bioactive substances can be preferred for incorporation into the membranes of preferred embodiments.

Bioactive agents suitable for use in the preferred embodiments are loosely organized into two groups: anti-barrier cell agents and vascularization agents. These designations reflect functions that are believed to provide short-term solute transport through the sensing biointerface, and additionally extend the life of a healthy vascular bed and hence solute transport through the sensing biointerface long term in vivo. However, not all bioactive agents can be clearly categorized into one or other of the above groups; rather, bioactive agents generally comprise one or more varying mechanisms for modifying tissue response and can be generally categorized into one or both of the above-cited categories.

Anti-Barrier Cell Agents

Generally, anti-barrier cell agents include compounds exhibiting affects on macrophages and foreign body giant cells (FBGCs). It is believed that anti-barrier cell agents prevent closure of the barrier to solute transport presented by macrophages and FBGCs at the device-tissue interface during FBC maturation.

Anti-barrier cell agents generally include mechanisms that inhibit foreign body giant cells and/or occlusive cell layers. For example, Super Oxide Dismutase (SOD) Mimetic, which utilizes a manganese catalytic center within a porphyrin like molecule to mimic native SOD and effectively remove superoxide for long periods, thereby inhibiting FBGC formation at the surfaces of biomaterials in vivo, may be incorporated into a sensing biointerface of a preferred embodiment.

Anti-barrier cell agents can include anti-inflammatory and/or immunosuppressive mechanisms that affect the wound healing process, for example, healing of the wound created by the incision into which an implantable device is inserted. Cyclosporine, which stimulates very high levels of neovascularization around biomaterials, can be incorporated into a sensing biointerface of a preferred embodiment [see U.S. Pat. No. 5,569,462 to Martinson et al., which is incorporated herein by reference in its entirety.] Alternatively, Dexamethasone, which abates the intensity of the FBC response at the tissue-device interface, can be incorporated into a sensing biointerface of a preferred embodiment. Alternatively, Rapamycin, which is a potent specific inhibitor of some macrophage inflammatory functions, can be incorporated into a sensing biointerface of a preferred embodiment.

Other suitable medicaments, pharmaceutical compositions, therapeutic agents, or other desirable substances can be incorporated into the membranes of preferred embodiments, including, but not limited to, anti-inflammatory agents, anti-infective agents, and anesthetics.

Generally, anti-inflammatory agents reduce acute and/or chronic inflammation adjacent to the implant, in order to decrease the formation of a FBC capsule to reduce or prevent barrier cell layer formation. Suitable anti-inflammatory agents include but are not limited to, for example, nonsteroidal anti-inflammatory drugs (NSAIDs) such as acetaminophen, aminosalicylic acid, aspirin, celecoxib, choline magnesium trisalicylate, diclofenac potassium, diclofenac sodium, diflunisal, etodolac, fenoprofen, flurbiprofen, ibuprofen, indomethacin, interleukin (IL)-10, IL-6 mutein, anti-IL-6 iNOS inhibitors (for example, L-NAME or L-NMDA), Interferon, ketoprofen, ketorolac, leflunomide, melenamic acid, mycophenolic acid, mizoribine, nabumetone, naproxen, naproxen sodium, oxaprozin, piroxicam, rofecoxib, salsalate, sulindac, and tolmetin; and corticosteroids such as cortisone, hydrocortisone, methylprednisolone, prednisone, prednisolone, betamethesone, beclomethasone dipropionate, budesonide, dexamethasone sodium phosphate, flunisolide, fluticasone propionate, paclitaxel, tacrolimus, tranilast, triamcinolone acetonide, betamethasone, fluocinolone, fluocinonide, betamethasone dipropionate, betamethasone valerate, desonide, desoximetasone, fluocinolone, triamcinolone, triamcinolone acetonide, clobetasol propionate, and dexamethasone.

Generally, immunosuppressive and/or immunomodulatory agents interfere directly with several key mechanisms necessary for involvement of different cellular elements in the inflammatory response. Suitable immunosuppressive and/or immunomodulatory agents include anti-proliferative, cell-cycle inhibitors, (for example, paclitaxel, cytochalasin D, infliximab), taxol, actinomycin, mitomycin, thospromote VEGF, estradiols, NO donors, QP-2, tacrolimus, tranilast, actinomycin, everolimus, methothrexate, mycophenolic acid, angiopeptin, vincristing, mitomycine, statins, C MYC antisense, sirolimus (and analogs), RestenASE, 2-chlorodeoxyadenosine, PCNA Ribozyme, batimstat, prolyl hydroxylase inhibitors, PPARγ ligands (for example troglitazone, rosiglitazone, pioglitazone), halofuginone, C-proteinase inhibitors, probucol, BCP671, EPC antibodies, catchins, glycating agents, endothelin inhibitors (for example, Ambrisentan, Tesosentan, Bosentan), Statins (for example, Cerivasttin), E. coli heat-labile enterotoxin, and advanced coatings.

Generally, anti-infective agents are substances capable of acting against infection by inhibiting the spread of an infectious agent or by killing the infectious agent outright, which can serve to reduce immuno-response without inflammatory response at the implant site. Anti-infective agents include, but are not limited to, anthelmintics (mebendazole), antibiotics including aminoclycosides (gentamicin, neomycin, tobramycin), antifungal antibiotics (amphotericin b, fluconazole, griseofulvin, itraconazole, ketoconazole, nystatin, micatin, tolnaftate), cephalosporins (cefaclor, cefazolin, cefotaxime, ceftazidime, ceftriaxone, cefuroxime, cephalexin), beta-lactam antibiotics (cefotetan, meropenem), chloramphenicol, macrolides (azithromycin, clarithromycin, erythromycin), penicillins (penicillin G sodium salt, amoxicillin, ampicillin, dicloxacillin, nafcillin, piperacillin, ticarcillin), tetracyclines (doxycycline, minocycline, tetracycline), bacitracin; clindamycin; colistimethate sodium; polymyxin b sulfate; vancomycin; antivirals including acyclovir, amantadine, didanosine, efavirenz, foscarnet, ganciclovir, indinavir, lamivudine, nelfinavir, ritonavir, saquinavir, silver, stavudine, valacyclovir, valganciclovir, zidovudine; quinolones (ciprofloxacin, levofloxacin); sulfonamides (sulfadiazine, sulfisoxazole); sulfones (dapsone); furazolidone; metronidazole; pentamidine; sulfanilamidum crystallinum; gatifloxacin; and sulfamethoxazole/trimethoprim.

Vascularization Agents

Generally, vascularization agents include substances with direct or indirect angiogenic properties. In some cases, vascularization agents may additionally affect formation of barrier cells in vivo. By indirect angiogenesis, it is meant that the angiogenesis can be mediated through inflammatory or immune stimulatory pathways. It is not fully known how agents that induce local vascularization indirectly inhibit barrier-cell formation; however it is believed that some barrier-cell effects can result indirectly from the effects of vascularization agents.

Vascularization agents include mechanisms that promote neovascularization and accelerate wound healing around the membrane and/or minimize periods of ischemia by increasing vascularization close to the tissue-device interface. Sphingosine-1-Phosphate (S1P), which is a phospholipid possessing potent angiogenic activity, is incorporated into a sensing biointerface of a preferred embodiment. Monobutyrin, which is a potent vasodilator and angiogenic lipid product of adipocytes, is incorporated into a sensing biointerface of a preferred embodiment. In another embodiment, an anti-sense molecule (for example, thrombospondin-2 anti-sense), which increases vascularization, is incorporated into a sensing biointerface.

Vascularization agents can include mechanisms that promote inflammation, which is believed to cause accelerated neovascularization and wound healing in vivo. In one embodiment, a xenogenic carrier, for example, bovine collagen, which by its foreign nature invokes an immune response, stimulates neovascularization, and is incorporated into a sensing biointerface of the preferred embodiments. In another embodiment, Lipopolysaccharide, which is a potent immunostimulant, is incorporated into a sensing biointerface. In another embodiment, a protein, for example, a bone morphogenetic protein (BMP), which is known to modulate bone healing in tissue, is incorporated into a sensing biointerface of a preferred embodiment.

Generally, angiogenic agents are substances capable of stimulating neovascularization, which can accelerate and sustain the development of a vascularized tissue bed at the tissue-device interface. Angiogenic agents include, but are not limited to, Basic Fibroblast Growth Factor (bFGF), (also known as Heparin Binding Growth Factor-II and Fibroblast Growth Factor II), Acidic Fibroblast Growth Factor (aFGF), (also known as Heparin Binding Growth Factor-I and Fibroblast Growth Factor-I), Vascular Endothelial Growth Factor (VEGF), Platelet Derived Endothelial Cell Growth Factor BB (PDEGF-BB), Angiopoietin-1, Transforming Growth Factor Beta (TGF-Beta), Transforming Growth Factor Alpha (TGF-Alpha), Hepatocyte Growth Factor, Tumor Necrosis Factor-Alpha (TNF-Alpha), Placental Growth Factor (PLGF), Angiogenin, Interleukin-8 (IL-8), Hypoxia Inducible Factor-I (HIF-1), Angiotensin-Converting Enzyme (ACE) Inhibitor Quinaprilat, Angiotropin, Thrombospondin, Peptide KGHK, Low Oxygen Tension, Lactic Acid, Insulin, Copper Sulphate, Estradiol, prostaglandins, cox inhibitors, endothelial cell binding agents (for example, decorin or vimentin), glenipin, hydrogen peroxide, nicotine, and Growth Hormone.

Generally, pro-inflammatory agents are substances capable of stimulating an immune response in host tissue, which can accelerate or sustain formation of a mature vascularized tissue bed. For example, pro-inflammatory agents are generally irritants or other substances that induce chronic inflammation and chronic granular response at the wound-site. While not wishing to be bound by theory, it is believed that formation of high tissue granulation induces formation of blood vessels, which supply an adequate or rich supply of analytes to the device-tissue interface. Pro-inflammatory agents include, but are not limited to, xenogenic carriers, Lipopolysaccharides, S. aureus peptidoglycan, and proteins.

Other substances that can be incorporated into membranes of preferred embodiments include various pharmacological agents, excipients, and other substances well known in the art of pharmaceutical formulations.

Bioactive Agent Delivery Systems and Methods

There are a variety of systems and methods by which the bioactive agent may be incorporated into the sensing biointerface of the preferred embodiments. In some embodiments, the bioactive agent is incorporated at the time of manufacture of the sensing biointerface. For example, the bioactive agent can be blended into any of the membrane and/or biointerface materials prior to curing, or subsequent to their manufacture, for example, by coating, imbibing, solvent-casting, or sorption of the bioactive agent into the sensing biointerface. Although the bioactive agent is preferably incorporated into the sensing biointerface, in some embodiments the bioactive agent can be administered concurrently with, prior to, or after implantation of the device systemically, for example, by oral administration, or locally, for example, by subcutaneous injection near the implantation site. In some embodiments, a combination of bioactive agent(s) incorporated in the sensing biointerface and bioactive agent(s) administration locally and/or systemically is used.

In embodiments wherein the sensing biointerface of the preferred embodiments include a bioactive agent, the bioactive agent can be incorporated into numerous aspects of the device, including electrically conductive or non-conductive portions, insulator or membrane materials, and/or other materials that form the biointerface. In some embodiments, the bioactive agent is sprinkled or sprayed on the surface of the device, for example, using known deposition techniques.

The bioactive agent can include a carrier matrix, wherein the matrix includes one or more of collagen, a particulate matrix, a resorbable or non-resorbable matrix, a controlled-release matrix, and/or a gel. In some embodiments, the carrier matrix includes a reservoir, wherein a bioactive agent is encapsulated within a microcapsule. The carrier matrix can include a system in which a bioactive agent is physically entrapped within a polymer network. In some embodiments, the bioactive agent is cross-linked with certain materials of the sensing biointerface, while in others the bioactive agent is sorbed into the materials, for example, by adsorption, absorption, or imbibing. The bioactive agent can be deposited in or on the sensing biointerface, for example, by coating, filling, or solvent casting. In certain embodiments, ionic and nonionic surfactants, detergents, micelles, emulsifiers, demulsifiers, stabilizers, aqueous and oleaginous carriers, solvents, preservatives, antioxidants, or buffering agents are used to incorporate the bioactive agent into the sensing biointerface. The bioactive agent can be incorporated into a polymer using techniques such as described above, and the polymer can be used to form the sensing biointerface, coatings on the sensing biointerface, portions of the sensing biointerface, and/or a portion of an implantable device.

The sensing biointerface can be manufactured using techniques such as described here and/or as are known in the art. The bioactive agent can be sorbed into the sensing biointerface, for example, by soaking the sensing biointerface for a length of time (for example, from about an hour or less to about a week or more, preferably from about 4, 8, 12, 16, or 20 hours to about 1, 2, 3, 4, 5, or 7 days).

The bioactive agent can be blended into uncured polymer prior to forming the sensing biointerface (or a portion thereof). The sensing biointerface (or a portion thereof) is then cured and the bioactive agent thereby cross-linked and/or encapsulated within the polymer that forms the sensing biointerface (or a portion thereof). For example, Monobutyrin was covalently bonded to a silicone matrix in such a manner that is slowly cleavable under in vivo conditions. The alcohol groups of Monobutyrin react with a silanol group, resulting in a C—O—Si bond. This bond is known to be susceptible to hydrolysis, and is therefore cleaved to yield the original alcohol and silanol. Thus, the Monobutyrin is released from the silicone matrix according to the rate of hydrolysis. Other bioactive agents, such as Dexamethasone, comprise alcohol groups and can be bound to a silicone matrix in a similar manner.

In yet another embodiment, microspheres are used to encapsulate the bioactive agent. The microspheres can be formed of biodegradable polymers, most preferably synthetic polymers or natural polymers such as proteins and polysaccharides. In this context, the term polymer is used to refer to both to synthetic polymers and proteins. U.S. Pat. No. 6,281,015, which is incorporated herein by reference in its entirety, discloses some systems and methods that can be used in conjunction with the preferred embodiments. In general, bioactive agents can be incorporated in (1) the polymer matrix forming the microspheres, (2) microparticle(s) surrounded by the polymer which forms the microspheres, (3) a polymer core within a protein microsphere, (4) a polymer coating around a polymer microsphere, (5) mixed in with microspheres aggregated into a larger form, or (6) a combination thereof. Bioactive agents can be incorporated as particulates or by co-dissolving the factors with the polymer. Stabilizers can be incorporated by addition of the stabilizers to the factor solution prior to formation of the microspheres.

The bioactive agent can be incorporated into a hydrogel and coated or otherwise deposited in or on the sensing biointerface. Some hydrogels suitable for use in the preferred embodiments include cross-linked, hydrophilic, three-dimensional polymer networks that are highly permeable to the bioactive agent and are triggered to release the bioactive agent based upon exposure to a stimulus.

The bioactive agent can be incorporated into the sensing biointerface by solvent casting, wherein a solution including dissolved bioactive agent is disposed on the surface of the sensing biointerface, after which the solvent is removed to form a coating on the membrane surface.

In yet another embodiment, the interconnected cavities of the sensing biointerface are filled with the bioactive agent. Preferably, a bioactive agent, with or without a carrier matrix, fills the cavities of the membrane, depending on the loading and release properties desired, which are discussed in more detail below.

Short-term release of the bioactive agent in the preferred embodiments generally refers to release over a period of from about 1 day or less to about 2, 3, 4, 5, 6, or 7 days, 2 or 3 weeks, 1 month, or more. More preferably, the short-term release of the bioactive agent occurs over from about 14, 15, 16, 17, or 18 days up to about 19, 20, or 21 days.

Some devices, such as implantable analyte measuring-devices, drug delivery devices, and cell transplantation devices, that require transport of solutes across the device-tissue interface for proper function, tend to lose their function after the first few days following implantation. At least one reason for this loss of function is the lack of direct contact with circulating fluid for appropriate analyte transport to the device. Therefore, in some embodiments, short-term release of certain bioactive agents, for example vascularization agents, can increase the circulating fluid to the device for an extended period of time.

Additionally, it is believed that short-term release of the bioactive agent can have a positive effect of the functionality of porous sensing biointerface during the initial tissue ingrowth period prior to formation of a capillary bed. For example, when a device requiring analyte transport across its device-tissue interface is implanted, a "sleep period" can occur which begins as early as the first day after implantation and extends as far as one month after implantation. However shorter sleep periods are more common. During this sleep period, extensive ingrowth of tissue into the porous structure causes the inflammatory cells responsible for facilitating wound healing to proliferate within the local environment of the wound region. Because these cells are respiring, they consume some or all of the analyte (e.g., glucose) and oxygen that is within the wound environment, which has been shown to block adequate flow of analytes to the implantable device. Accordingly in some embodiments, it is believed that short-term release of certain bioactive agents, for example vascularization agents, can aid in providing adequate vascularization to substantially overcome the effects of the sleep period, and thereby allow sufficient analytes to pass through to the implantable device.

Additionally, it is believed that short-term release of the bioactive agent can have an enhanced effect on neovascularization at the tissue-device interface. Although neovascularization alone is generally not sufficient to provide sufficient analyte transport at the device-tissue interface, in combination with other mechanisms, enhanced neovascularization can result in enhanced transport of analytes from the host to the implanted device. Therefore in some embodiments, short-term release of certain bioactive agents, for example angiogenic agents, can have a positive effect on neovascularization and thereby enhance transport of analytes at the device-tissue interface.

Additionally, it is believed that short-term release of the bioactive agent may be sufficient to reduce or prevent barrier cell layer formation. Formation of a cohesive monolayer of closely opposed cells, e.g., macrophages and foreign body giant cells, interfere with the transport of analytes across the tissue-device interface, also known as a barrier cell layer, and are large contributors to poor device performance. See U.S. Pat. No. 6,702,857, which is incorporated herein by reference in its entirety. Therefore in some embodiments, it is believed that short-term release of certain bioactive agents, for example, anti-barrier cell agents, can aid in preventing barrier cell layer formation.

Additionally, it is believed that short-term release of the bioactive agent may be sufficient to prevent negative effects of acute inflammation caused, for example, by surgical trauma, micro-motion, or macro-motion of the device in the soft tissue. Short-term release of anti-inflammatory agents may be sufficient to rescue a sensing biointerface from the negative effects associated with such acute inflammation, rendering adequate analyte transport.

Long-term release of the bioactive agent in the preferred embodiments generally occurs over a period of from about 1 month to about 2 years or more, preferably from at least about 2 months to at least about 13, 14, 15, 16, 17, 18, 19, 20, 21, 22, or 23 months, and more preferably from at least about 3 months to at least about 4, 5, 6, 7, 8, 9, 10, 11, or 12 months.

Long-term glucose-measuring device experiments demonstrate that many biointerface materials experience a distinct and continual decline in sensitivity, for example, reduced analyte transport, beginning at three months after implantation in some cases. It is believed that this decline in analyte transport can be a result of barrier cell layer formation, cellular growth at the membrane, and/or thickening of the fibrous elements of the foreign body capsule. Other contributing factors can include chronic inflammation, which is believed to be due to micro-motion or macro-motion of the device; delamination of the sensing biointerface, which is believed to be due to cellular ingrowth within and under the sensing biointerface; compression of the sensing biointerface due to increasing compression of the foreign body capsule around the device; and distortion of the sensing biointerface, which is believed to be a result of a combination of compression and cellular ingrowth, for example.

Accordingly, long-term release of certain bioactive agents can modulate the foreign body response sufficiently to prevent long-term thickening of the foreign body capsule, reduce or prevent barrier cell layer formation, reduce or prevent chronic inflammation, reduce or prevent extensive cellular ingrowth, and/or reduce or prevent compression of the foreign body capsule on the sensing biointerface.

Loading of Bioactive Agents

The amount of loading of the bioactive agent into the sensing biointerface can depend upon several factors. For example, the bioactive agent dosage and duration can vary with the intended use of the sensing biointerface, for example, cell transplantation, analyte measuring-device, and the like; differences among patients in the effective dose of bioactive agent; location and methods of loading the bioactive agent; and release rates associated with bioactive agents and optionally their carrier matrix. Therefore, one skilled in the art will appreciate the variability in the levels of loading the bioactive agent, for the reasons described above.

In some embodiments, wherein the bioactive agent is incorporated into the sensing biointerface without a carrier matrix, the preferred level of loading of the bioactive agent into the sensing biointerface can vary depending upon the nature of the bioactive agent. The level of loading of the bioactive agent is preferably sufficiently high such that a biological effect is observed. Above this threshold, bioactive agent can be loaded into the sensing biointerface so as to imbibe up to 100% of the solid portions, cover all accessible surfaces of the membrane, and/or fill up to 100% of the accessible cavity space. Typically, the level of loading (based on the weight of bioactive agent(s), sensing biointerface, and other substances present) is from about 1 ppm or less to about 1000 ppm or more, preferably from about 2, 3, 4, or 5 ppm up to about 10, 25, 50, 75, 100, 200, 300, 400, 500, 600, 700, 800, or 900 ppm. In certain embodiments, the level of loading can be 1 wt. % or less up to about 50 wt. % or more, preferably from about 2, 3, 4, 5, 6, 7, 8, 9, 10, 15, or 20 wt. % up to about 25, 30, 35, 40, or 45 wt. %.

When the bioactive agent is incorporated into the sensing biointerface with a carrier matrix, such as a gel, the gel concentration can be optimized, for example, loaded with one or more test loadings of the bioactive agent. It is generally preferred that the gel contain from about 0.1 or less to about 50 wt. % or more of the bioactive agent(s), preferably from about 0.2, 0.3, 0.4, 0.5, 0.6, 0.7, 0.8, or 0.9 wt. % to about 6, 7, 8, 9, 10, 15, 20, 25, 30, 35, 40, or 45 wt. % or more bioactive agent(s), more preferably from about 1, 2, or 3 wt. % to about 4 or 5 wt. % of the bioactive agent(s). Substances that are not bioactive can also be incorporated into the matrix.

Referring now to microencapsulated bioactive agents, the release of the agents from these polymeric systems generally occurs by two different mechanisms. The bioactive agent can be released by diffusion through aqueous filled channels generated in the dosage form by the dissolution of the agent or by voids created by the removal of the polymer solvent or a pore forming agent during the original micro-encapsulation. Alternatively, release can be enhanced due to the degradation of the polymer. With time, the polymer erodes and generates increased porosity and microstructure within the device. This creates additional pathways for release of the bioactive agent.

Sensing Biointerface Based Sensors

Generally, the sensor electrodes comprise at least one working electrode incorporated into the biocompatible matrix. In some embodiments, at least one reference electrode is incorporated into the biocompatible matrix; however it is possible that the reference electrode exists at a location other than within the biocompatible matrix. In some embodiments, a counter electrode is incorporated into the biocompatible matrix, however it is possible that the counter electrode exists at a location other than within the biocompatible matrix or does not exist at all.

Figure 5A:
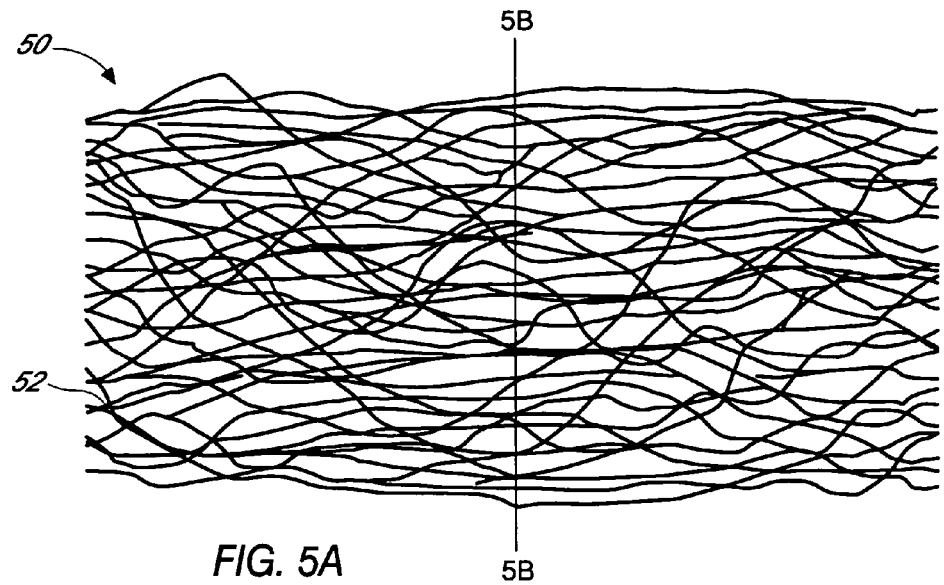
FIG. 5A depicts a side schematic view of a sensing biointerface that incorporates electrodes within fibers.

FIG. 5A is a schematic surface view of a sensing biointerface in one embodiment, wherein a biocompatible matrix is formed from a plurality of fibers formed into a porous biointerface structure 50. In this embodiment, the plurality of fibers that form the biocompatible matrix 50 include at least some fibers formed from an electrode material surrounded by a membrane system (also referred to as an electrode-membrane fiber), which fibers are configured to measure an analyte. In some embodiments, all of the fibers of the biocompatible matrix are electrode-membrane fibers, however in some alternative embodiments some portion of the fibers that form the biocompatible matrix may be formed from insulating materials or other non-conductive materials. Furthermore, in some embodiments, fibers may be present that comprise an electrode material that is exposed directly to the cavities between the fibers without a membrane coating.

In the illustrated embodiment, the fibers are formed into a non-woven fiber matrix, which is generally manufactured by interlocking or bonding a plurality of fibers together. In some alternative embodiments, the sensing biointerface can be formed into a woven fiber matrix, which is generally manufactured by weaving the fibers together. In some other alternative embodiments, the sensing biointerface can be formed into a uniform or non-uniform scaffolding, which is generally manufactured by bonding an array of fibers together.

Figure 5B:
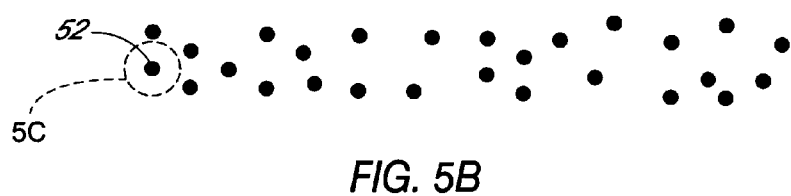
FIG. 5B depicts a cross-sectional view through line 5B-5B of FIG. 5A showing some fibers that form the biointerface in the embodiment of FIG. 5A.

FIG. 5B is a cross-sectional view taken along line 5B-5B of FIG. 5A, showing a plurality of electrode-membrane fibers 52 in cross-section. In this embodiment, at least one working electrode 54 may be provided, wherein the working electrode 54 may be surrounded by a multi-layer membrane system. In some embodiments, the biocompatible matrix comprises a plurality of working, reference, and/or counter electrodes, some or all of which may be electrode-membrane fibers. However, not all embodiments include a membrane system and/or electrode cores in some or all of the fibers. Generally, the biocompatible matrix comprises between about 1, 2, 3, 4, 5, 6, 7, 8, 9, or 10% to about 20, 30, 40, 50, 60, 70, 80, 90, or 100% of its fibers with an electrode core. Although FIG. 5B depicts an electrode-membrane fiber 52 near the periphery of the fiber bundle, those of skill in the art will appreciate that such electrode-membrane fibers may be located at any location within the fiber bundle. For example, in some embodiments, electrode-membrane fibers are located at a central position within the fiber bundle.

Figure 5C:
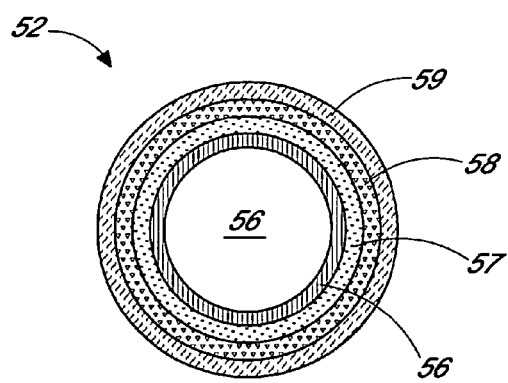
FIG. 5C depicts a cross-sectional expanded view of one fiber shown in FIG. 5B, showing an electrode surrounded by a membrane system.

FIG. 5C is an expanded view of one of the electrode-membrane fibers 52 of FIG. 5B in cross-section, showing the membrane system surrounding the fiber. The electrode-membrane fiber comprises a core formed from an electrode material (e.g. working electrode 54). In some embodiments, the electrode core comprises a wire or other bulk metal formed into an appropriate size and shape. Alternatively, the electrode core comprises a substrate onto which the electrode material is deposited utilizing techniques known in the art, for example, thin or thick film techniques. Preferably, the electrode core comprises any suitable conductive material, for example gold, silver, platinum, palladium, iridium, lead, conducting polymers, or other non-metal electrodes such as graphite or other carbon materials.

In general, the membrane system functions to control the flux of a biological fluid therethrough and/or to protect sensitive regions of the sensor from contamination by the biological fluid, for example. Some conventional electrochemical enzyme-based analyte sensors generally include a membrane system that controls the flux of the analyte being measured, protects the electrodes from contamination of the biological fluid, and/or provides an enzyme that catalyzes the reaction of the analyte with a co-factor, for example. See, e.g., co-pending U.S. patent application Ser. No. 10/838,912, filed May 3, 2004 entitled "IMPLANTABLE ANALYTE SENSOR," U.S. patent application Ser. No. 11/077,715, filed Mar. 10, 2005 and entitled "TRANSCUTANEOUS ANALYTE SENSOR," and U.S. patent application Ser. No. 11/360,819, filed Feb. 22, 2006 entitled "ANALYTE SENSOR," all of which are incorporated herein by reference in their entirety.

The membrane systems of the preferred embodiments can include any membrane configuration suitable for use with any analyte sensor (such as described in more detail above). In general, the membrane systems of the preferred embodiments include a plurality of domains, all or some of which can be adhered to or deposited on the analyte sensor as is appreciated by one skilled in the art. In one embodiment, the membrane system generally provides one or more of the following functions: 1) protection of the exposed electrode surface from the biological environment, 2) diffusion resistance (limitation) of the analyte, 3) a catalyst for enabling an enzymatic reaction, 4) limitation or blocking of interfering species, and 5) hydrophilicity at the electrochemically reactive surfaces of the sensor interface, such as described in more detail in co-pending U.S. patent application Ser. No. 10/838,912, filed May 3, 2004 entitled "IMPLANTABLE ANALYTE SENSOR," U.S. patent application Ser. No. 11/077,715, filed Mar. 10, 2005 and entitled "TRANSCUTANEOUS ANALYTE SENSOR," and U.S. patent application Ser. No. 11/360,250, filed Feb. 22, 2006, and entitled "ANALYTE SENSOR", all of which are incorporated herein by reference in their entirety. Accordingly, in one embodiment, the membrane system include a plurality of domains or layers, for example, an electrode (or electrolyte) domain 56, an interference domain 57, an enzyme domain 58, and a resistance domain 59, and may include additional domains, such as a bioprotective domain, a cell impermeable domain, and/or an oxygen domain (not shown), such as described in more detail in the above-cited co-pending U.S. Patent Applications and below. However, it is understood that a membrane system modified for other sensors, for example, by including fewer or additional domains is within the scope of the preferred embodiments.

Figure 10:
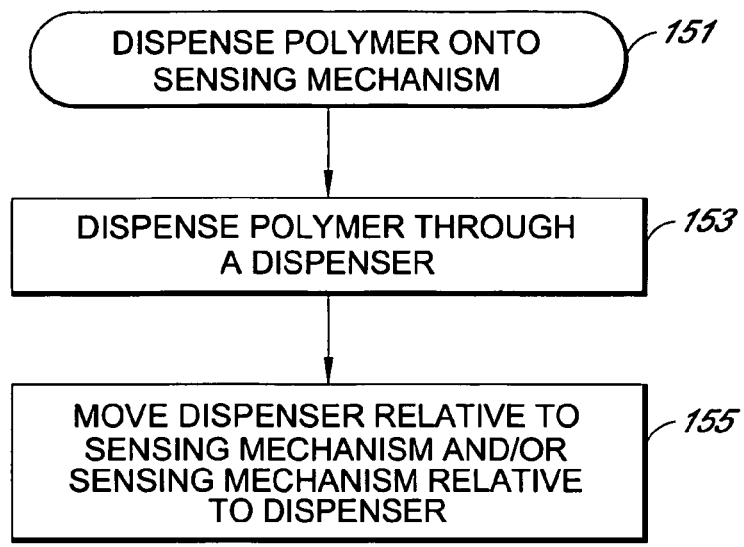
FIG. 10 is a flow chart that illustrates a process of dispensing a fibrous biointerface matrix onto a sensing mechanism.

In one example of a glucose sensor, one or more working electrode-membrane fibers, one or more reference electrode fibers, and one or more counter electrode fibers are formed into a non-woven biocompatible matrix. The matrix is connected to appropriate electronics (e.g., as shown in FIG. 10) and implanted in a host. The connection between the electrodes and electronics may be accomplished by electrically coupling each electrode within each electrode-containing fiber with the electronics. For example, in one embodiment, each working electrode 54 is electrically coupled, such as by spot welding or other suitable technique, to a single electrical contact, which is then coupled to the sensing electronics. Over time, as the host's tissue grows in and through the passageways of the biocompatible matrix, a mature bed of vascularized tissue will form, enabling long term measurement of the analyte in vivo. While not wishing to be bound by theory, it is believed that the host response to a sensing biointerface of the preferred embodiments will enable long term measurement of an analyte due to tissue ingrowth into and through the passageways of the porous biocompatible matrix. It is noted, however, that measurement of the analyte prior to tissue ingrowth is also possible and/or with the incorporation of bioactive agents can be manipulated for a variety of lengths and/or time periods.

Figure 6A:
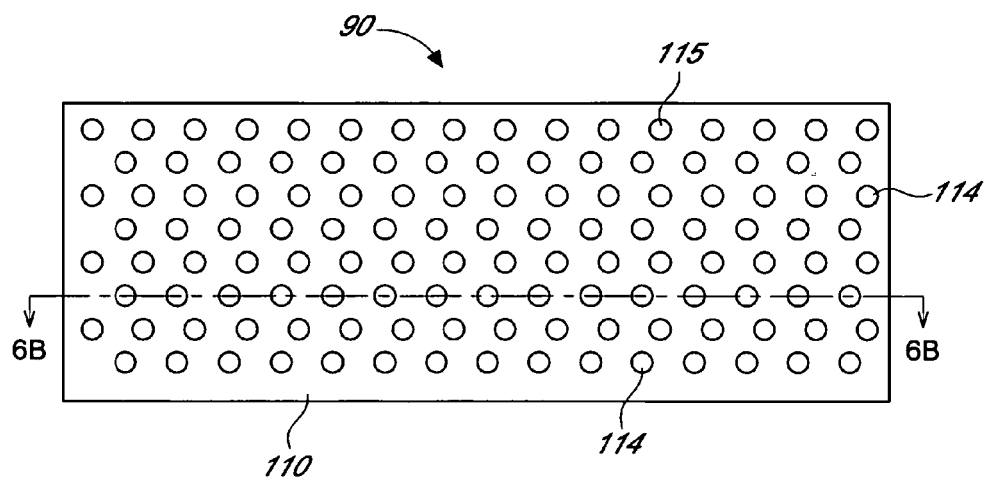
FIG. 6A depicts a schematic surface view of a sensing cell-disruptive biointerface that comprises pores and incorporates electrodes within the biointerface.

FIG. 6A depicts a schematic surface view of a sensing cell-disruptive biointerface 90 that incorporates electrodes as part of the biointerface in an alternative embodiment. In this embodiment, openings 115 are shown on the surface of the biointerface that provide access to pores within the through-porous biointerface. Openings 115 may be formed on all sides of the biointerface. In some embodiments, the openings and pores are formed into the biointerface by drilling or etching (e.g., laser drilling or photolithography), which is described in more detail below.

Figure 6B:
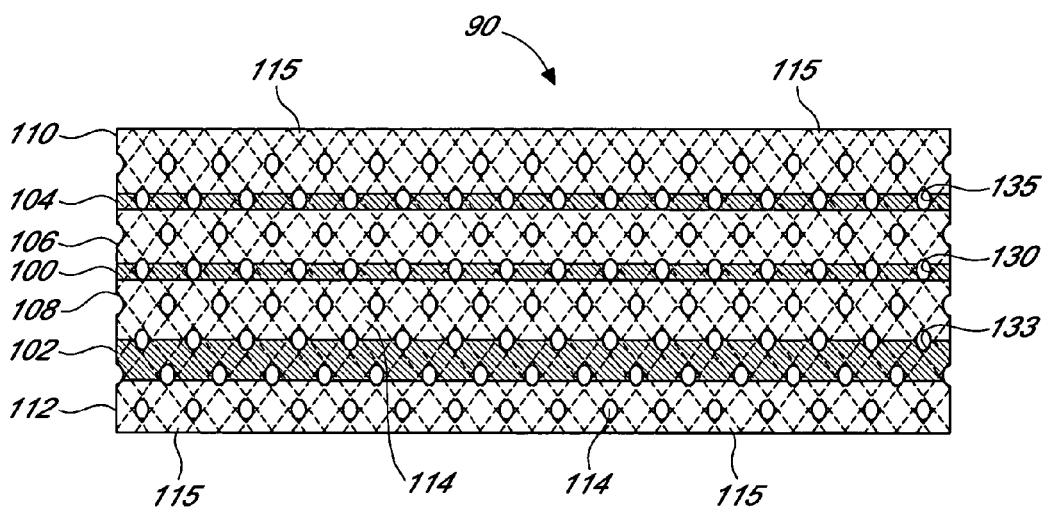
FIG. 6B depicts a cross-sectional view through line 6B-6B of FIG. 6A, showing the through porosity of the biointerface.

FIG. 6B depicts a cross-sectional view through line 6B-6B of FIG. 6A showing the through-porosity of the biointerface. In this embodiment, the biointerface 90 includes a sheet having multiple layers, for example, alternating non-conductive and conductive layers. Conductive layer 100 is the working electrode, conductive layer 102 is the counter electrode, and conductive layer 104 is the reference electrode. The working electrode 100 is separated from the counter electrode 102 and reference electrode 104 by non-conductive layers 106 and 108. The counter electrode 102 and reference electrode 104 are separated from tissue surrounding the implant by non-conductive layers 110 and 112. Because the electrodes 100, 102, and 104 are incorporated within the biointerface 90 rather than being adjacent to it as depicted in FIG. 4, the biointerface 90 may contact body tissue on both sides. In other words, both non-conductive layers 110 and 112 will be in contact with surrounding body tissue.

Non-limiting examples of material that may be used for non-conductive layers 106, 108, 110, and 112 include polytetrafluoroethylene, polyethylene-co-tetrafluoroethylene, polyurethanes, block copolymers, and silicone.

In some embodiments, the working electrode 100 and the counter electrode 102 are constructed from platinum. The counter electrode 102 advantageously has low impedance. Thus, in some embodiments, the counter electrode 102 has an exposed surface area (e.g., surface area exposed to the inside surface of pores 114) at least several fold greater than the exposed surface area of the working electrode 100. In some embodiments, the reference electrode 104 is a silver/silver chloride reference electrode (e.g., it consists of a layer of silver and an adjacent layer of silver chloride).

The sensing biointerface 90 advantageously has the form of a thin membrane. In one embodiment, the biointerface 90 is approximately 300 microns thick.

A plurality of pores 114 extend throughout biointerface 90. The size of pores 114 are such that tissue may grow into the pores during the body's FBR response. However, the size and distribution of the pores 114 are sufficient to disrupt the continuity of cells growing within the pores 114, thus preventing formation of a barrier cell layer on the interior surfaces of the pores 114. The porous structure throughout sensing biointerface 90 creates a structure similar to the biointerface depicted in FIG. 3, with the exception that electrodes 100, 102, and 104 are part of the porous structure. It will be appreciated that tissue growth can occur in pores that have an opening 115 on the exterior surface of the biointerface 90. Tissue in-growth may also occur in pores that do not have an opening on the exterior surface of biointerface 90 but that intersect other pores that do have openings on the exterior surface of biointerface 90.

It will be appreciated that the pores 114 within biointerface 90 may make any angle relative to the surfaces of the biointerface 90 and relative to each other and that they may follow a non-straight path within the biointerface 90. It will also be appreciated that the pores 114 may have non-uniform size. In one embodiment, a substantial number of the pores 114 are not less than 20 microns in the shortest dimension and not more than 1000 microns in the longest dimension. In one embodiment, a substantial number of the pores are not less than 25 microns in the shortest dimension and not more than 500 microns in the longest dimension.

As depicted in FIGS. 6B and C, where a pore 114 extends through one of the conductive layers 100, 102, or 104, an interface point 116 is formed between the inside surface of the pore 114 and the electrode 100, 102, or 104. Thus, electrochemical reactions between agents in the pores 114 are possible at interface points 116. Interface points 130 between a pore 114 and working electrode 100 provide a point where analyte sensing can occur. In some embodiments, a plurality of interface points 130 are provided that enable analyte sensing in locations substantially distributed throughout the biointerface. Alternatively, only one or a few interface points could be provided that enable analyte sensing in locations substantially distributed throughout the biointerface. In general, it is advantageous to have a substantial number of pores 114 that extend from one of the surfaces of the biointerface 90 to at least the working electrode 100.

Figure 6C:
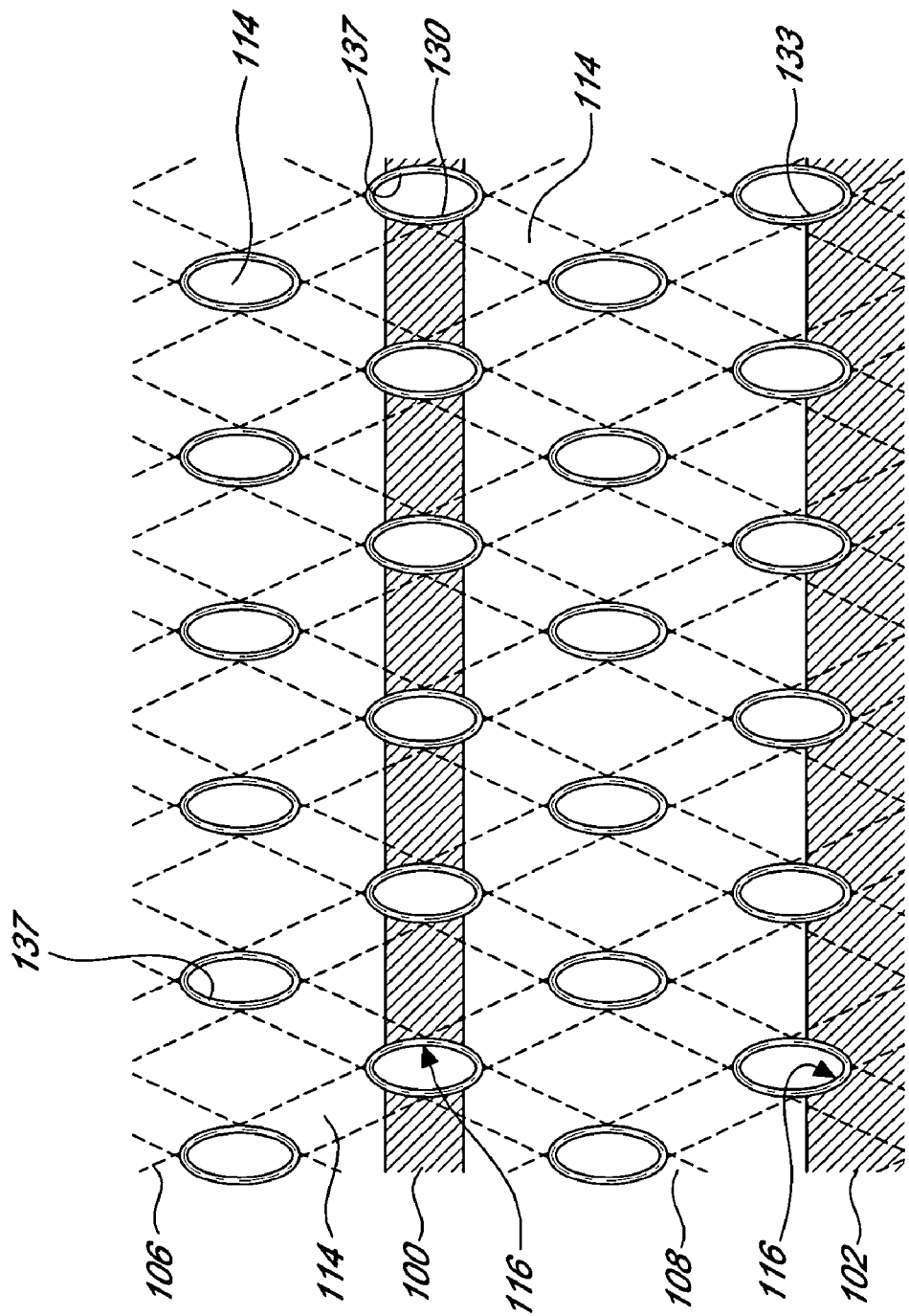
FIG. 6C depicts a cross-sectional expanded view of a portion of the cross-sectional view of FIG. 6B showing the membrane system within the pores of the biointerface.

FIG. 6C depicts a cross-sectional expanded view of a portion of the cross-sectional view of FIG. 6B showing the membrane system within the pores of the biointerface in one embodiment. In some implantable analyte sensors, analyte detection using a structure such as sensing biointerface 90 may be used without a membrane system. In other sensors, such as a glucose sensor, it is advantageous to include a membrane system. Membrane system 137 may be coated on the interior surfaces of pores 114. The coating 137 will then provide an interface between the interior of pores 114 and interface points 130, 133, and 135. Thus, for example, in a glucose sensor, glucose supplied within pores 114 by in-grown vasculature will diffuse through membrane system 137, contact glucose oxidase enzyme situated at the interface between the membrane system 137 and the working electrode, where it will be oxidized producing hydrogen peroxide as a by-product. The hydrogen peroxide can then be electrochemically oxidized, and thus detected, at interface point 130 on working electrode 100.

The membrane systems for use in the sensing biointerfaces described herein may be any single- or multiple-component membrane that enhances detection of the desired analyte. Some embodiments of membranes useful for glucose detection are disclosed in U.S. application Ser. No. 10/153,356, filed on May 22, 2002, which is incorporated herein by reference in its entirety.

In the embodiment of FIGS. 6A to 6C, the working 100, counter 102, and reference electrodes 104 are incorporated within non-conductive layers 106, 108, 110, and 112. Thus, all of the electrodes are internal to the sensing biointerface 90. Alternatively, only the working electrode 100 is internal to the biointerface 150. As in the embodiment of FIGS. 6A to 6C, the optional counter electrode 102 and reference electrode 104 are separated from the working electrode 100 by non-conductive layers 106 and 108. Alternatively, reference and/or counter electrode(s) can be external to the device (e.g., not implanted) and may exist in any known configuration as is appreciate by one skilled in the art. However, additional non-conductive layers are not provided on the tissue sides of the counter 102 and reference 104 electrodes. This configuration is advantageous because the total number of layers are decreased, thus simplifying manufacture. Furthermore, because the counter electrode 102 will have one surface exposed to surrounding tissue without being blocked by one of the non-conductive layers, it will have a much greater surface area exposed to the extracellular electrolyte solution, thus decreasing its impedance and lowering solution resistance. In such an alternative embodiment wherein reference and counter electrodes are on external (tissue-facing) surfaces of the biointerface, the membrane system can be coated onto the exterior surfaces and of the counter electrode 102 and 104 respectively, if desired, in addition to the interior surfaces of pores the 114.

It will be appreciated that the working, reference, and optional counter electrodes may be placed in any location within the sensing biointerfaces described herein. However, it is advantageous to place the working electrode within the interior of the sensing biointerface so that it will be exposed to the optimal cell-disrupted FBR environment. Such a placement inhibits the formation of a barrier cell layer on the working electrode.

Figure 7:
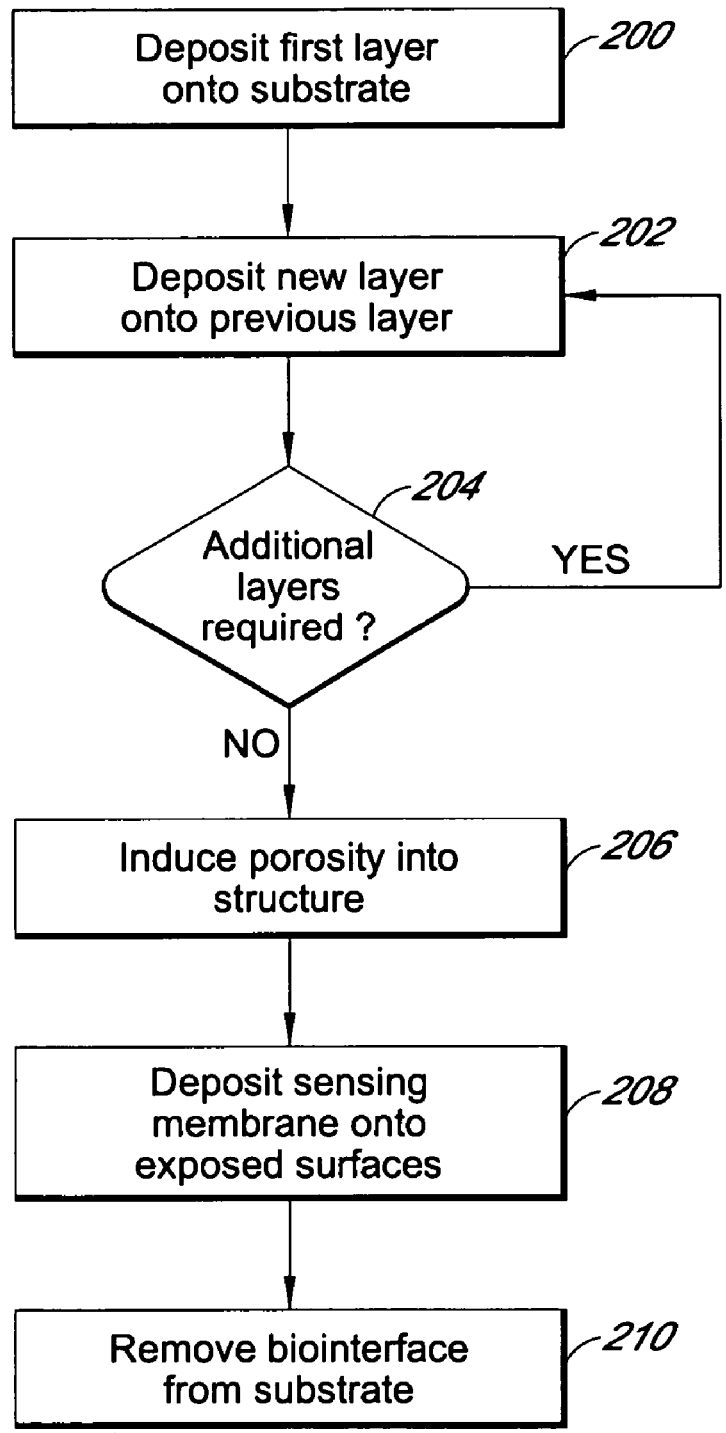
FIG. 7 depicts a flowchart of a process for manufacturing a sensing biointerface.

Some embodiments of the present invention relate to methods for manufacturing a sensing biointerface such as depicted in FIGS. 6A to 6C. Because the general structure of these biointerfaces is a plurality of planar layers deposited on top of each other, manufacturing can be done using any of a number of known techniques for manufacturing multi-layer thin or thick film structures. For example, techniques typically used in semiconductor manufacturing may be applied. FIG. 7 depicts a flowchart of one process sequence that can be used. At block 200, the first layer of the biointerface is deposited onto a substrate. The substrate may be any suitable surface such as glass or plastic. In one advantageous embodiment, the substrate allows for easy removal of the biointerface after manufacturing is complete. In one embodiment, the substrate comprises polytetrafluoroethylene. The first layer deposited onto the substrate may be either a non-conductive layer or a conductive layer, depending on the desired final configuration of layers. For example, in the embodiment of FIGS. 6A to 6C, the first layer may be non-conductive layer 110. Alternatively, the first layer may be counter electrode 102. At block 202, an additional layer is deposited onto the first layer. The composition of the additional layer depends on the final desired configuration. At decision block 204, it is determined whether additional layers are required. If so, the process returns to block 202 for the deposition of a new layer. The process continues until all desired layers have been deposited. Then, at block 206, an interconnected pore structure is induced into the structure. The interconnected pore structure may be induced by any method known in the art for generating pore structures. In one embodiment, the pores are generated by chemical etching of the layered structure. In another embodiment, porosity is generated by plasma etching of the layered structure. At block 208, a membrane system is deposited on all exposed surfaces if desired. Any suitable method for depositing the membrane system may be used, including but not limited to dip coating and vapor deposition. Where the membrane system comprises multiple layers, such as an enzyme layer and a polymeric diffusion layer, the layers can be deposited sequentially. Finally, at block 210, the completed biointerface is removed from the substrate and incorporated with the other components required for the biosensor, such as sensing electronics and a power source.

It will be appreciated that the method illustrated in FIG. 7 may be modified as desired. For example, it may be advantageous to remove the biointerface from the substrate at an earlier step, such as prior to deposition of a membrane system. Furthermore, it may be advantageous to induce porosity in some of the deposited layers prior to deposition of all of the layers.

Deposition of each layer may be by any suitable deposition technique. Non-limiting examples of deposition techniques include dip coating, vapor deposition, sputtering, lamination, brush application, thick film, spin coating, and ink jet application. In some embodiments, different deposition techniques are used for different layers.

In some embodiments, photolithography techniques may be used to define the location and size of pore openings in the surface of the biointerface. For example, masks may be applied on one or more of the surfaces of the biointerface and appropriate pore openings photolithographically defined. Etching may then induce pore formation into the biointerface through the photolithographically defined openings. Finally, the masks can be removed by an appropriate etch process. In one embodiment, pore openings are defined in a regular array on the surfaces of the biointerface. In one embodiment, when the counter electrode and reference electrode comprise the outer surface of the biointerface, such as the embodiment of FIG. 6B, they can be used as masks in the porosity inducing etch step.

Figure 8A:
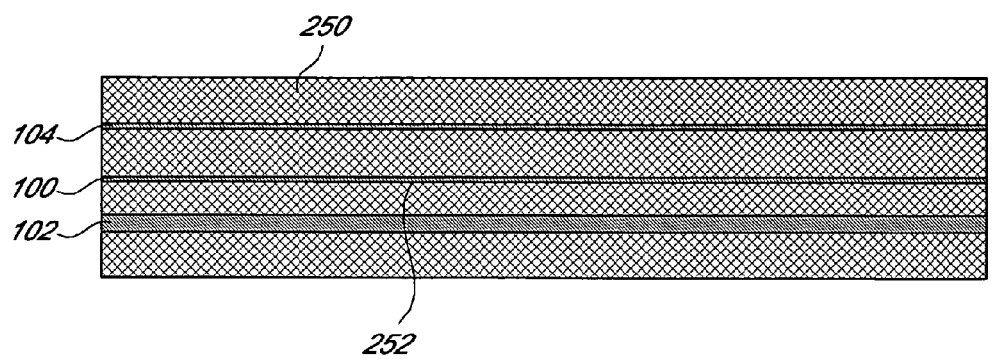
FIGS. 8A and 8B depict cross-sectional views of a sensing cell-disruptive biointerface comprising a mesh structure that incorporates electrodes as part of the biointerface.
Figure 8B:
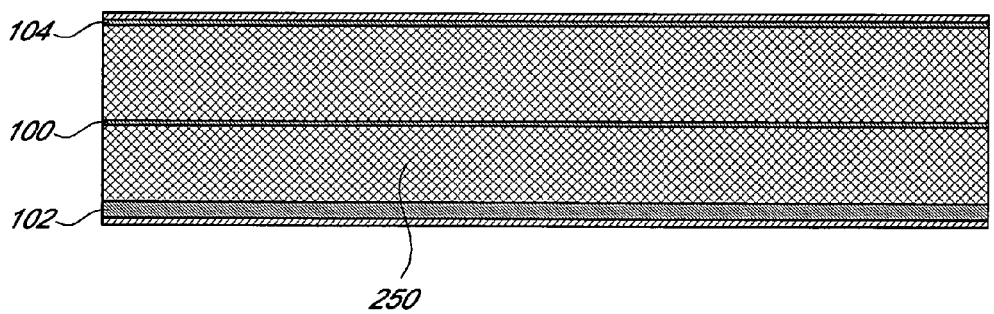

FIGS. 8A and 8B depict cross-sectional views of other embodiments of a sensing biointerface. In FIG. 8A, a mesh structure or scaffolding 250 is provided. Incorporated within the mesh structure 250 are working electrode 100, counter electrode 102, and reference electrode 104. In some embodiments, the mesh structure 250 consists of non-woven fibers. In other embodiments, the mesh structure 250 consists of woven fibers. The fibers of mesh structure 250 may be electrically non-conductive in order to insulate the electrodes 100, 102, and 104 from each other. However, in one embodiment, the mesh structure 250 is constructed of an electrically conductive material, such a metal threading, that is then coated with a non-conductive material. The mesh structure 250 provides spaces in between the fibers for FBR tissue in-growth, however, barrier cell layers are disrupted as is depicted in FIG. 2. Analyte sensing can occur at any location 252 where the surface of working electrode 102 interfaces with an opening between the mesh fibers. If desired the electrodes 100, 102, and 104 may be coated with a membrane system as described herein. In the alternative embodiment of FIG. 8B, working electrode 100 is still embedded within mesh 250; however, counter electrode 102 and reference electrode 104 are deposited onto the surfaces of the mesh structure 250.

Non-limiting examples of fibers that may be used for mesh structure 250 include polypropylene, polytetrafluoroethylene, polyvinylchloride, polyvinylidene fluoride, polybutylene terephthalate, polymethylmethacrylate, polyether ether ketone, polyurethanes, polyolefins, polyesters, polycarbonates, cellosic polymers, polysulfones, and block copolymers thereof including, for example, di-block, triblock, alternating, random, and graft copolymers. In some embodiments, non-woven fibers are greater than about 5 microns in the shortest dimension. In some embodiments, non-woven fibers are greater than about 10 microns in the shortest dimension.

The electrodes 100, 102, and 104 are formed from electrically conductive mesh, wires, or other porous structure such that tissue grows therebetween, which together with the insulating mesh structure 250, forms the sensing biointerface configured for substantial tissue ingrowth including a mature bed of vascularization.

It will be appreciated that other methods besides inducing porosity and using mesh structures can be used to form matrixes that comprise passageways from the exterior of the matrix to a working electrode disposed within the matrix. Thus, many other sensing biointerface structures are within the scope of this disclosure.

For example, in one alternative embodiment, a biointerface matrix, also referred to as a biocompatible matrix, surrounds a sensing mechanism. FIG. 9A depicts a schematic surface view of a porous biointerface 300 that surrounds a sensing mechanism 302. The sensing mechanism may include a working electrode, with or without a membrane system as described herein. In some embodiments, the sensing mechanism may also include a reference and/or counter electrode. Reference and/or Counter electrode(s) may also be incorporated into the biointerface matrix and/or provided external to the biointerface matrix as described elsewhere herein.

In some embodiments, the sensing mechanism does not itself include passageways or pores, but rather is sized small enough (e.g., in at least one dimension) and/or incorporated into the biointerface matrix in such a way so as to manage the foreign body response with the biointerface matrix to resist barrier cell formation and allow the transport of analytes to the sensing mechanism long-term (e.g., 1 day to 1 year or more). For example, in some embodiments, at least one dimension of the sensing mechanism may be sized similarly to the size of passageways or structures within the non-sensing portion of the biointerface matrix (e.g., pore diameter of a porous structure or fiber diameter of a fibrous structure). In one embodiment, the sensing mechanism has a size in at least one dimension of less than about 1000 microns, however other configurations are possible. In some embodiments, both the biointerface matrix and the sensing mechanism are substantially indistinguishable to cells in a host's biological response, such that cells grow in and around the sensing biointerface substantially without barrier cells, thereby enabling sensing of the analyte (e.g., glucose) throughout the sensing biointerface for a long time (e.g., from days to years).

In the embodiment illustrated in FIG. 9A of a porous biointerface matrix, also referred to as a biocompatible matrix, a substantial number of the cavities may be greater than or equal to about 20 microns in one dimension (e.g., a substantial number of the cavities are greater than or equal to about 30, 40, 50, 60, 70, 80, 90, 100, 120, 140, 160, 180, 200, 240, 280, 320, 360, 400, 500, 600, 700 microns in one dimension). In some embodiments, a substantial number of the cavities are less than or equal to about 1000 microns in one dimension (e.g., a substantial number of the cavities are less than or equal to about 900, 800, 700, 600, 500, 400, 360, 320, 280, 240, 200, 180, 160, 140, 120, 100 microns in one dimension.) Although FIG. 9A illustrates a porous biointerface matrix, in some embodiments, the biocompatible matrix includes non-woven materials, woven materials, or other such materials, such that a porous structure is formed from the cavities between the fibers. In these embodiments, for example, the fibers are formed by structural elements that provide the three-dimensional conformation. Therefore in these embodiments, the biocompatible matrix may be defined by a fiber size of between about 1 and 100 microns in all but the longest dimension and a sufficient number of cavities of a size and structure to allow inflammatory cells (for example, macrophages) to completely enter therein through the apertures that define the cavities.

A variety of sensing mechanisms having the characteristics described above can be incorporated into a biointerface matrix. For example, in some embodiments, the sensing mechanism is a wire structure, with or without membrane systems as described herein. FIG. 9B depicts a longitudinal cross-section of one exemplary wire-type sensor. The wire-type sensor in FIG. 9B includes a working electrode wire 306 with exposed electroactive portions 308. The electroactive portions 308 are optionally coated with a membrane system as described herein. Although a wire-type sensor is described herein, the sensing biointerface of the preferred embodiments can utilize other appropriately sized sensors, for example, a planar substrate-based sensor such as described in U.S. Pat. No. 6,565,509, which is incorporated herein by reference in its entirety.

The electrode 306 is formed from a fine wire with a diameter of from about 0.001 inches or less to about 0.010 inches or more. In preferred embodiments, the working electrode 306 comprises a wire formed from a conductive material, such as platinum, platinum-iridium, palladium, graphite, gold, carbon, conductive polymer, alloys, or the like. Although the electrodes can by formed by a variety of manufacturing techniques (bulk metal processing, deposition of metal onto a substrate, or the like), it can be advantageous to form the electrodes from plated wire (e.g., platinum on steel wire) or bulk metal (e.g., platinum wire). It is believed that an electrode formed from bulk metal wire provide superior performance (e.g., in contrast to deposited electrodes), including increased stability of assay, simplified manufacturability, resistance to contamination (e.g., which can be introduced in deposition processes), and improved surface reaction (e.g., due to purity of material) without peeling or delamination.

In some embodiments, the working electrode 306 is covered with an insulating material 312, for example, a non-conductive polymer. Dip-coating, spray-coating, vapor-deposition, or other coating or deposition techniques can be used to deposit the insulating material on the working electrode. In one embodiment, the insulating material comprises parylene, which can be an advantageous polymer coating for its strength, lubricity, and electrical insulation properties. Generally, parylene is produced by vapor deposition and polymerization of para-xylylene (or its substituted derivatives). While not wishing to be bound by theory, it is believed that the lubricious (e.g., smooth) coating (e.g., parylene) on the sensors of the preferred embodiments contributes to minimal trauma and extended sensor life. However, an insulator material is not required.

In embodiments wherein an outer insulator 312 is used, portion(s) of the coated assembly structure can be stripped or otherwise removed, for example, by hand, excimer lasing, chemical etching, laser ablation, grit-blasting (e.g., with sodium bicarbonate or other suitable grit), or the like, to expose the electroactive surfaces 308. Alternatively, a portion of the electrode can be masked prior to depositing the insulator in order to maintain an exposed electroactive surface area 308. In one exemplary embodiment, grit blasting is implemented to expose the electroactive surfaces 308, preferably utilizing a grit material that is sufficiently hard to ablate the polymer material, while being sufficiently soft so as to minimize or avoid damage to the underlying metal electrode (e.g., a platinum electrode). Although a variety of "grit" materials can be used (e.g., sand, talc, walnut shell, ground plastic, sea salt, and the like), in some preferred embodiments, sodium bicarbonate is an advantageous grit-material because it is sufficiently hard to ablate, e.g., a parylene coating without damaging, e.g., an underlying platinum conductor. One additional advantage of sodium bicarbonate blasting includes its polishing action on the metal as it strips the polymer layer, thereby eliminating a cleaning step that might otherwise be necessary.

In some alternative embodiments, multiple electrodes can be included within the sensing biointerface 300. For example, a three-electrode system (working, reference, and counter electrodes) and/or additional working electrode(s) (e.g., an electrode which can be used to generate oxygen, which is configured as a baseline subtracting electrode, or which is configured for measuring additional analytes). U.S. Publication No. US-2005-0161346-A1 and U.S. Publication No. US-2005-0143635-A1 describe some systems and methods for implementing and using additional working, counter, and/or reference electrodes. The resulting electrode system can be configured with an appropriate membrane system, such as the membranes described herein, wherein the first working electrode is configured to measure a first signal comprising glucose and baseline and the additional working electrode is configured to measure a baseline signal consisting of baseline only (e.g., configured to be substantially similar to the first working electrode without an enzyme disposed thereon). In this way, the baseline signal can be subtracted from the first signal to produce a glucose-only signal that is substantially not subject to fluctuations in the baseline and/or interfering species on the signal.

A membrane system can be deposited on the exposed electroactive surfaces (and/or portions or entirety of sensing mechanism) using known thin film techniques (for example, vapor deposition, spraying, electro-depositing, dipping, or the like) as described in more detail elsewhere herein.

In some embodiments, the biointerface matrix 304 may be formed around wire electrode(s) or other electrodes using a pre-formed shape and structure. In some embodiments, the sensing biointerface can be manufactured by forming particles (e.g., sugar, salt, or other natural or synthetic uniform or non-uniform particles) in a mold including the sensing mechanism (e.g., a wire electrode), wherein the particles have shapes and sizes substantially corresponding to the desired cavity dimensions. Most often, the particles are made to coalesce within the mold (e.g. around the sensing mechanism) to provide the desired interconnectivity between the cavities.

The desired material for the solid portion (e.g., silicone, elastomeric conductive carbon, and the like) can be introduced into the mold using methods common in the art of polymer processing, for example injecting, pressing, vacuuming, or pouring, while taking care to work with the sensing mechanism within the mold. After the solid portion material is cured or solidified, the coalesced particles are then dissolved, melted, etched, or otherwise removed leaving interconnecting cavities within the solid portion.

Accordingly, the nominal cavity size of the cavities of the biointerface matrix can be substantially defined by the particle size used in creating the cavities. It is noted that in some embodiments, the particles used to form the cavities can be substantially spherical, thus the dimensions below describe a diameter of the particle and/or a diameter of the cavity. In some alternative embodiments, the particles used to form the cavities can be non-spherical (e.g., rectangular, square, diamond, or other geometric or non-geometric shapes), thus the dimensions below describe one dimension (e.g., shortest, average, or longest, for example) of the particle and/or cavity.

In some embodiments, a variety of different particle sizes can be used in the manufacture of the biointerface matrix. In some embodiments, the dimensions of the particles can be somewhat smaller or larger than the dimensions of the resulting cavities due to dissolution or other precipitation that can occurring during the manufacturing process, for example.

One preferred material that can be used to form the solid portion of the biointerface matrix is a material that allows the passage of the analyte (e.g., glucose) therethrough. For example, the biointerface matrix may be formed from a silicone polymer/hydrophobic-hydrophilic polymer blend. In one embodiment, The hydrophobic-hydrophilic polymer for use in the blend may be any suitable hydrophobic-hydrophilic polymer, including but not limited to components such as polyvinylpyrrolidone (PVP), polyhydroxyethyl methacrylate, polyvinylalcohol, polyacrylic acid, polyethers such as polyethylene glycol or polypropylene oxide, and copolymers thereof, including, for example, di-block, tri-block, alternating, random, comb, star, dendritic, and graft copolymers (block copolymers are discussed in U.S. Pat. Nos. 4,803,243 and 4,686,044, which are incorporated herein by reference). In one embodiment, the hydrophobic-hydrophilic polymer is a copolymer of poly(ethylene oxide) (PEO) and poly(propylene oxide) (PPO). Suitable such polymers include, but are not limited to, PEO-PPO diblock copolymers, PPO-PEO-PPO triblock copolymers, PEO-PPO-PEO triblock copolymers, alternating block copolymers of PEO-PPO, random copolymers of ethylene oxide and propylene oxide, and blends thereof. In some embodiments, the copolymers may be optionally substituted with hydroxy substituents. Commercially available examples of PEO and PPO copolymers include the PLURONIC® brand of polymers available from BASF®. In one embodiment, PLURONIC® F-127 is used. Other PLURONIC® polymers include PPO-PEO-PPO triblock copolymers (e.g., PLURONIC® R products). Other suitable commercial polymers include, but are not limited to, SYNPERONICS® products available from UNIQEMA®.

The silicone polymer for use in the silicone/hydrophobic-hydrophilic polymer blend may be any suitable silicone polymer. In some embodiments, the silicone polymer is a liquid silicone rubber that may be vulcanized using a metal- (e.g., platinum), peroxide-, heat-, ultraviolet-, or other radiation-catalyzed process. In some embodiments, the silicone polymer is a dimethyl- and methylhydrogen-siloxane copolymer. In some embodiments, the copolymer has vinyl substituents. In some embodiments, commercially available silicone polymers may be used. For example, commercially available silicone polymer precursor compositions may be used to prepare the blends, such as described below. In one embodiment, MED-4840 available from NUSIL® Technology LLC is used as a precursor to the silicone polymer used in the blend. MED-4840 consists of a 2-part silicone elastomer precursor including vinyl-functionalized dimethyl- and methylhydrogen-siloxane copolymers, amorphous silica, a platinum catalyst, a crosslinker, and an inhibitor. The two components may be mixed together and heated to initiate vulcanization, thereby forming an elastomeric solid material. Other suitable silicone polymer precursor systems include, but are not limited to, MED-2174 peroxide-cured liquid silicone rubber available from NUSIL® Technology LLC, SILASTIC® MDX4-4210 platinum-cured biomedical grade elastomer available from DOW CORNING®, and Implant Grade Liquid Silicone Polymer (durometers 10-50) available from Applied Silicone Corporation.

Silicone polymer/hydrophobic-hydrophilic polymer blends are described in more detail in U.S. patent application Ser. No. 11/404,417, entitled "SILICONE BASED MEMBRANES FOR USE IN IMPLANTABLE GLUCOSE SENSORS," filed on Apr. 14, 2006, which is incorporated herein by reference in its entirety.

Although one method of manufacturing porous domains is described above, a variety of methods known to one of ordinary skill in the art can be employed to create the structures of preferred embodiments. For example, molds can be used in the place of the particles described above, such as coral, self-assembly beads, etched or broken silicon pieces, glass frit pieces, and the like. The dimensions of the mold can define the cavity sizes, which can be determined by measuring the cavities of a model final product, and/or by other measuring techniques known in the art, for example, by a bubble point test. In U.S. Pat. No. 3,929,971, Roy discloses a method of making a synthetic membrane having a porous microstructure by converting calcium carbonate coral materials to hydroxyapatite while at the same time retaining the unique microstructure of the coral material.

Other methods of forming a three-dimensional biointerface matrix can be used, for example holographic lithography, stereolithography, and the like, wherein cavity sizes are defined and precisely formed by the lithographic or other such process to form a lattice of unit cells, as described in Published U.S. Patent Application 2005-0251083, entitled "Macro-Micro Architecture for Biointerface Membrane," which is incorporated herein by reference in its entirety and as described by Pekkarinen et al. in U.S. Pat. No. 6,520,997, which discloses a photolithographic process for creating a porous membrane. In another embodiment, the biointerface matrix can "written" using computer-aided manufacturing techniques. In one such example, the biointerface matrix is fabricated by dispensing of very small volumes of liquid silicone rubber (LSR), by a robot, onto a heated platform, in an array called out by a CAD-like code programmed into the computer controlling the robot, whereby layers of LSR would be added onto the structure as the layers beneath them are cured by the heat. One such method has been disclosed in U.S. Published Patent Application No. 2004-0253365-A1 entitled "Architecture Tool and Methods of Use," which is incorporated herein by reference in its entirety. Alternatively, the biointerface matrix includes non-woven materials, woven materials, or other such materials, such that a porous structure is formed from the cavities between the fibers. In any of the above methods of forming the biointerface matrix, the matrix can be formed around a sensing mechanism as illustrated with reference to FIG. 9A. FIGS. 10 to 14 are flowcharts illustrating various exemplary processes for obtaining a structure having a biointerface matrix surrounding a sensing mechanism, such as depicted in FIG. 9A.

FIG. 10 is a flow chart that illustrates the process 151 of forming a biointerface-coated small structured sensing mechanism in one embodiment. In this embodiment, the biointerface matrix includes woven or non-woven fibers formed directly onto the sensing mechanism. Generally, fibers can be deposited onto the sensing mechanism using methods suitable for formation of woven- or non-woven fibrous materials. In some embodiments, the biointerface matrix is electrospun directly onto the sensing mechanism; electrospinning advantageously allows the biointerface matrix to be made with small consistent fiber diameters that are fused at the nodes and are without aggregation. In some embodiments, the biointerface matrix is directly written onto the sensing mechanism; direct-writing can advantageously allow uniform deposition of stored patterns for providing consistent and reproducible architectures.

At block 153, one or more dispensers dispense a polymeric material used to form the fibers, such as any of the polymeric materials described herein. The coating process can be performed in a vacuum or in a gaseous medium, which environment may affect the architecture of the biointerface matrix as is appreciated by one skilled in the art.

In embodiments wherein the biointerface is electrospun onto the sensing mechanism, the dispenser dispenses a charged liquefied polymer within an electric field, to thereby form a jet of polymer fibers, for example, such as described in International Published Patent Application No. WO 2005/032400, which is incorporated herein by reference in its entirety. In embodiments wherein the biointerface is directly-written onto the sensing mechanism, the dispenser dispenses a polymer solution using a nozzle with a valve, or the like, for example as described in U.S. Published Patent Application No. 2004/0253365, which is incorporated herein by reference in its entirety. In general, a variety of nozzles and/or dispensers can be used to dispense a polymeric material to form the woven or non-woven fibers of the biointerface matrix.

Figure 9C:
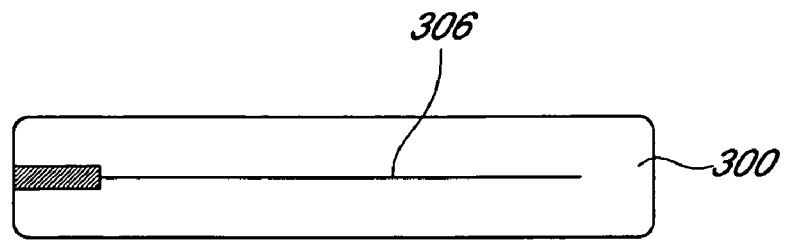
FIG. 9C depicts a schematic cross-sectional view of a sensing biointerface in one embodiment, including a single wire sensor incorporated into a cylindrical shaped biointerface matrix.

At block 154, the dispenser(s) is moved relative to the sensing mechanism and/or the sensing mechanism is moved relative to the dispenser(s) so as to coat the sensing mechanism with the fibers. In embodiments wherein the biointerface matrix is electrospun onto the sensing mechanism, the dispenser(s) can change the direction and/or magnitude of the electric field during motion in order to effect the orientation of the polymer fibers on the sensing mechanism. Additionally, the path of the dispenser is preferably selected so as to coat the portions of or the entire object. In one exemplary embodiment, wherein it is desirable for the biointerface matrix to substantially circumscribe the sensing mechanism (e.g., a substantially cylindrical shape), such as illustrated in FIG. 9C described below, the dispenser can be moved along a helix path, a circular path, a zigzag path, or the like. Additionally, the dispenser can move rotationally and/or translationally relative to the sensing mechanism. The number of sweeps is preferably selected according to the desired architecture of the biointerface matrix. Additionally, the density of the fibers and/or the type of liquefied polymer can be changed from one sweep to the other to thereby control the architecture of the membrane.

In embodiments where the biointerface matrix is directly written onto the sensing mechanism, the dispenser may be programmed to write a pattern that creates the desired membrane architecture, including the interconnected cavities and solid portion(s). Namely, the dispenser is programmed to move in the x, y, and optionally z direction in order to create the desired membrane architecture. See, for example, U.S. Published Patent Application No. 2004/0253365 cited above.

Although the preferred embodiments described moving the dispenser(s) relative to the sensing mechanism, alternatively, the dispenser can remain stationary and the sensing mechanism moved, as is appreciated by one skilled in the art.

In some embodiments, the sensing mechanism is moved in a rotational or translational motion, which can be performed in combination with, or instead of, movement of the dispenser. In this step, the sensing mechanism is moved so as to ensure coating throughout the entirety of the biointerface region (or a portion thereof). In one exemplary embodiment, wherein a substantially circumscribing biointerface matrix is desired (e.g., for a substantially cylindrically shaped sensing mechanism) such as illustrated in FIG. 9C, the sensing mechanism can be rotated so to aid in coating the entire circumference of the sensing mechanism. In another exemplary embodiment, wherein a substantially planar biointerface matrix is desired (e.g., for a substantially planar sensing mechanism), the sensing mechanism can be translated so as to aid in coating the desired planar surface area.

Figure 11:
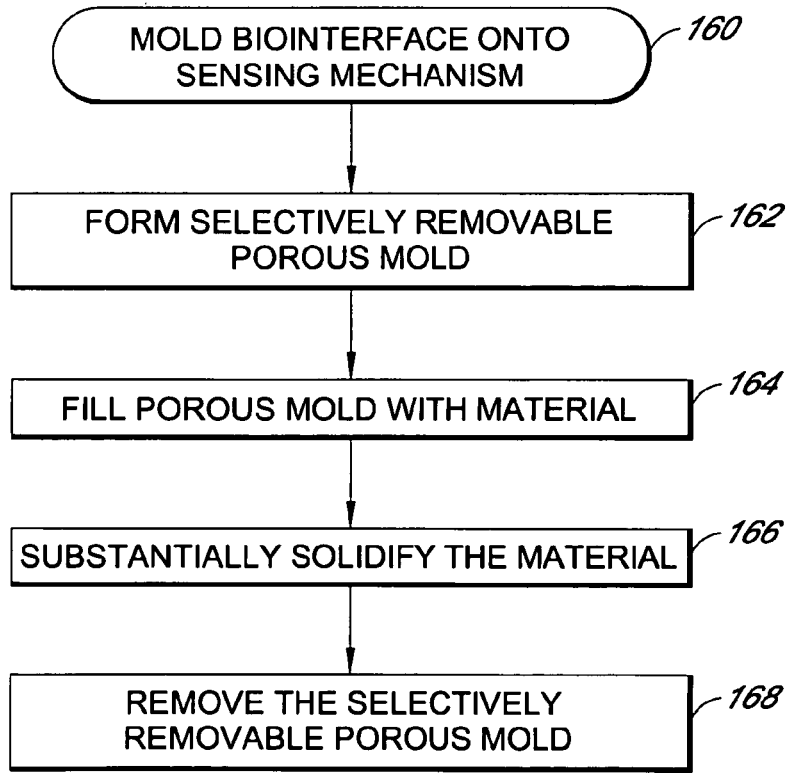
FIG. 11 is a flow chart that illustrates a process of molding a biointerface matrix onto a sensing mechanism.

FIG. 11 is a flow chart that illustrates the process 160 of forming a biointerface-coated sensing mechanism in an alternative embodiment. In this embodiment, the biointerface matrix is porous in configuration, such as illustrated in FIG. 3, for example.

At block 162, a selectively removable porous mold is formed by spraying, coating, rolling, or otherwise forming selectively removable particles, for example, sugar crystals, onto the surface of the sensing mechanism. Additional examples of materials suitable as selectively removable mold material include thermoplastic polymers such as waxes, paraffin, polyethylene, nylon, polycarbonate, or polystyrene in naturally available particles or processed into specific sizes, shapes, molded forms, spheres or fibers, salt or other particles which cannot be made to inherently stick together coated with sugar, and certain drug crystals such as gentamycin, tetracycline, or cephalosporins. In general, any dissolvable, burnable, meltable, or otherwise removable particle which can be made to stick together could be used. Preferably, the particles have shapes and sizes substantially corresponding to the desired cavity dimensions, such as described in more detail above. In some embodiments, the particles are made to adhere to the sensing mechanism by environmental conditions, for example, humidity can be used to cause sugar to adhere to the sensing mechanism.

In some embodiments, the particles are made to coalesce to provide the desired interconnectivity between the cavities. In an exemplary porous silicone embodiment, sugar crystals are exposed to a humid environment sufficient to cause coalescence of the sugar crystals. In some alternative embodiments, other molds may be used in the place of the particles described above, for example, coral, self-assembly beads, etched and broken silicon pieces, glass frit pieces, and the like.

At block 164, a material (e.g., a moldable or conformable material) is filled or coated into the interconnected cavities of the mold using methods common in the art of polymer processing, for example, injecting, pressing, vacuuming, vapor depositing, pouring, and the like. Examples of materials suitable for the resulting porous device include polymers, metals, metal alloys, ceramics, biological derivatives, and combinations thereof, in solid or fiber form. In an exemplary porous silicone embodiment, silicone is pressed into the interconnected cavities of the mold.

At block 166, the material is substantially cured or solidified to form the solid portion(s) of the biointerface matrix. Solidification of the material can be accelerated by supplying dry air (which may be heated) to the material, for example. Additionally, freezing, freeze drying or vacuum desiccation, with or without added heat, may also be utilized to cause the material to solidify. In some circumstances, a skin or any excess material can be removed (e.g., shaved, etched, or the like) after curing. In the exemplary porous silicone embodiment, an outer skin of silicone is removed to expose the interconnected cavities at an outer surface.

At block 168, the selectively removable porous mold is dissolved, melted, etched, or otherwise removed, leaving interconnecting cavities within the solid portion. Preferably, the selectively removable porous mold is readily removable without significantly altering the final product (or product material). This removal may be by dissolution by some solvent that does not significantly dissolve the final product material. Alternatively, the mold material may be melted (or burned) out of the final product material if the melting point (or burning point) of the mold material is below that of the final product material. In the exemplary porous silicone embodiment, water is used to dissolve the sugar crystals.

Figure 12:
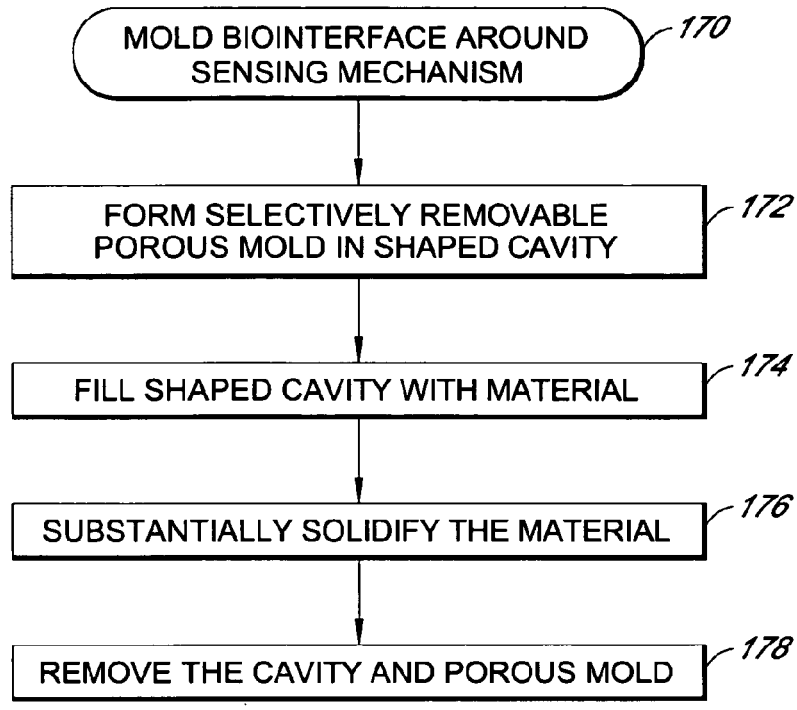
FIG. 12 is a flow chart that illustrates an alternative process of molding a biointerface matrix onto a sensing mechanism.

FIG. 12 is a flow chart that illustrates the process 170 of forming a biointerface-coated small structured sensing mechanism in another alternative embodiment. In this embodiment, the biointerface matrix is porous in configuration, such as illustrated in FIG. 3, for example.

At block 172, a selectively removable porous mold is formed by filling a shaped cavity with selectively removable particles, for example, sugar crystals, wherein the sensing mechanism is located within the shaped cavity, and wherein the selectively removable particles substantially surround the sensing mechanism. Additional examples of materials suitable as selectively removable mold material are described with reference to block 162, above. In some embodiments, the shaped cavity mold is formed from a selectively removable material (e.g., sacrificial cavity mold) similar the selectively removable particles described above. One such example includes a tube formed from a dissolvable polymer. Alternatively, the shaped cavity can be a non-selectively removable material, and instead, a sacrificial layer of selectively removable material is formed directly onto the cavity walls, enabling the removal of the biointerface matrix after dissolution of the sacrificial layer.

Preferably the shape of the cavity mold substantially corresponds to the desired final shape of the biointerface matrix. In one exemplary embodiment, the cavity mold is substantially cylindrical, for example using a syringe or cannula as the cavity mold.

In some embodiments, the particles are made to coalesce to provide the desired interconnectivity between the cavities. In an exemplary porous silicone embodiment, sugar crystals are exposed to humidity or spray of water sufficient to cause coalescence of the sugar crystals. In some alternative embodiments, other molds may be used in the place of the particles described above, for example, coral, self-assembly beads, etched and broken silicon pieces, glass frit pieces, and the like.

At block 174, a material (e.g., a moldable or conformable material) is filled into the interconnected cavities of the mold using methods common in the art of polymer processing, for example, injecting, pressing, vacuuming, vapor depositing, pouring, and the like. Examples of materials suitable for the resulting porous device are described in more detail with reference to block 164, above. In an exemplary porous silicone embodiment, silicone is pressed into the interconnected cavities of the mold.

At block 176, the material is substantially cured or solidified to form the solid portion(s) of the biointerface matrix. Solidification of the material can be accelerated as described in more detail with reference to block 166, above.

At block 178, the selectively removable porous mold is dissolved, melted, etched, or otherwise removed, leaving interconnecting cavities within the solid portion surrounding the sensing mechanism. In some embodiments, wherein a sacrificial layer is formed as described above, the sacrificial layer can be remove before, during, or after the removal of the selectively removable porous mold. In some embodiments, the final product is removed from the cavity mold before, during, or after the removal of the selectively removable porous mold.

Preferably, the selectively removable porous mold is readily removable without significantly altering the final product (or product material). This removal may be by dissolution by some solvent that does not significantly dissolve the final product material. Alternatively, the mold material may be melted (or burned) out of the final product material if the melting point (or burning point) of the mold material is below that of the final product material. In one exemplary embodiment, a sacrificial tube forms the mold cavity; wherein the sacrificial tube is removed prior to, during, or after dissolution of the selectively removable porous mold. One skilled in the art can appreciate a variety of modifications or combinations of the above described removal step without departing from the spirit of the invention.

Figure 13:
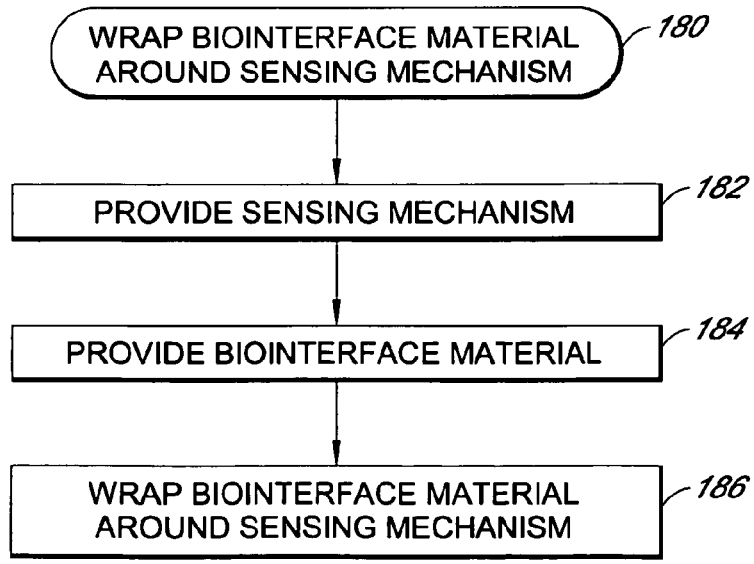
FIG. 13 is a flow chart that illustrates a process of wrapping a sensing mechanism with a biointerface membrane.

FIG. 13 is a flow chart that illustrates the process 180 of forming a biointerface-wrapped sensing mechanism in one embodiment. In this embodiment, the interconnected cavities and solid portion(s) of the biointerface matrix can be fibrous or porous in configuration. In fact, substantially any biointerface matrix with an architecture as described in more detail above, which is formed in substantially any manner, can be used with this embodiment.

At block 182, a sensing mechanism is manufactured and provided, wherein the sensing mechanism is formed with a small structure as discussed above.

At block 184, a biointerface membrane with an architecture as described herein is manufactured in substantially any desired manner, wherein the biointerface membrane is formed substantially as a sheet or tube of membrane.

At block 186, the biointerface membrane is wrapped around the sensing mechanism manually, or using an automated device, as can be appreciated by one skilled in the art. Namely, the biointerface membrane is wrapped such that it substantially surrounds the sensing mechanism. The number of wraps can be from less than 1 to about 100, preferably 1, PA, 2, 2½, 3, 3½, 4, 5, 6, 7, 8, 9, 10, or more. The number of wraps depends on the architecture of the sheet of biointerface membrane, and the desired architecture of the biointerface surrounding the sensing mechanism.

In some embodiments, the circumference (or a portion thereof (e.g., an edge)) of the biointerface membrane with an architecture as described herein can be adhered or otherwise attached or sealed to form a substantially consistent outer surface (of the biointerface membrane). In an aspect of this embodiment, the biointerface membrane is wrapped around the sensing mechanism one time, wherein the "wrap" includes a tubular biointerface membrane configured to slide over the sensing mechanism, for example, be stretching the tubular biointerface membrane and inserting the sensing mechanism therein.

Figure 14:
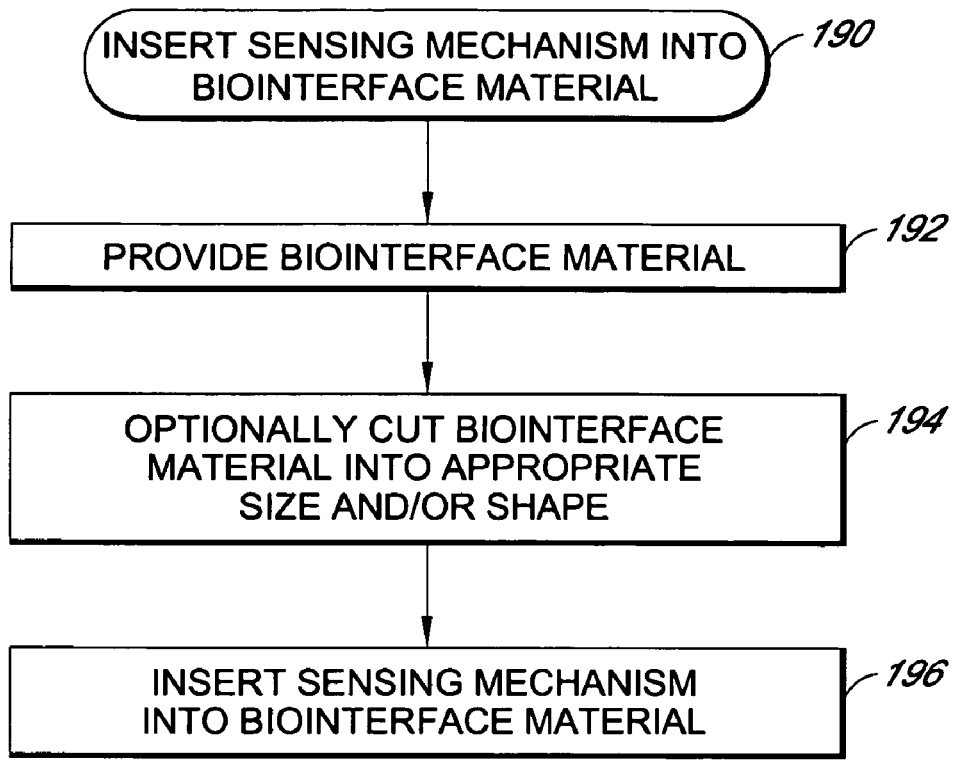
FIG. 14 is a flow chart that illustrates a process of inserting a sensing mechanism into a biointerface matrix.

FIG. 14 is a flow chart that illustrates the process 190 of forming a sensing biointerface in one embodiment. In this embodiment, the sensing mechanism is inserted into the biointerface matrix so that it is encompassed therein.

At block 192, a biointerface matrix is manufactured in substantially any desired manner, such as the methods described above. In some embodiments, the biointerface matrix is molded into the desired final shape to surround the sensing mechanism and implant into a host. Alternatively, the biointerface matrix can be provided as a sheet of bulk material.

At block 194, a particularly shaped or sized biointerface matrix can be optionally cut. Namely, in embodiments wherein the biointerface matrix is provided in bulk, e.g., as a sheet of material, the desire shape or size can be cut therefrom. In these embodiments, bulk biointerface matrix sheet is preferably of the appropriate thickness for the desired final product. In one exemplary embodiment, the biointerface matrix (bulk sheet) is compressed, for example between two substantially rigid structures, and the final size/shape biointerface matrix cut there from, after which the biointerface matrix is released. While not wishing to be bound by theory, it is believed that by compressing the biointerface matrix during cutting, a more precise shape can be achieved. It is noted that biointerface matrix can have sufficient elasticity, such that the thickness is returned after release from compression, as is appreciated by one skilled in the art.

At block 196, a sensing mechanism is inserted into the biointerface matrix. Preferably, the sensing mechanism is inserted into the membrane such that the sensing mechanism contacts at least one or more of the interconnected cavities so that the host analyte can be measured. Alternatively, the biointerface can be formed from a material that allows the flux of the analyte there through. In some embodiments, the sensing mechanism is inserted with the aid of a needle. Alternatively, the sensing mechanism is formed with appropriate sharpness and rigidity to enable insertion through the biointerface matrix.

In some embodiments, an anchoring mechanism, such as a barb, is provided on the sensing mechanism, in order to anchor the sensing mechanism within the biointerface matrix (and/or host tissue). A variety of additional or alternative aspects can be provided to implement the biointerface matrix surrounded sensing mechanisms of the preferred embodiments.

All of the above manufacturing techniques can be used to form the sensing biointerface around a sensing mechanism, as is appreciated by one skilled in the art. Additionally, the sensing biointerface of the preferred embodiments can be implemented in a variety of shapes, sizes, and configurations and with any number of electrodes and electrode configurations. The figures below (FIGS. 9C to 9G) describe a few exemplary embodiments.

FIG. 9C is a schematic cross-sectional view of a sensing biointerface in one embodiment, including a single wire sensor 306 incorporated into a cylindrical shaped biointerface matrix 300 (shown in a side-view cross-section). In one exemplary embodiment, the biointerface is formed as described above, within a cylindrical mold. Although a method of molding the sensing mechanism into the biointerface matrix is described above, other methods may include manufacturing the sensing mechanism and biointerface separately and then assembling them in a final step (e.g., pushing the wire through the biointerface matrix (e.g., with a protective introducer in some embodiments)). The use of a wire electrode provides multiple sensing points along the length of the wire (either a continuous series of sensing points due to an uninsulated length of wire or discrete sensing points due to periodic removal of an insulative coating as described above with reference to FIG. 9B). Accordingly, blockage or dysfunction of certain sensing points along the wire (e.g., due to cellular attack or other malfunction) but not others will not affect the function of the overall sensor.

Figure 9D:
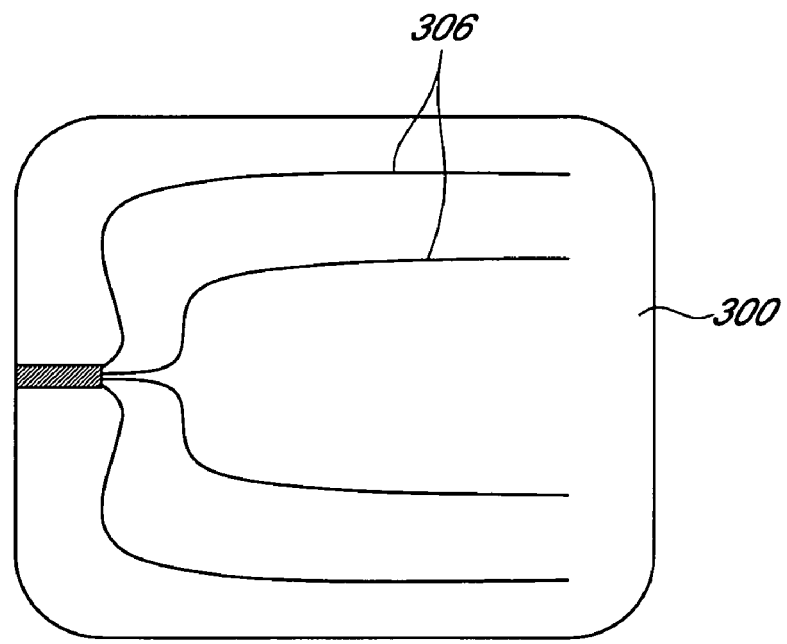
FIG. 9D is a schematic cross-sectional view of a sensing biointerface in another embodiment wherein the sensing biointerface includes a plurality of wire electrodes.

FIG. 9D is a schematic cross-sectional view of a sensing biointerface in another embodiment wherein the sensing biointerface includes a plurality of electrodes 306 (e.g., in fork configuration). For example, working, reference, and/or counter wire electrodes may be separately disposed in the biointerface matrix 300. In addition, multiple working electrodes may be used. A variety of configurations are possible for implementing the plurality of electrodes within the biointerface matrix. One advantage of deploying multiple working electrodes within the porous sensing biointerface is that some blockage or dysfunction on one working electrode (e.g., due to cellular attack or other malfunction) but not others will not affect the function of the overall sensor. In addition, using multiple working wire electrodes increases the overall number of sensing points along the combined lengths of the wires. By using a fork configuration, the sensing points are more widely distributed throughout the biointerface matrix.

Figure 9E:
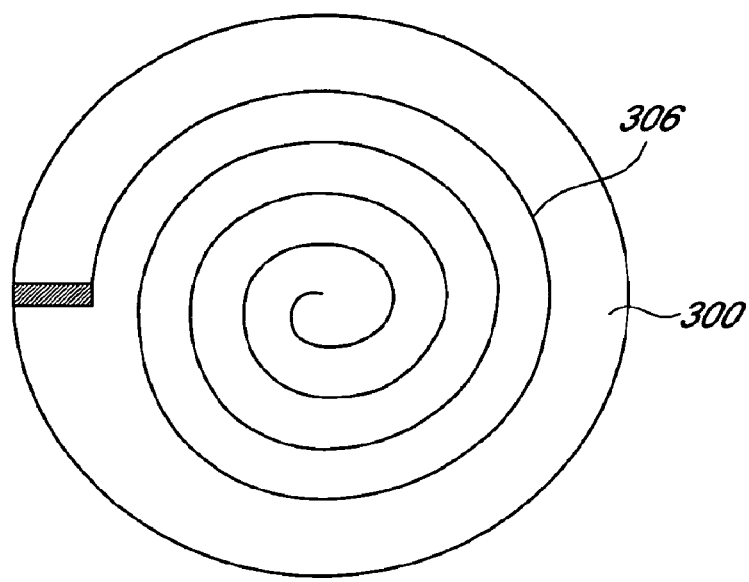
FIG. 9E is a schematic cross-sectional view of a sensing biointerface in yet another embodiment wherein the sensing biointerface comprises a spiral wire electrode.

FIG. 9E is a schematic cross-sectional view of a sensing biointerface in yet another embodiment wherein the sensing biointerface comprises a spiral wire sensor 306. Similar to the above-described plurality of electrodes, the spiral electrode provides an increase distribution of sensing points throughout the sensing biointerface, increasing the probability of good sensor performance.

Figure 9F:
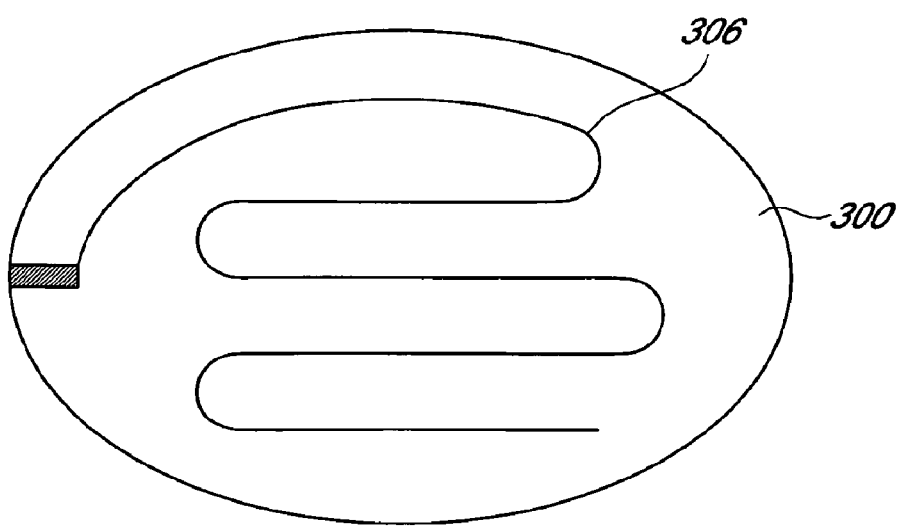
FIG. 9F is a schematic cross-sectional view of a sensing biointerface in yet another embodiment wherein the sensing biointerface comprises a wire electrode in a tortuous path within the biointerface matrix.

FIG. 9F is a schematic cross-sectional view of a sensing biointerface in yet another embodiment wherein the electrode 306 forms a tortuous path within the biointerface matrix 300, again increasing the distribution of sensing points.

Figure 9G:
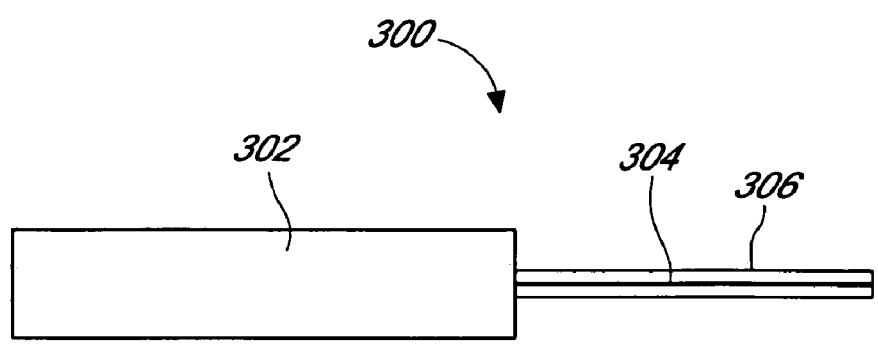
FIG. 9G is a schematic cross-sectional view of a sensing biointerface in yet another embodiment, wherein the sensing biointerface comprises a wire electrode, a biointerface matrix, and a sensor body.

FIG. 9G is a schematic cross-sectional view of a wholly implantable analyte sensor 300 in one embodiment. The sensor 300 includes a sensor body 302 (e.g., for containing the electronics described below) suitable for subcutaneous implantation. Published U.S. Patent Application No. 2004/0199059 to Brauker et al. describes systems and methods suitable for the sensor body 302, and is incorporated herein by reference in its entirety. The sensor 300 also includes a small-structured sensing mechanism consisting of a wire electrode 304 with a biointerface matrix coating 306. The biointerface matrix 306 depicted in FIG. 9G is not necessarily drawn to scale and may be any suitable size and shape when surrounding wire electrode 304. In some embodiments, the wire electrode 304 is coated with a membrane system such as described herein.

One material that may be particularly suitable for either the biointerface matrix and/or the electrode(s) of the sensing mechanism of the preferred embodiments is elastomeric carbon. Elastomeric carbon is a material that is both elastic, which is a preferable property for the biointerface matrix, and is conductive, which is a preferable property for the working electrode(s). Some embodiments contemplate only a portion of the biointerface formed from elastomeric carbon. Because the elastomeric carbon can be used for the sensing mechanism and the biointerface matrix portions of the sensing biointerface, manufacture of the sensing biointerface is made simple. Namely, the biointerface matrix can be formed at least in part from elastomeric carbon using any of the methods described above, after which a membrane system can be directly applied to at least portions thereof, enabling sensing of the analyte. As one example of the elastomeric carbon embodiments described above, the biointerface matrix is formed from woven or non-woven material (e.g., ePTFE) over which elastomeric carbon or other electrode material is deposited (e.g., sprayed), and over which the membrane is deposited (e.g., vapor deposited). Although one example has been suggested, a variety of implementations of the sensing biointerface comprising elastomeric carbon (e.g., as a part of the biointerface matrix and sensing mechanism) are contemplated and included in the preferred embodiments.

In general, sterilization of the transcutaneous sensor can be completed after final assembly, utilizing methods such as electron beam radiation, gamma radiation, glutaraldehyde treatment, or the like. The sensor can be sterilized prior to or after packaging. In an alternative embodiment, one or more sensors can be sterilized using variable frequency microwave chamber(s), which can increase the speed and reduce the cost of the sterilization process. In another alternative embodiment, one or more sensors can be sterilized using ethylene oxide (EtO) gas sterilization, for example, by treating with 100% ethylene oxide, which can be used when the sensor electronics are not detachably connected to the sensor and/or when the sensor electronics must undergo a sterilization process.

Membrane Systems

As discussed above, in some embodiments, the sensing biointerfaces described herein include membranes systems deposited on one or more electroactive surfaces within the biointerface. In some embodiments, one or more domains of the membrane systems are formed from materials such as silicone, polytetrafluoroethylene, polyethylene-co-tetrafluoroethylene, polyolefin, polyester, polycarbonate, biostable polytetrafluoroethylene, homopolymers, copolymers, terpolymers of polyurethanes, polypropylene (PP), polyvinylchloride (PVC), polyvinylidene fluoride (PVDF), polybutylene terephthalate (PBT), polymethylmethacrylate (PMMA), polyether ether ketone (PEEK), polyurethanes, cellulosic polymers, polysulfones and block copolymers thereof including, for example, di-block, tri-block, alternating, random and graft copolymers. Co-pending U.S. patent application Ser. No. 10/838,912, which is incorporated herein by reference in its entirety, describes some biointerface and membrane system configurations and materials that may be applied to the preferred embodiments. Additional examples are described below.

The membrane system can be deposited on the exposed electroactive surfaces using known thin film techniques (for example, vapor deposition, spraying, electro-depositing, dipping, or the like). In alternative embodiments, however, other vapor deposition processes (e.g., physical and/or chemical vapor deposition processes) can be useful for providing one or more of the insulating and/or membrane layers, including ultrasonic vapor deposition, electrostatic deposition, evaporative deposition, deposition by sputtering, pulsed laser deposition, high velocity oxygen fuel deposition, thermal evaporator deposition, electron beam evaporator deposition, deposition by reactive sputtering molecular beam epitaxy, atmospheric pressure chemical vapor deposition (CVD), atomic layer CVD, hot wire CVD, low-pressure CVD, microwave plasma-assisted CVD, plasma-enhanced CVD, rapid thermal CVD, remote plasma-enhanced CVD, and ultra-high vacuum CVD, for example. However, the membrane system can be disposed over (or deposited on) the electroactive surfaces using any known method, as will be appreciated by one skilled in the art. It is noted that the membrane system that surrounds the working electrode does not have to be the same structure as the membrane system that surrounds a reference electrode, etc. For example, the enzyme domain deposited over the working electrode does not necessarily need to be deposited over the reference and/or counter electrodes.

Electrode/Electrolyte Domain

In selected embodiments, the membrane system comprises an electrode domain 56. The electrode domain 56 is preferably situated more proximal to the electroactive surfaces than the interference and/or enzyme domain. Preferably, the electrode domain includes a coating that maintains a layer of water at the electrochemically reactive surfaces of the sensor. For example, a humectant in a binder material can be employed as an electrode domain; this allows for the full transport of ions in the aqueous environment. The electrode domain can also assist in stabilizing the operation of the sensor by accelerating electrode start-up and drifting problems caused by inadequate electrolyte. The material that forms the electrode domain can also provide an environment that protects against pH-mediated damage that can result from the formation of a large pH gradient due to the electrochemical activity of the electrodes.

In one embodiment, the electrode domain 56 includes a flexible, water-swellable, hydrogel film having a "dry film" thickness of from about 0.05 micron or less to about 20 microns or more, more preferably from about 0.05, 0.1, 0.15, 0.2, 0.25, 0.3, 0.35, 0.4, 0.45, 0.5, 1, 1.5, 2, 2.5, 3, or 3.5 microns to about 4, 5, 6, 7, 8, 9, 10, 11, 12, 13, 14, 15, 16, 17, 18, 19, or 19.5 microns, and more preferably still from about 2, 2.5 or 3 microns to about 3.5, 4, 4.5, or 5 microns. "Dry film" thickness refers to the thickness of a cured film cast from a coating formulation by standard coating techniques.

In certain embodiments, the electrode domain 56 is formed of a curable mixture of a urethane polymer and a hydrophilic polymer. Particularly preferred coatings are formed of a polyurethane polymer having carboxylate or hydroxyl functional groups and nonionic hydrophilic polyether segments, wherein the polyurethane polymer is crosslinked with a water soluble carbodiimide (e.g., 1-ethyl-3-(3-dimethylaminopropyl)carbodiimide (EDC)) in the presence of polyvinylpyrrolidone and cured at a moderate temperature of about 50° C.

In some preferred embodiments, the electrode domain 56 is formed from a hydrophilic polymer such as polyvinylpyrrolidone (PVP). An electrode domain formed from PVP has been shown to reduce break-in time of analyte sensors; for example, a glucose sensor utilizing a cellulosic-based interference domain such as described in more detail below.

In one embodiment, the electrode domain 56 is formed from a silicone polymer/hydrophobic-hydrophilic polymer blend. In one embodiment, The hydrophobic-hydrophilic polymer for use in the blend may be any suitable hydrophobic-hydrophilic polymer, including but not limited to components such as polyvinylpyrrolidone (PVP), polyhydroxyethyl methacrylate, polyvinylalcohol, polyacrylic acid, polyethers such as polyethylene glycol or polypropylene oxide, and copolymers thereof, including, for example, di-block, tri-block, alternating, random, comb, star, dendritic, and graft copolymers (block copolymers are discussed in U.S. Pat. Nos. 4,803,243 and 4,686,044, which are incorporated herein by reference). In one embodiment, the hydrophobic-hydrophilic polymer is a copolymer of poly (ethylene oxide) (PEO) and poly(propylene oxide) (PPO). Suitable such polymers include, but are not limited to, PEO-PPO diblock copolymers, PPO-PEO-PPO triblock copolymers, PEO-PPO-PEO triblock copolymers, alternating block copolymers of PEO-PPO, random copolymers of ethylene oxide and propylene oxide, and blends thereof. In some embodiments, the copolymers may be optionally substituted with hydroxy substituents. Commercially available examples of PEO and PPO copolymers include the PLURONIC® brand of polymers available from BASF®. In one embodiment, PLURONIC® F-127 is used. Other PLURONIC® polymers include PPO-PEO-PPO triblock copolymers (e.g., PLURONIC® R products). Other suitable commercial polymers include, but are not limited to, SYNPERONICS® products available from UNIQEMA®.

The silicone polymer for use in the silicone/hydrophobic-hydrophilic polymer blend may be any suitable silicone polymer. In some embodiments, the silicone polymer is a liquid silicone rubber that may be vulcanized using a metal- (e.g., platinum), peroxide-, heat-, ultraviolet-, or other radiation-catalyzed process. In some embodiments, the silicone polymer is a dimethyl- and methylhydrogen-siloxane copolymer. In some embodiments, the copolymer has vinyl substituents. In some embodiments, commercially available silicone polymers may be used. For example, commercially available silicone polymer precursor compositions may be used to prepare the blends, such as described below. In one embodiment, MED-4840 available from NUSIL® Technology LLC is used as a precursor to the silicone polymer used in the blend. MED-4840 consists of a 2-part silicone elastomer precursor including vinyl-functionalized dimethyl- and methylhydrogen-siloxane copolymers, amorphous silica, a platinum catalyst, a crosslinker, and an inhibitor. The two components may be mixed together and heated to initiate vulcanization, thereby forming an elastomeric solid material. Other suitable silicone polymer precursor systems include, but are not limited to, MED-2174 peroxide-cured liquid silicone rubber available from NUSIL® Technology LLC, SILASTIC® MDX4-4210 platinum-cured biomedical grade elastomer available from DOW CORNING®, and Implant Grade Liquid Silicone Polymer (durometers 10-50) available from Applied Silicone Corporation.

Silicone polymer/hydrophobic-hydrophilic polymer blends are described in more detail in U.S. patent application Ser. No. 11/404,417, entitled "SILICONE BASED MEMBRANES FOR USE IN IMPLANTABLE GLUCOSE SENSORS," filed on Apr. 14, 2006, which is incorporated herein by reference in its entirety.

Preferably, the electrode domain is deposited by vapor deposition, spray coating, dip coating, casting, or other thin film techniques on the electroactive surfaces of the sensor. In one preferred embodiment, the electrode domain is formed by dip-coating the electroactive surfaces in an electrode domain solution and curing the domain for a time of from about 15 minutes to about 30 minutes at a temperature of from about 40° C. to about 55° C. (and can be accomplished under vacuum (e.g., 20 to 30 mmHg)). In embodiments wherein dip-coating is used to deposit the electrode domain, a preferred insertion rate of from about 1 to about 3 inches per minute into the electrolyte layer solution, with a preferred dwell time of from about 0.5 to about 2 minutes in the electrolyte layer solution, and a preferred withdrawal rate of from about 0.25 to about 2 inches per minute from the electrolyte layer solution provide a functional coating. However, values outside of those set forth above can be acceptable or even desirable in certain embodiments, for example, depending upon solution viscosity and solution surface tension, as is appreciated by one skilled in the art. In one embodiment, the electroactive surfaces of the electrode system are dip-coated one time (one layer) and cured at 50° C. under vacuum for 20 minutes.

Although an independent electrode domain 56 is described herein, in some embodiments sufficient hydrophilicity can be provided in the interference domain and/or enzyme domain (the domain adjacent to the electroactive surfaces) so as to provide for the full transport of ions in the aqueous environment (e.g. without a distinct electrode domain). In these embodiments, an electrode domain is not necessary.

Interference Domain

Interferents are molecules or other species that are reduced or oxidized at the electrochemically reactive surfaces of the sensor, either directly or via an electron transfer agent, to produce a false positive analyte signal. In preferred embodiments, an interference domain 57 is provided that substantially restricts, resists, or blocks the flow of one or more interfering species. Some known interfering species for a glucose sensor, as described in more detail above, include acetaminophen, ascorbic acid, bilirubin, cholesterol, creatinine, dopamine, ephedrine, ibuprofen, L-dopa, methyl dopa, salicylate, tetracycline, tolazamide, tolbutamide, triglycerides, and uric acid. In general, the interference domain of the preferred embodiments is less permeable to one or more of the interfering species than to the analyte, e.g., glucose.

In some embodiments, the interference domain 57 is formed from one or more cellulosic derivatives. In general, cellulosic derivatives include polymers such as cellulose acetate, cellulose acetate butyrate, 2-hydroxyethyl cellulose, cellulose acetate phthalate, cellulose acetate propionate, cellulose acetate trimellitate, and the like.

In one embodiment, the interference domain 57 is formed from cellulose acetate butyrate. Cellulose acetate butyrate with a molecular weight of about 10,000 daltons to about 75,000 daltons, preferably from about 15,000, 20,000, or 25,000 daltons to about 50,000, 55,000, 60,000, 65,000, or 70,000 daltons, and more preferably about 20,000 daltons is employed. In certain embodiments, however, higher or lower molecular weights can be preferred. Additionally, a casting solution or dispersion of cellulose acetate butyrate at a weight percent of about 15% to about 25%, preferably from about 15%, 16%, 17%, 18%, 19% to about 20%, 21%, 22%, 23%, 24% or 25%, and more preferably about 18% is preferred. Preferably, the casting solution includes a solvent or solvent system, for example an acetone:ethanol solvent system. Higher or lower concentrations can be preferred in certain embodiments. A plurality of layers of cellulose acetate butyrate can be advantageously combined to form the interference domain in some embodiments, for example, three layers can be employed. It can be desirable to employ a mixture of cellulose acetate butyrate components with different molecular weights in a single solution, or to deposit multiple layers of cellulose acetate butyrate from different solutions comprising cellulose acetate butyrate of different molecular weights, different concentrations, and/or different chemistries (e.g., functional groups). It can also be desirable to include additional substances in the casting solutions or dispersions, e.g., functionalizing agents, crosslinking agents, other polymeric substances, substances capable of modifying the hydrophilicity/hydrophobicity of the resulting layer, and the like.

In one alternative embodiment, the interference domain 57 is formed from cellulose acetate. Cellulose acetate with a molecular weight of about 30,000 daltons or less to about 100,000 daltons or more, preferably from about 35,000, 40,000, or 45,000 daltons to about 55,000, 60,000, 65,000, 70,000, 75,000, 80,000, 85,000, 90,000, or 95,000 daltons, and more preferably about 50,000 daltons is preferred. Additionally, a casting solution or dispersion of cellulose acetate at a weight percent of about 3% to about 10%, preferably from about 3.5%, 4.0%, 4.5%, 5.0%, 5.5%, 6.0%, or 6.5% to about 7.5%, 8.0%, 8.5%, 9.0%, or 9.5%, and more preferably about 8% is preferred. In certain embodiments, however, higher or lower molecular weights and/or cellulose acetate weight percentages can be preferred. It can be desirable to employ a mixture of cellulose acetates with molecular weights in a single solution, or to deposit multiple layers of cellulose acetate from different solutions comprising cellulose acetates of different molecular weights, different concentrations, or different chemistries (e.g., functional groups). It can also be desirable to include additional substances in the casting solutions or dispersions such as described in more detail above.

Layer(s) prepared from combinations of cellulose acetate and cellulose acetate butyrate, or combinations of layer(s) of cellulose acetate and layer(s) of cellulose acetate butyrate can also be employed to form the interference domain 57.

In some alternative embodiments, additional polymers, such as Nafion®, can be used in combination with cellulosic derivatives to provide equivalent and/or enhanced function of the interference domain 57. As one example, a 5 wt % Nafion® casting solution or dispersion can be used in combination with a 8 wt % cellulose acetate casting solution or dispersion, e.g., by dip coating at least one layer of cellulose acetate and subsequently dip coating at least one layer Nafion® onto a sensor such as described with reference to the preferred embodiments. Any number of coatings or layers formed in any order may be suitable for forming the interference domain of the preferred embodiments.

In some alternative embodiments, more than one cellulosic derivative can be used to form the interference domain 57 of the preferred embodiments. In general, the formation of the interference domain on a surface utilizes a solvent or solvent system in order to solvate the cellulosic derivative (or other polymer) prior to film formation thereon. In preferred embodiments, acetone and ethanol are used as solvents for cellulose acetate; however one skilled in the art appreciates the numerous solvents that are suitable for use with cellulosic derivatives (and other polymers). Additionally, one skilled in the art appreciates that the preferred relative amounts of solvent can be dependent upon the cellulosic derivative (or other polymer) used, its molecular weight, its method of deposition, its desired thickness, and the like. However, a percent solute of from about 1% to about 25% is preferably used to form the interference domain solution so as to yield an interference domain having the desired properties. The cellulosic derivative (or other polymer) used, its molecular weight, method of deposition, and desired thickness can be adjusted, depending upon one or more other of the parameters, and can be varied accordingly as is appreciated by one skilled in the art.

In some alternative embodiments, other polymer types that can be utilized as a base material for the interference domain 57 including polyurethanes, polymers having pendant ionic groups, and polymers having controlled pore size, for example. In one such alternative embodiment, the interference domain includes a thin, hydrophobic membrane that is non-swellable and restricts diffusion of low molecular weight species. The interference domain 57 is permeable to relatively low molecular weight substances, such as hydrogen peroxide, but restricts the passage of higher molecular weight substances, including glucose and ascorbic acid. Other systems and methods for reducing or eliminating interference species that can be applied to the membrane system of the preferred embodiments are described in U.S. Publication No. US-2005-0115832-A1, U.S. Publication No. US-2005-0176136-A1, U.S. Publication No. US-2005-0161346-A1, and U.S. Publication No. US-2005-0143635-A1. In some alternative embodiments, a distinct interference domain is not included (e.g., wherein interferants are resisted by other domains and/or wherein the sensing mechanism does not have interferants).

In one embodiment, the interference domain 57 is formed from a silicone polymer/hydrophobic-hydrophilic polymer blend. In one embodiment, The hydrophobic-hydrophilic polymer for use in the blend may be any suitable hydrophobic-hydrophilic polymer, including but not limited to components such as polyvinylpyrrolidone (PVP), polyhydroxyethyl methacrylate, polyvinylalcohol, polyacrylic acid, polyethers such as polyethylene glycol or polypropylene oxide, and copolymers thereof, including, for example, di-block, tri-block, alternating, random, comb, star, dendritic, and graft copolymers (block copolymers are discussed in U.S. Pat. Nos. 4,803,243 and 4,686,044, which are incorporated herein by reference). In one embodiment, the hydrophobic-hydrophilic polymer is a copolymer of poly(ethylene oxide) (PEO) and poly(propylene oxide) (PPO). Suitable such polymers include, but are not limited to, PEO-PPO diblock copolymers, PPO-PEO-PPO triblock copolymers, PEO-PPO-PEO triblock copolymers, alternating block copolymers of PEO-PPO, random copolymers of ethylene oxide and propylene oxide, and blends thereof. In some embodiments, the copolymers may be optionally substituted with hydroxy substituents. Commercially available examples of PEO and PPO copolymers include the PLURONIC® brand of polymers available from BASF®. In one embodiment, PLURONIC® F-127 is used. Other PLURONIC® polymers include PPO-PEO-PPO triblock copolymers (e.g., PLURONIC® R products). Other suitable commercial polymers include, but are not limited to, SYNPERONICS® products available from UNIQEMA®.

The silicone polymer for use in the silicone/hydrophobic-hydrophilic polymer blend may be any suitable silicone polymer. In some embodiments, the silicone polymer is a liquid silicone rubber that may be vulcanized using a metal-(e.g., platinum), peroxide-, heat-, ultraviolet-, or other radiation-catalyzed process. In some embodiments, the silicone polymer is a dimethyl- and methylhydrogen-siloxane copolymer. In some embodiments, the copolymer has vinyl substituents. In some embodiments, commercially available silicone polymers may be used. For example, commercially available silicone polymer precursor compositions may be used to prepare the blends, such as described below. In one embodiment, MED-4840 available from NUSIL® Technology LLC is used as a precursor to the silicone polymer used in the blend. MED-4840 consists of a 2-part silicone elastomer precursor including vinyl-functionalized dimethyl- and methylhydrogen-siloxane copolymers, amorphous silica, a platinum catalyst, a crosslinker, and an inhibitor. The two components may be mixed together and heated to initiate vulcanization, thereby forming an elastomeric solid material. Other suitable silicone polymer precursor systems include, but are not limited to, MED-2174 peroxide-cured liquid silicone rubber available from NUSIL® Technology LLC, SILASTIC® MDX4-4210 platinum-cured biomedical grade elastomer available from DOW CORNING®, and Implant Grade Liquid Silicone Polymer (durometers 10-50) available from Applied Silicone Corporation.

Silicone polymer/hydrophobic-hydrophilic polymer blends are described in more detail in U.S. patent application Ser. No. 11/404,417, entitled "SILICONE BASED MEMBRANES FOR USE IN IMPLANTABLE GLUCOSE SENSORS," filed on Apr. 14, 2006, which is incorporated herein by reference in its entirety.

In preferred embodiments, the interference domain 57 is deposited directly onto the electroactive surfaces of the sensor for a domain thickness of from about 0.05 micron or less to about 20 microns or more, more preferably from about 0.05, 0.1, 0.15, 0.2, 0.25, 0.3, 0.35, 0.4, 0.45, 0.5, 1, 1.5, 2, 2.5, 3, or 3.5 microns to about 4, 5, 6, 7, 8, 9, 10, 11, 12, 13, 14, 15, 16, 17, 18, 19, or 19.5 microns, and more preferably still from about 1, 1.5 or 2 microns to about 2.5 or 3 microns. Thicker membranes can also be desirable in certain embodiments, but thinner membranes are generally preferred because they have a lower impact on the rate of diffusion of hydrogen peroxide from the enzyme membrane to the electrodes.

In general, the membrane systems of the preferred embodiments can be formed and/or deposited on the exposed electroactive surfaces (e.g., one or more of the working and reference electrodes) using known thin film techniques (for example, casting, spray coating, drawing down, electro-depositing, dip coating, and the like), however casting or other known application techniques can also be utilized. Preferably, the interference domain is deposited by vapor deposition, spray coating, or dip coating. In one exemplary embodiment, the interference domain is formed by dip coating the sensor into an interference domain solution using an insertion rate of from about 20 inches/min to about 60 inches/min, preferably 40 inches/min, a dwell time of from about 0 minute to about 5 seconds, preferably 0 seconds, and a withdrawal rate of from about 20 inches/minute to about 60 inches/minute, preferably about 40 inches/minute, and curing (drying) the domain from about 1 minute to about 30 minutes, preferably from about 3 minutes to about 15 minutes (and can be accomplished at room temperature or under vacuum (e.g., 20 to 30 mmHg)). In one exemplary embodiment including cellulose acetate butyrate interference domain, a 3-minute cure (i.e., dry) time is preferred between each layer applied. In another exemplary embodiment employing a cellulose acetate interference domain, a 15 minute cure (i.e., dry) time is preferred between each layer applied.

The dip process can be repeated at least one time and up to 10 times or more. The preferred number of repeated dip processes depends upon the cellulosic derivative(s) used, their concentration, conditions during deposition (e.g., dipping) and the desired thickness (e.g., sufficient thickness to provide functional blocking of (or resistance to) certain interferents), and the like. In some embodiments, 1 to 3 microns may be preferred for the interference domain thickness; however, values outside of these can be acceptable or even desirable in certain embodiments, for example, depending upon viscosity and surface tension, as is appreciated by one skilled in the art. In one exemplary embodiment, an interference domain is formed from three layers of cellulose acetate butyrate. In another exemplary embodiment, an interference domain is formed from 10 layers of cellulose acetate. In alternative embodiments, the interference domain can be formed using any known method and combination of cellulose acetate and cellulose acetate butyrate, as will be appreciated by one skilled in the art.

In some embodiments, the electroactive surface can be cleaned prior to application of the interference domain 57. In some embodiments, the interference domain 57 of the preferred embodiments can be useful as a bioprotective or biocompatible domain, namely, a domain that interfaces with host tissue when implanted in an animal (e.g., a human) due to its stability and biocompatibility.

Enzyme Domain

In preferred embodiments, the membrane system further includes an enzyme domain 58 disposed more distally from the electroactive surfaces than the interference domain 57; however other configurations can be desirable. In the preferred embodiments, the enzyme domain provides an enzyme to catalyze the reaction of the analyte and its co-reactant. In the preferred embodiments of a glucose sensor, the enzyme domain includes glucose oxidase; however other oxidases, for example, galactose oxidase or uricase oxidase, can also be used.

For an enzyme-based electrochemical glucose sensor to perform well, the sensor's response is preferably limited by neither enzyme activity nor co-reactant concentration. Because enzymes, including glucose oxidase, are subject to deactivation as a function of time even in ambient conditions, this behavior is compensated for in forming the enzyme domain. Preferably, the enzyme domain is constructed of aqueous dispersions of colloidal polyurethane polymers including the enzyme. However, in alternative embodiments the enzyme domain is constructed from an oxygen enhancing material, for example, silicone, or fluorocarbon. Preferably, the enzyme is immobilized within the domain. See, e.g., U.S. patent application Ser. No. 10/896,639 filed on Jul. 21, 2004 and entitled "Oxygen Enhancing Membrane Systems for Implantable Device."

In one embodiment, the enzyme domain 58 is formed from a silicone polymer/hydrophobic-hydrophilic polymer blend. In one embodiment, The hydrophobic-hydrophilic polymer for use in the blend may be any suitable hydrophobic-hydrophilic polymer, including but not limited to components such as polyvinylpyrrolidone (PVP), polyhydroxyethyl methacrylate, polyvinylalcohol, polyacrylic acid, polyethers such as polyethylene glycol or polypropylene oxide, and copolymers thereof, including, for example, di-block, tri-block, alternating, random, comb, star, dendritic, and graft copolymers (block copolymers are discussed in U.S. Pat. Nos. 4,803,243 and 4,686,044, which are incorporated herein by reference). In one embodiment, the hydrophobic-hydrophilic polymer is a copolymer of poly (ethylene oxide) (PEO) and poly(propylene oxide) (PPO). Suitable such polymers include, but are not limited to, PEO-PPO diblock copolymers, PPO-PEO-PPO triblock copolymers, PEO-PPO-PEO triblock copolymers, alternating block copolymers of PEO-PPO, random copolymers of ethylene oxide and propylene oxide, and blends thereof. In some embodiments, the copolymers may be optionally substituted with hydroxy substituents. Commercially available examples of PEO and PPO copolymers include the PLURONIC® brand of polymers available from BASF®. In one embodiment, PLURONIC® F-127 is used. Other PLURONIC® polymers include PPO-PEO-PPO triblock copolymers (e.g., PLURONIC® R products). Other suitable commercial polymers include, but are not limited to, SYNPERONICS® products available from UNIQEMA®.

The silicone polymer for use in the silicone/hydrophobic-hydrophilic polymer blend may be any suitable silicone polymer. In some embodiments, the silicone polymer is a liquid silicone rubber that may be vulcanized using a metal- (e.g., platinum), peroxide-, heat-, ultraviolet-, or other radiation-catalyzed process. In some embodiments, the silicone polymer is a dimethyl- and methylhydrogen-siloxane copolymer. In some embodiments, the copolymer has vinyl substituents. In some embodiments, commercially available silicone polymers may be used. For example, commercially available silicone polymer precursor compositions may be used to prepare the blends, such as described below. In one embodiment, MED-4840 available from NUSIL® Technology LLC is used as a precursor to the silicone polymer used in the blend. MED-4840 consists of a 2-part silicone elastomer precursor including vinyl-functionalized dimethyl- and methylhydrogen-siloxane copolymers, amorphous silica, a platinum catalyst, a crosslinker, and an inhibitor. The two components may be mixed together and heated to initiate vulcanization, thereby forming an elastomeric solid material. Other suitable silicone polymer precursor systems include, but are not limited to, MED-2174 peroxide-cured liquid silicone rubber available from NUSIL® Technology LLC, SILASTIC® MDX4-4210 platinum-cured biomedical grade elastomer available from DOW CORNING®, and Implant Grade Liquid Silicone Polymer (durometers 10-50) available from Applied Silicone Corporation.

Silicone polymer/hydrophobic-hydrophilic polymer blends are described in more detail in U.S. patent application Ser. No. 11/404,417, entitled "SILICONE BASED MEMBRANES FOR USE IN IMPLANTABLE GLUCOSE SENSORS," filed on Apr. 14, 2006, which is incorporated herein by reference in its entirety.

In preferred embodiments, the enzyme domain is deposited onto the interference domain for a domain thickness of from about 0.05 micron or less to about 20 microns or more, more preferably from about 0.05, 0.1, 0.15, 0.2, 0.25, 0.3, 0.35, 0.4, 0.45, 0.5, 1, 1.5, 2, 2.5, 3, or 3.5 microns to about 4, 5, 6, 7, 8, 9, 10, 11, 12, 13, 14, 15, 16, 17, 18, 19, or 19.5 microns, and more preferably still from about 2, 2.5 or 3 microns to about 3.5, 4, 4.5, or 5 microns. However in some embodiments, the enzyme domain can be deposited directly onto the electroactive surfaces. Preferably, the enzyme domain is deposited by spray or dip coating. In one embodiment, the enzyme domain is formed by dip coating the interference domain coated sensor into an enzyme domain solution and curing the domain for from about 15 to about 30 minutes at a temperature of from about 40° C. to about 55° C. (and can be accomplished under vacuum (e.g., 20 to 30 mmHg)). In embodiments wherein dip coating is used to deposit the enzyme domain at room temperature, a preferred insertion rate of from about 0.25 inch per minute to about 3 inches per minute, with a preferred dwell time of from about 0.5 minutes to about 2 minutes, and a preferred withdrawal rate of from about 0.25 inch per minute to about 2 inches per minute provides a functional coating. However, values outside of those set forth above can be acceptable or even desirable in certain embodiments, for example, depending upon viscosity and surface tension, as is appreciated by one skilled in the art. In one embodiment, the enzyme domain is formed by dip coating two times (namely, forming two layers) in an enzyme domain solution and curing at 50° C. under vacuum for 20 minutes. However, in some embodiments, the enzyme domain can be formed by dip coating and/or spray coating one or more layers at a predetermined concentration of the coating solution, insertion rate, dwell time, withdrawal rate, and/or desired thickness.

Resistance Domain

In preferred embodiments, the membrane system includes a resistance domain 59 disposed more distal from the electroactive surfaces than the enzyme domain. Although the following description is directed to a resistance domain for a glucose sensor, the resistance domain can be modified for other analytes and co-reactants as well.

There exists a molar excess of glucose relative to the amount of oxygen in blood; that is, for every free oxygen molecule in extracellular fluid, there are typically more than 100 glucose molecules present (see Updike et al., Diabetes Care 5:207-21 (1982)). However, an immobilized enzyme-based glucose sensor employing oxygen as co-reactant is preferably supplied with oxygen in non-rate-limiting excess in order for the sensor to respond linearly to changes in glucose concentration, while not responding to changes in oxygen concentration. Specifically, when a glucose-monitoring reaction is oxygen limited, linearity is not achieved above minimal concentrations of glucose. Without a semipermeable membrane situated over the enzyme domain to control the flux of glucose and oxygen, a linear response to glucose levels can be obtained only for glucose concentrations of up to about 40 mg/dL. However, in a clinical setting, a linear response to glucose levels is desirable up to at least about 400 mg/dL.

The resistance domain includes a semipermeable membrane that controls the flux of oxygen and glucose to the underlying enzyme domain, preferably rendering oxygen in a non-rate-limiting excess. As a result, the upper limit of linearity of glucose measurement is extended to a much higher value than that which is achieved without the resistance domain. In one embodiment, the resistance domain exhibits an oxygen to glucose permeability ratio of from about 50:1 or less to about 400:1 or more, preferably about 200:1. As a result, one-dimensional reactant diffusion is adequate to provide excess oxygen at all reasonable glucose and oxygen concentrations found in the subcutaneous matrix (See Rhodes et al., Anal. Chem., 66:1520-1529 (1994)).

In alternative embodiments, a lower ratio of oxygen-to-glucose can be sufficient to provide excess oxygen by using a high oxygen solubility domain (for example, a silicone or fluorocarbon-based material or domain) to enhance the supply/transport of oxygen to the enzyme domain. If more oxygen is supplied to the enzyme, then more glucose can also be supplied to the enzyme without creating an oxygen rate-limiting excess. In alternative embodiments, the resistance domain is formed from a silicone composition, such as is described in U.S. Publication No. US-2005-0090607-A1.

In a preferred embodiment, the resistance domain includes a polyurethane membrane with both hydrophilic and hydrophobic regions to control the diffusion of glucose and oxygen to an analyte sensor, the membrane being fabricated easily and reproducibly from commercially available materials. A suitable hydrophobic polymer component is a polyurethane, or polyetherurethaneurea. Polyurethane is a polymer produced by the condensation reaction of a diisocyanate and a difunctional hydroxyl-containing material. A polyurethaneurea is a polymer produced by the condensation reaction of a diisocyanate and a difunctional amine-containing material. Preferred diisocyanates include aliphatic diisocyanates containing from about 4 to about 8 methylene units. Diisocyanates containing cycloaliphatic moieties can also be useful in the preparation of the polymer and copolymer components of the membranes of preferred embodiments. The material that forms the basis of the hydrophobic matrix of the resistance domain can be any of those known in the art as appropriate for use as membranes in sensor devices and as having sufficient permeability to allow relevant compounds to pass through it, for example, to allow an oxygen molecule to pass through the membrane from the sample under examination in order to reach the active enzyme or electrochemical electrodes. Examples of materials which can be used to make non-polyurethane type membranes include vinyl polymers, polyethers, polyesters, polyamides, inorganic polymers such as polysiloxanes and polycarbosiloxanes, natural polymers such as cellulosic and protein based materials, and mixtures or combinations thereof.

In a preferred embodiment, the hydrophilic polymer component is polyethylene oxide. For example, one useful hydrophobic-hydrophilic copolymer component is a polyurethane polymer that includes about 20% hydrophilic polyethylene oxide. The polyethylene oxide portions of the copolymer are thermodynamically driven to separate from the hydrophobic portions of the copolymer and the hydrophobic polymer component. The 20% polyethylene oxide-based soft segment portion of the copolymer used to form the final blend affects the water pick-up and subsequent glucose permeability of the membrane.

In one preferred embodiment, the resistance domain 59 is formed from a silicone polymer/hydrophobic-hydrophilic polymer blend. In one embodiment, The hydrophobic-hydrophilic polymer for use in the blend may be any suitable hydrophobic-hydrophilic polymer, including but not limited to components such as polyvinylpyrrolidone (PVP), polyhydroxyethyl methacrylate, polyvinylalcohol, polyacrylic acid, polyethers such as polyethylene glycol or polypropylene oxide, and copolymers thereof, including, for example, di-block, tri-block, alternating, random, comb, star, dendritic, and graft copolymers (block copolymers are discussed in U.S. Pat. Nos. 4,803,243 and 4,686,044, which are incorporated herein by reference). In one embodiment, the hydrophobic-hydrophilic polymer is a copolymer of poly (ethylene oxide) (PEO) and poly(propylene oxide) (PPO). Suitable such polymers include, but are not limited to, PEO-PPO diblock copolymers, PPO-PEO-PPO triblock copolymers, PEO-PPO-PEO triblock copolymers, alternating block copolymers of PEO-PPO, random copolymers of ethylene oxide and propylene oxide, and blends thereof. In some embodiments, the copolymers may be optionally substituted with hydroxy substituents. Commercially available examples of PEO and PPO copolymers include the PLURONIC® brand of polymers available from BASF®. In one embodiment, PLURONIC® F-127 is used. Other PLURONIC® polymers include PPO-PEO-PPO triblock copolymers (e.g., PLURONIC® R products). Other suitable commercial polymers include, but are not limited to, SYNPERONICS® products available from UNIQEMA®.

The silicone polymer for use in the silicone/hydrophobic-hydrophilic polymer blend may be any suitable silicone polymer. In some embodiments, the silicone polymer is a liquid silicone rubber that may be vulcanized using a metal- (e.g., platinum), peroxide-, heat-, ultraviolet-, or other radiation-catalyzed process. In some embodiments, the silicone polymer is a dimethyl- and methylhydrogen-siloxane copolymer. In some embodiments, the copolymer has vinyl substituents. In some embodiments, commercially available silicone polymers may be used. For example, commercially available silicone polymer precursor compositions may be used to prepare the blends, such as described below. In one embodiment, MED-4840 available from NUSIL® Technology LLC is used as a precursor to the silicone polymer used in the blend. MED-4840 consists of a 2-part silicone elastomer precursor including vinyl-functionalized dimethyl- and methylhydrogen-siloxane copolymers, amorphous silica, a platinum catalyst, a crosslinker, and an inhibitor. The two components may be mixed together and heated to initiate vulcanization, thereby forming an elastomeric solid material. Other suitable silicone polymer precursor systems include, but are not limited to, MED-2174 peroxide-cured liquid silicone rubber available from NUSIL® Technology LLC, SILASTIC® MDX4-4210 platinum-cured biomedical grade elastomer available from DOW CORNING®, and Implant Grade Liquid Silicone Polymer (durometers 10-50) available from Applied Silicone Corporation.

Silicone polymer/hydrophobic-hydrophilic polymer blends are described in more detail in U.S. patent application Ser. No. 11/404,417, entitled "SILICONE BASED MEMBRANES FOR USE IN IMPLANTABLE GLUCOSE SENSORS," filed on Apr. 14, 2006, which is incorporated herein by reference in its entirety.

In preferred embodiments, the resistance domain is deposited onto the enzyme domain to yield a domain thickness of from about 0.05 microns or less to about 20 microns or more, more preferably from about 0.05, 0.1, 0.15, 0.2, 0.25, 0.3, 0.35, 0.4, 0.45, 0.5, 1, 1.5, 2, 2.5, 3, or 3.5 microns to about 4, 5, 6, 7, 8, 9, 10, 11, 12, 13, 14, 15, 16, 17, 18, 19, or 19.5 microns, and more preferably still from about 2, 2.5 or 3 microns to about 3.5, 4, 4.5, or 5 microns. Preferably, the resistance domain is deposited onto the enzyme domain by vapor deposition, spray coating, or dip coating. In one preferred embodiment, spray coating is the preferred deposition technique. The spraying process atomizes and mists the solution, and therefore most or all of the solvent is evaporated prior to the coating material settling on the underlying domain, thereby minimizing contact of the solvent with the enzyme.

In another preferred embodiment, physical vapor deposition (e.g., ultrasonic vapor deposition) is used for coating one or more of the membrane domain(s) onto the electrodes, wherein the vapor deposition apparatus and process include an ultrasonic nozzle that produces a mist of micro-droplets in a vacuum chamber. In these embodiments, the micro-droplets move turbulently within the vacuum chamber, isotropically impacting and adhering to the surface of the substrate. Advantageously, vapor deposition as described above can be implemented to provide high production throughput of membrane deposition processes (e.g., at least about 20 to about 200 or more electrodes per chamber), greater consistency of the membrane on each sensor, and increased uniformity of sensor performance, for example, as described below.

In some embodiments, depositing the resistance domain (for example, as described in the preferred embodiments above) includes formation of a membrane system that substantially blocks or resists ascorbate (a known electrochemical interferant in hydrogen peroxide-measuring glucose sensors). While not wishing to be bound by theory, it is believed that during the process of depositing the resistance domain as described in the preferred embodiments, a structural morphology is formed that is characterized in that ascorbate does not substantially permeate therethrough.

In a preferred embodiment, the resistance domain is deposited on the enzyme domain by spray coating a solution of from about 1 wt. % to about 5 wt. % polymer and from about 95 wt. % to about 99 wt. % solvent. In spraying a solution of resistance domain material, including a solvent, onto the enzyme domain, it is desirable to mitigate or substantially reduce any contact with enzyme of any solvent in the spray solution that can deactivate the underlying enzyme of the enzyme domain. Tetrahydrofuran (THF) is one solvent that minimally or negligibly affects the enzyme of the enzyme domain upon spraying. Other solvents can also be suitable for use, as is appreciated by one skilled in the art.

Although a variety of spraying or deposition techniques can be used, spraying the resistance domain material and rotating the sensor at least one time by 180° can typically provide adequate coverage by the resistance domain. Spraying the resistance domain material and rotating the sensor at least two times by 120° provides even greater coverage (one layer of 360° coverage), thereby ensuring resistivity to glucose, such as is described in more detail above.

In preferred embodiments, the resistance domain is spray coated and subsequently cured for a time of from about 15 minutes to about 90 minutes at a temperature of from about 40° C. to about 60° C. (and can be accomplished under vacuum (e.g., from 20 to 30 mmHg)). A cure time of up to about 90 minutes or more can be advantageous to ensure complete drying of the resistance domain.

In one embodiment, the resistance domain is formed by spray coating at least six layers (namely, rotating the sensor seventeen times by 120° for at least six layers of 360° coverage) and curing at 50° C. under vacuum for 60 minutes. However, the resistance domain can be formed by dip coating or spray coating any layer or plurality of layers, depending upon the concentration of the solution, insertion rate, dwell time, withdrawal rate, and/or the desired thickness of the resulting film. Additionally, curing in a convention oven can also be employed.

In certain embodiments, a variable frequency microwave oven can be used to cure the membrane domains/layers. In general, microwave ovens directly excite the rotational mode of solvents. Consequently, microwave ovens cure coatings from the inside out rather than from the outside in as with conventional convection ovens. This direct rotational mode excitation is responsible for the typically observed "fast" curing within a microwave oven. In contrast to conventional microwave ovens, which rely upon a fixed frequency of emission that can cause arcing of dielectric (metallic) substrates if placed within a conventional microwave oven, Variable Frequency Microwave (VFM) ovens emit thousands of frequencies within 100 milliseconds, which substantially eliminates arcing of dielectric substrates. Consequently, the membrane domains/layers can be cured even after deposition on metallic electrodes as described herein. While not wishing to be bound by theory, it is believe that VFM curing can increase the rate and completeness of solvent evaporation from a liquid membrane solution applied to a sensor, as compared to the rate and completeness of solvent evaporation observed for curing in conventional convection ovens.

In certain embodiments, VFM is can be used together with convection oven curing to further accelerate cure time. In some sensor applications wherein the membrane is cured prior to application on the electrode (see, for example, U.S. Publication No. US-2005-0245799-A1, which is incorporated herein by reference in its entirety), conventional microwave ovens (e.g., fixed frequency microwave ovens) can be used to cure the membrane layer.

Bioprotective Domain

The bioprotective domain, if present, is positioned less distal to the implantable device than the cell disruptive layer, and can be resistant to cellular attachment, impermeable to cells, and/or is composed of a biostable material. When the bioprotective domain is resistant to cellular attachment (for example, attachment by inflammatory cells, such as macrophages, which are therefore kept a sufficient distance from other domains, for example, the enzyme domain), hypochlorite and other oxidizing species are short-lived chemical species in vivo, and biodegradation does not occur. Additionally, the materials preferred for forming the bioprotective domain may be resistant to the effects of these oxidative species and have thus been termed biodurable. See, for example, U.S. Pat. No. 6,702,857, filed Jul. 27, 2001, and entitled "MEMBRANE FOR USE WITH IMPLANTABLE DEVICES" and U.S. patent application Ser. No. 10/647,065, filed Aug. 22, 2003, published in Publication No. 20050112169 and entitled, "POROUS MEMBRANES FOR USE WITH IMPLANTABLE DEVICES," both of which are incorporated herein by reference in their entirety.

In one embodiment, bioprotective domain is formed from high oxygen soluble materials such as polymers formed from silicone, fluorocarbons, perfluorocarbons, or the like. In one embodiment, the cell impermeable domain is formed from a silicone composition with a hydrophile such as such as polyethylene glycol, propylene glycol, pyrrolidone, esters, amides, carbonates, or polypropylene glycol covalently incorporated or grafted therein. In still other embodiments, the bioprotective domain is formed from a monomer, polymer, copolymer, or blend including one or more of: lactic acid, glycolic acid, anhydrides, phospazenes, vinyl alcohol, ethylene vinyl alcohol, acetates, ϵ-caprolactone, β-hydroxybutyrate, γ-ethyl glutamate, DTH iminocarbonate, Bisphenol A iminocarbonate, sebacic acid, hexadecanoic acid, saccharides, chitosan, hydyoxyethyl methacrylate (HEMA), ceramics, hyaluronic acid (HA), collagen, gelatin, starches, hydroxy apatite, calcium phosphates, bioglasses, amino acid sequences, proteins, glycoproteins, protein fragments, agarose, fibrin, n-butylene, isobutylene, dioxanone, nylons, vinyl chlorides, amides, ethylenes, n-butyl methacrylate (BMA), metal matrix composites (MMCs), metal oxides (e.g. aluminum), DETOSU-1,6 HD-t-CDM ortho ester, styrene, and plasma treated surfaces of any of the above.

In one preferred embodiment, the bioprotective domain is formed from a silicone polymer/hydrophobic-hydrophilic polymer blend. In one embodiment, The hydrophobic-hydrophilic polymer for use in the blend may be any suitable hydrophobic-hydrophilic polymer, including but not limited to components such as polyvinylpyrrolidone (PVP), polyhydroxyethyl methacrylate, polyvinylalcohol, polyacrylic acid, polyethers such as polyethylene glycol or polypropylene oxide, and copolymers thereof, including, for example, di-block, tri-block, alternating, random, comb, star, dendritic, and graft copolymers (block copolymers are discussed in U.S. Pat. Nos. 4,803,243 and 4,686,044, which are incorporated herein by reference). In one embodiment, the hydrophobic-hydrophilic polymer is a copolymer of poly(ethylene oxide) (PEO) and poly(propylene oxide) (PPO). Suitable such polymers include, but are not limited to, PEO-PPO diblock copolymers, PPO-PEO-PPO triblock copolymers, PEO-PPO-PEO triblock copolymers, alternating block copolymers of PEO-PPO, random copolymers of ethylene oxide and propylene oxide, and blends thereof. In some embodiments, the copolymers may be optionally substituted with hydroxy substituents. Commercially available examples of PEO and PPO copolymers include the PLURONIC® brand of polymers available from BASF®. In one embodiment, PLURONIC® F-127 is used. Other PLURONIC® polymers include PPO-PEO-PPO triblock copolymers (e.g., PLURONIC® R products). Other suitable commercial polymers include, but are not limited to, SYN-PERONICS® products available from UNIQEMA®.

The silicone polymer for use in the silicone/hydrophobic-hydrophilic polymer blend may be any suitable silicone polymer. In some embodiments, the silicone polymer is a liquid silicone rubber that may be vulcanized using a metal- (e.g., platinum), peroxide-, heat-, ultraviolet-, or other radiation-catalyzed process. In some embodiments, the silicone polymer is a dimethyl- and methylhydrogen-siloxane copolymer. In some embodiments, the copolymer has vinyl substituents. In some embodiments, commercially available silicone polymers may be used. For example, commercially available silicone polymer precursor compositions may be used to prepare the blends, such as described below. In one embodiment, MED-4840 available from NUSIL® Technology LLC is used as a precursor to the silicone polymer used in the blend. MED-4840 consists of a 2-part silicone elastomer precursor including vinyl-functionalized dimethyl- and methylhydrogen-siloxane copolymers, amorphous silica, a platinum catalyst, a crosslinker, and an inhibitor. The two components may be mixed together and heated to initiate vulcanization, thereby forming an elastomeric solid material. Other suitable silicone polymer precursor systems include, but are not limited to, MED-2174 peroxide-cured liquid silicone rubber available from NUSIL® Technology LLC, SILASTIC® MDX4-4210 platinum-cured biomedical grade elastomer available from DOW CORNING®, and Implant Grade Liquid Silicone Polymer (durometers 10-50) available from Applied Silicone Corporation.

Silicone polymer/hydrophobic-hydrophilic polymer blends are described in more detail in U.S. patent application Ser. No. 11/404,417, entitled "SILICONE BASED MEMBRANES FOR USE IN IMPLANTABLE GLUCOSE SENSORS," filed on Apr. 14, 2006, which is incorporated herein by reference in its entirety.

It is advantageous that the bioprotective domain have both high oxygen and aqueous analyte solubility so that sufficient reactants reach the enzyme layer. Accordingly, in one embodiment, the concentration of hydrophobic-hydrophilic polymer (e.g., PLURONIC® F-127) relative to silicone polymer (e.g., MED-4840) is relatively high, e.g., from about 10% to about 30% in the bioprotective layer 42. In one embodiment, the concentration of hydrophobic-hydrophilic polymer is from about 15% to about 25% (e.g., about 20%).

In preferred embodiments, the thickness of the bioprotective domain is from about 10 or 15 microns or less to about 125, 150, 175, 200 or 250 microns or more. In more preferred embodiments, the thickness of the bioprotective domain is from about 20, 25, 30, or 35 microns to about 60, 65, 70, 75, 80, 85, 90, 95, or 100 microns. In even more preferred embodiments, the bioprotective domain is from about 20 or 25 microns to about 50, 55, or 60 microns thick.

Electronics

The electrodes of the sensing biointerfaces described above may be electrically coupled at their ends to contacts (or the like) on the sensor electronics, which are connected to a power source. In some embodiments, the sensing biointerface and accompanying electronics are packaged in a complete sensor device that can be implanted (e.g., transcutaneously or wholly) into a host. In one embodiment, the sensing biointerface is stretched linearly between two supports on the complete sensor device. In one embodiment, the sensing biointerface is coiled or looped to reduce the footprint of the device. However, whatever configuration of sensing biointerface is used, it is advantageous to allow both (or numerous) sides of the biointerface to contact tissue.

In some embodiments, the biocompatible matrix is electrically coupled to the sensor electronics and includes a power source. Namely, the sensor electronics comprise contacts (or the like) configured to contact the electrodes of the biocompatible matrix. In one embodiment, a portion of the electrodes of the biocompatible matrix are exposed at their ends and configured to engage contacts on the sensor electronics device body. Alternately, the electrodes are hard-wired into the sensor electronics to provide electrical coupling. The power source is connected to the sensor electronics and includes a battery, inductor, or the like, as is appreciated by one skilled in the art.

Figure 15:
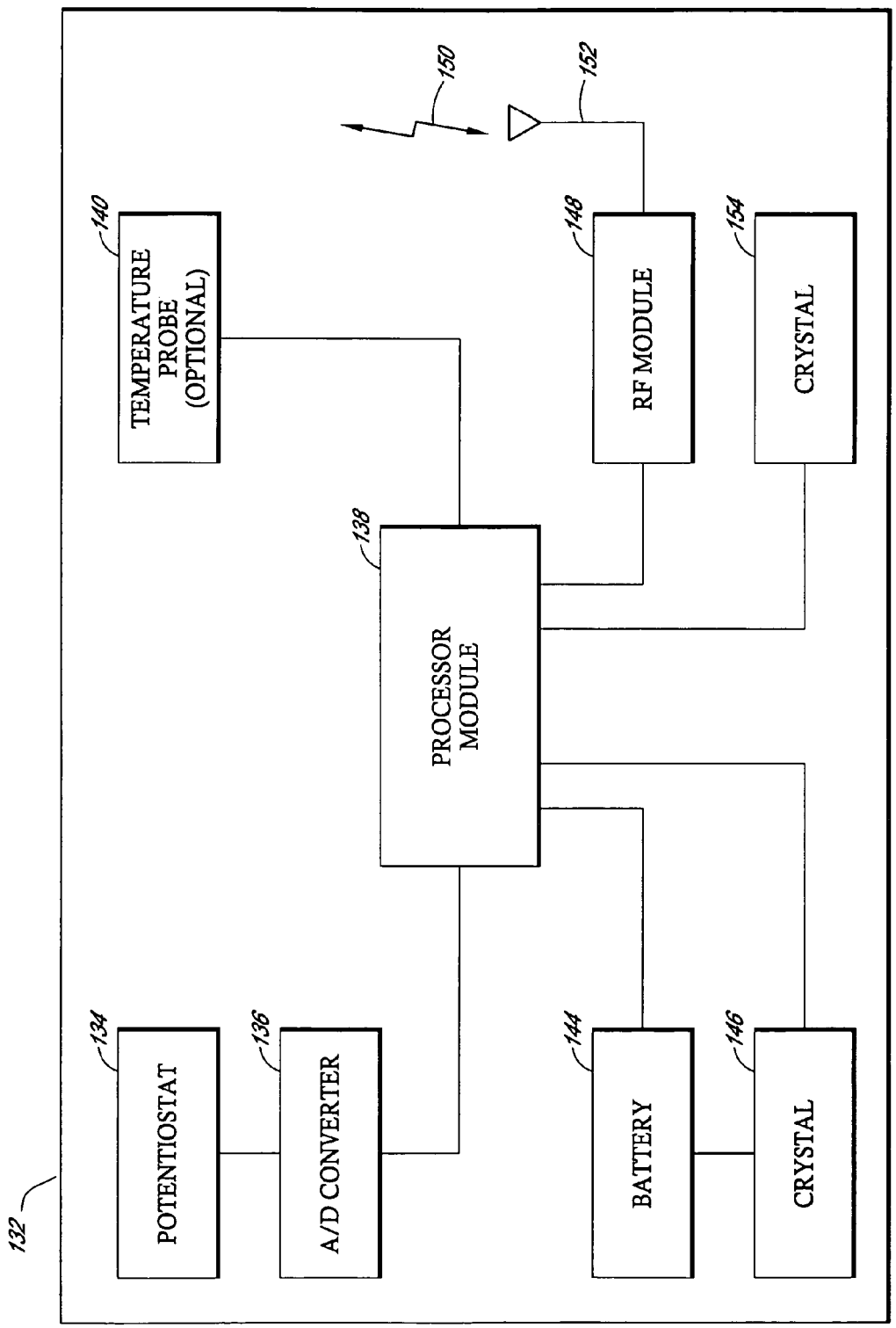
FIG. 15 depicts a block diagram of the sensor electronics in one embodiment.

FIG. 15 is a block diagram that illustrates the sensor electronics in one embodiment. In this embodiment, a potentiostat 134 is shown, which is operably connected to an electrode system (such as described above) and provides a voltage to the electrodes, which biases the sensor to enable measurement of an current signal indicative of the analyte concentration in the host (also referred to as the analog portion). In some embodiments, the potentiostat includes a resistor (not shown) that translates the current into voltage. In some alternative embodiments, a current to frequency converter is provided that is configured to continuously integrate the measured current, for example, using a charge counting device.

An A/D converter 136 digitizes the analog signal into a digital signal, also referred to as "counts" for processing. Accordingly, the resulting raw data stream in counts, also referred to as raw sensor data, is directly related to the current measured by the potentiostat 134.

A processor module 138 includes the central control unit that controls the processing of the sensor electronics 132. In some embodiments, the processor module includes a microprocessor, however a computer system other than a microprocessor can be used to process data as described herein, for example an ASIC can be used for some or all of the sensor's central processing. The processor typically provides semi-permanent storage of data, for example, storing data such as sensor identifier (ID) and programming to process data streams (for example, programming for data smoothing and/or replacement of signal artifacts such as is described in U.S. Publication No. US-2005-0043598-A1). The processor additionally can be used for the system's cache memory, for example for temporarily storing recent sensor data. In some embodiments, the processor module comprises memory storage components such as ROM, RAM, dynamic-RAM, static-RAM, non-static RAM, EEPROM, rewritable ROMs, flash memory, or the like.

In some embodiments, the processor module comprises a digital filter, for example, an infinite impulse response (IIR) or finite impulse response (FIR) filter, configured to smooth the raw data stream from the A/D converter. Generally, digital filters are programmed to filter data sampled at a predetermined time interval (also referred to as a sample rate). In some embodiments, wherein the potentiostat is configured to measure the analyte at discrete time intervals, these time intervals determine the sample rate of the digital filter. In some alternative embodiments, wherein the potentiostat is configured to continuously measure the analyte, for example, using a current-to-frequency converter as described above, the processor module can be programmed to request a digital value from the A/D converter at a predetermined time interval, also referred to as the acquisition time. In these alternative embodiments, the values obtained by the processor are advantageously averaged over the acquisition time due the continuity of the current measurement. Accordingly, the acquisition time determines the sample rate of the digital filter. In preferred embodiments, the processor module is configured with a programmable acquisition time, namely, the predetermined time interval for requesting the digital value from the A/D converter is programmable by a user within the digital circuitry of the processor module. An acquisition time of from about 2 seconds to about 512 seconds is preferred; however any acquisition time can be programmed into the processor module. A programmable acquisition time is advantageous in optimizing noise filtration, time lag, and processing/battery power.

Preferably, the processor module is configured to build the data packet for transmission to an outside source, for example, an RF transmission to a receiver. Generally, the data packet comprises a plurality of bits that can include a preamble, a unique identifier identifying the electronics unit, the receiver, or both, (e.g., sensor ID code), data (e.g., raw data, filtered data, and/or an integrated value) and/or error detection or correction. Preferably, the data (transmission) packet has a length of from about 8 bits to about 128 bits, preferably about 48 bits; however, larger or smaller packets can be desirable in certain embodiments. The processor module can be configured to transmit any combination of raw and/or filtered data. In one exemplary embodiment, the transmission packet contains a fixed preamble, a unique ID of the electronics unit, a single five-minute average (e.g., integrated) sensor data value, and a cyclic redundancy code (CRC).

In some embodiments, the processor module further comprises a transmitter portion that determines the transmission interval of the sensor data to a receiver, or the like. In some embodiments, the transmitter portion, which determines the interval of transmission, is configured to be programmable. In one such embodiment, a coefficient can be chosen (e.g., a number of from about 1 to about 100, or more), wherein the coefficient is multiplied by the acquisition time (or sampling rate), such as described above, to define the transmission interval of the data packet. Thus, in some embodiments, the transmission interval is programmable from about 2 seconds to about 850 minutes, more preferably from about 30 second to about 5 minutes; however, any transmission interval can be programmable or programmed into the processor module. However, a variety of alternative systems and methods for providing a programmable transmission interval can also be employed. By providing a programmable transmission interval, data transmission can be customized to meet a variety of design criteria (e.g., reduced battery consumption, timeliness of reporting sensor values, etc.)

Conventional glucose sensors measure current in the nanoAmp range. In some embodiments, the preferred embodiments are configured to measure the current flow in the picoAmp range, and in some embodiments, femtoAmps. Namely, for every unit (mg/dL) of glucose measured, at least one picoAmp of current is measured. Preferably, the analog portion of the A/D converter 136 is configured to continuously measure the current flowing at the working electrode and to convert the current measurement to digital values representative of the current. In one embodiment, the current flow is measured by a charge counting device (e.g., a capacitor). Preferably, a charge counting device provides a value (e.g., digital value) representative of the current flow integrated over time (e.g., integrated value). In some embodiments, the value is integrated over a few seconds, a few minutes, or longer. In one exemplary embodiment, the value is integrated over 5 minutes; however, other integration periods can be chosen. Thus, a signal is provided, whereby a high sensitivity maximizes the signal received by a minimal amount of measured hydrogen peroxide (e.g., minimal glucose requirements without sacrificing accuracy even in low glucose ranges), reducing the sensitivity to oxygen limitations in vivo (e.g., in oxygen-dependent glucose sensors).

In some embodiments, the electronics unit is programmed with a specific ID, which is programmed (automatically or by the user) into a receiver to establish a secure wireless communication link between the electronics unit and the receiver. Preferably, the transmission packet is Manchester encoded; however, a variety of known encoding techniques can also be employed.

A battery 144 is operably connected to the sensor electronics 132 and provides the power for the sensor. In one embodiment, the battery is a lithium manganese dioxide battery; however, any appropriately sized and powered battery can be used (for example, AAA, nickel-cadmium, zinc-carbon, alkaline, lithium, nickel-metal hydride, lithium-ion, zinc-air, zinc-mercury oxide, silver-zinc, and/or hermetically-sealed). In some embodiments, the battery is rechargeable, and/or a plurality of batteries can be used to power the system. The sensor can be transcutaneously powered via an inductive coupling, for example. In some embodiments, a quartz crystal 96 is operably connected to the processor 138 and maintains system time for the computer system as a whole, for example for the programmable acquisition time within the processor module.

Optional temperature probe 140 is shown, wherein the temperature probe is located on the electronics assembly or the glucose sensor itself. The temperature probe can be used to measure ambient temperature in the vicinity of the glucose sensor. This temperature measurement can be used to add temperature compensation to the calculated glucose value.

An RF module 148 is operably connected to the processor 138 and transmits the sensor data from the sensor to a receiver within a wireless transmission 150 via antenna 152. In some embodiments, a second quartz crystal 154 provides the time base for the RF carrier frequency used for data transmissions from the RF transceiver. In some alternative embodiments, however, other mechanisms, such as optical, infrared radiation (IR), ultrasonic, or the like, can be used to transmit and/or receive data.

In the RF telemetry module of the preferred embodiments, the hardware and software are designed for low power requirements to increase the longevity of the device (for example, to enable a life of from about 3 to about 24 months, or more) with maximum RF transmittance from the in vivo environment to the ex vivo environment for wholly implantable sensors (for example, a distance of from about one to ten meters or more). Preferably, a high frequency carrier signal of from about 402 MHz to about 433 MHz is employed in order to maintain lower power requirements. In some embodiments, the RF module employs a one-way RF communication link to provide a simplified ultra low power data transmission and receiving scheme. The RF transmission can be OOK or FSK modulated, preferably with a radiated transmission power (EIRP) fixed at a single power level of typically less than about 100 microwatts, preferably less than about 75 microwatts, more preferably less than about 50 microwatts, and most preferably less than about 25 microwatts.

Additionally, in wholly implantable devices, the carrier frequency may be adapted for physiological attenuation levels, which is accomplished by tuning the RF module in a simulated in vivo environment to ensure RF functionality after implantation; accordingly, the preferred glucose sensor can sustain sensor function for 3 months, 6 months, 12 months, or 24 months or more.

The above description of sensor electronics associated with the electronics unit is applicable to a variety of continuous analyte sensors, such as non-invasive, minimally invasive, and/or invasive (e.g., transcutaneous and wholly implantable) sensors. For example, the sensor electronics and data processing as well as the receiver electronics and data processing described below can be incorporated into the wholly implantable glucose sensor disclosed in U.S. Publication No. US-2005-0245799-A1 and U.S. patent application Ser. No. 10/885,476 filed Jul. 6, 2004 and entitled, "SYSTEMS AND METHODS FOR MANUFACTURE OF AN ANALYTE-MEASURING DEVICE INCLUDING A MEMBRANE SYSTEM."

Methods and devices that are suitable for use in conjunction with aspects of the preferred embodiments are disclosed in U.S. Pat. No. 4,994,167; U.S. Pat. No. 4,757,022; U.S. Pat. No. 6,001,067; U.S. Pat. No. 6,741,877; U.S. Pat. No. 6,702,857; U.S. Pat. No. 6,558,321; U.S. Pat. No. 6,931,327; and U.S. Pat. No. 6,862,465.

Methods and devices that are suitable for use in conjunction with aspects of the preferred embodiments are disclosed in U.S. Publication No. US-2005-0176136-A1; U.S. Publication No. US-2005-0251083-A1; U.S. Publication No. US-2005-0143635-A1; U.S. Publication No. US-2005-0181012-A1; U.S. Publication No. US-2005-0177036-A1; U.S. Publication No. US-2005-0124873-A1; U.S. Publication No. US-2005-0051440-A1; U.S. Publication No. US-2005-0115832-A1; U.S. Publication No. US-2005-0245799-A1; U.S. Publication No. US-2005-0245795-A1; U.S. Publication No. US-2005-0242479-A1; U.S. Publication No. US-2005-0182451-A1; U.S. Publication No. US-2005-0056552-A1; U.S. Publication No. US-2005-0192557-A1; U.S. Publication No. US-2005-0154271-A1; U.S. Publication No. US-2004-0199059-A1; U.S. Publication No. US-2005-0054909-A1; U.S. Publication No. US-2005-0112169-A1; U.S. Publication No. US-2005-0051427-A1; U.S. Publication No. US-2003-0032874; U.S. Publication No. US-2005-0103625-A1; U.S. Publication No. US-2005-0203360-A1; U.S. Publication No. US-2005-0090607-A1; U.S. Publication No. US-2005-0187720-A1; U.S. Publication No. US-2005-0161346-A1; U.S. Publication No. US-2006-0015020-A1; U.S. Publication No. US-2005-0043598-A1; U.S. Publication No. US-2003-0217966-A1; U.S. Publication No. US-2005-0033132-A1; U.S. Publication No. US-2005-0031689-A1; U.S. Publication No. US-2004-0045879-A1; U.S. Publication No. US-2004-0186362-A1; U.S. Publication No. US-2005-0027463-A1; U.S. Publication No. US-2005-0027181-A1; U.S. Publication No. US-2005-0027180-A1; U.S. Publication No. US-2006-0020187-A1; U.S. Publication No. US-2006-0036142-A1; U.S. Publication No. US-2006-0020192-A1; U.S. Publication No. US-2006-0036143-A1; U.S. Publication No. US-2006-0036140-A1; U.S. Publication No. US-2006-0019327-A1; U.S. Publication No. US-2006-0020186-A1; U.S. Publication No. US-2006-0020189-A1; U.S. Publication No. US-2006-0036139-A1; U.S. Publication No. US-2006-0020191-A1; U.S. Publication No. US-2006-0020188-A1; U.S. Publication No. US-2006-0036141-A1; U.S. Publication No. US-2006-0020190-A1; U.S. Publication No. US-2006-0036145-A1; U.S. Publication No. US-2006-0036144-A1; and U.S. Publication No. US-2006-0016700A1.

Methods and devices that are suitable for use in conjunction with aspects of the preferred embodiments are disclosed in U.S. application Ser. No. 09/447,227 filed Nov. 22, 1999 and entitled "DEVICE AND METHOD FOR DETERMINING ANALYTE LEVELS"; U.S. application Ser. No. 11/280,672 filed Nov. 16, 2005, and entitled "TECHNIQUES TO IMPROVE POLYURETHANE MEMBRANES FOR IMPLANTABLE GLUCOSE SENSORS"; U.S. application Ser. No. 11/280,102 filed Nov. 16, 2005, and entitled "TECHNIQUES TO IMPROVE POLYURETHANE MEMBRANES FOR IMPLANTABLE GLUCOSE SENSORS"; U.S. application Ser. No. 11/201,445 filed Aug. 10, 2005 and entitled "SYSTEM AND METHODS FOR PROCESSING ANALYTE SENSOR DATA"; U.S. application Ser. No. 11/335,879 filed Jan. 18, 2006 and entitled "CELLULOSIC-BASED INTERFERENCE DOMAIN FOR AN ANALYTE SENSOR"; U.S. application Ser. No. 11/334,876 filed Jan. 18, 2006 and entitled "TRANSCUTANEOUS ANALYTE SENSOR"; U.S. application Ser. No. 11/333,837 filed Jan. 17, 2006 and entitled "LOW OXYGEN IN VIVO ANALYTE SENSOR".

In one embodiment of the present invention, a method is provided for detecting an analyte, such as glucose, using an implantable sensing biointerface such as described herein. The implantable sensing biointerface can be surgically implanted at a tissue site in a host. Tissue can then be allowed to grow in the passageways in the matrix of the sensing biointerface. Finally, the analyte can be detected at a working electrode disposed within the sensing biointerface matrix, with or without the aid of a membrane system disposed on the working electrode.

The term "host" as used herein is a broad term, and is to be given its ordinary and customary meaning to a person of ordinary skill in the art (and is not to be limited to a special or customized meaning), and refers without limitation to a mammal. In one embodiment, the host is a human.

The use of the sensing biointerfaces described herein has several advantages. First, because the biointerface can be constructed in the form of a thin membrane, it can be implanted with much less trauma to surrounding tissue. Furthermore, the thinness of the biointerface can promote rapid in-growth of tissue and thus, allow the sensor to reach optimal detecting condition faster. The fact that tissue in-growth can occur from both sides of the biointerface also promotes fast start-up and an improvement in the quality of detection. The small scale of the passageways within the biointerface allows tissue, including vasculature, to grow closer to the electrodes than would otherwise be possible. Thus the time lag between a change in analyte levels in the blood stream and detection of those levels is decreased because the transport distance of the analyte from blood vessels to the electrodes is shorter.

The term "substantially" as used herein is a broad term, and is to be given its ordinary and customary meaning to a person of ordinary skill in the art (and is not to be limited to a special or customized meaning), and refers without limitation to being largely but not necessarily wholly that which is specified.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

What is claimed is:

1. A transcutaneous continuous glucose sensor system, comprising:
   a substantially planar sensor, the sensor comprising:
      a first non-conductive layer;
      a first conductive layer comprising a first electrode, wherein the first conductive layer is disposed over the first non-conductive layer;
      a second non-conductive layer disposed over the first conductive layer;
      a second conductive layer comprising a second electrode, wherein the second conductive layer is disposed over the second non-conductive layer;
      a third non-conductive layer disposed over the second conductive layer;
      a third conductive layer comprising a third electrode, wherein the third conductive layer is disposed over the third non-conductive layer;
      wherein at least one of the first electrode, second electrode, or third electrode is a working electrode configured to measure a signal indicative of a glucose concentration;
   a membrane disposed on at least a portion of the sensor; and
   electronics electrically coupled to the working electrode.

2. The sensor of claim 1, wherein the membrane comprises an enzyme.

3. The sensor of claim 2, wherein the membrane further comprises a resistance domain disposed over the enzyme.

4. The sensor of claim 1, wherein the membrane further comprises a bioactive agent.

5. The sensor of claim 1, wherein the membrane is substantially planar.

* * * * *

UNITED STATES PATENT AND TRADEMARK OFFICE
CERTIFICATE OF CORRECTION

PATENT NO. : 9,788,766 B2
APPLICATION NO. : 14/281697
DATED : October 17, 2017
INVENTOR(S) : Peter C. Simpson et al.

It is certified that error appears in the above-identified patent and that said Letters Patent is hereby corrected as shown below:

On the Title Page

In Column 1 (page 4, item (56)) at Line 29, Under Other Publications, change "hypoglycaemic" to --hypoglycemic--.

In Column 1 (page 4, item (56)) at Line 52, Under Other Publications, change "Senso" to --Sensor--.

In Column 1 (page 4, item (56)) at Line 59, Under Other Publications, change "Biologicai" to --Biological--.

In Column 1 (page 4, item (56)) at Line 64, Under Other Publications, change "Therarpeutics" to --Therapeutics--.

In Column 2 (page 4, item (56)) at Line 19, Under Other Publications, change "Surfacts" to --Surfaces--.

In Column 2 (page 4, item (56)) at Lines 41-42, Under Other Publications, change "on on" to --on--.

In Column 1 (page 5, item (56)) at Line 11, Under Other Publications, change "Enzymlology" to --Enzymology--.

In Column 1 (page 5, item (56)) at Line 26, Under Other Publications, change "artifical" to --artificial--.

In Column 1 (page 5, item (56)) at Line 45, Under Other Publications, change "your" to --you--.

In Column 2 (page 5, item (56)) at Line 4, Under Other Publications, change "Hypoglycaemia" to --Hypoglycemia--.

In Column 2 (page 5, item (56)) at Line 57, Under Other Publications, change "C ross" to --Cross--.

Signed and Sealed this
Twenty-seventh Day of February, 2018

Andrei Iancu
*Director of the United States Patent and Trademark Office*

CERTIFICATE OF CORRECTION (continued)
U.S. Pat. No. 9,788,766 B2

In Column 2 (page 5, item (56)) at Line 57, Under Other Publications, change "Contaning" to --Containing--.

In Column 2 (page 5, item (56)) at Line 67, Under Other Publications, change "patents" to --patient--.

In Column 1 (page 6, item (56)) at Line 15, Under Other Publications, change "Eiectrochemical" to --Electrochemical--.

In Column 1 (page 6, item (56)) at Line 16, Under Other Publications, change "E lectrochimica" to --Electrochimica--.

In Column 1 (page 6, item (56)) at Line 54, Under Other Publications, change "Aniodic" to --Anodic--.

In Column 2 (page 6, item (56)) at Line 52, Under Other Publications, change "sub-cutaneous" to --subcutaneous--.

In Column 2 (page 6, item (56)) at Line 71, Under Other Publications, change "Metababolism" to --Metabolism--.

In Column 1 (page 7, item (56)) at Line 3, Under Other Publications, change "G lucose" to --Glucose--.

In Column 1 (page 7, item (56)) at Line 19, Under Other Publications, after "al." insert --2008.--.

In Column 1 (page 7, item (56)) at Line 19, Under Other Publications, change "glocuse" to --glucose--.

In Column 1 (page 7, item (56)) at Line 32, Under Other Publications, change "indepently" to --independently--.

In Column 1 (page 7, item (56)) at Line 39, Under Other Publications, change "valication" to --validation--.

In Column 1 (page 7, item (56)) at Line 40, Under Other Publications, change "iunsulin interaaction in tyhpe" to --insulin interaction in type--.

In Column 1 (page 7, item (56)) at Line 45, Under Other Publications, change "Artifical" to --Artificial--.

In Column 1 (page 7, item (56)) at Line 59, Under Other Publications, change "Electronanalysis" to --Electroanalysis--.

In Column 2 (page 7, item (56)) at Line 12, Under Other Publications, change "el." to --al.--.

CERTIFICATE OF CORRECTION (continued)
U.S. Pat. No. 9,788,766 B2

In Column 2 (page 7, item (56)) at Line 12, Under Other Publications, change "artifical" to --artificial--.

In Column 2 (page 7, item (56)) at Line 24, Under Other Publications, change "amperometeric" to --amperometric--.

In Column 2 (page 7, item (56)) at Line 26, Under Other Publications, change "49:68-72 352:613-614." to --49:68-72.--.

In Column 2 (page 7, item (56)) at Line 47, Under Other Publications, change "glucoseoxidase-based" to --glucose oxidase-based--.

In Column 1 (page 8, item (56)) at Line 4, Under Other Publications, change "giucose" to --glucose--.

In Column 1 (page 8, item (56)) at Line 14, Under Other Publications, change "termistor" to --thermistor--.

In Column 1 (page 8, item (56)) at Line 15, Under Other Publications, change "Biochimca" to --Biochimica--.

In Column 1 (page 8, item (56)) at Line 17, Under Other Publications, change "cholesteral and cholesteral" to --cholesterol and cholesteryl--.

In Column 1 (page 8, item (56)) at Line 71, Under Other Publications, change "Horn Metababolism" to --Horm. Metabolism--.

In Column 2 (page 8, item (56)) at Line 4, Under Other Publications, change "Bromedical" to --Biomedical--.

In Column 2 (page 9, item (56)) at Line 63, Under Other Publications, change "cholesteral" to --cholesterol--.

In Column 1 (page 10, item (56)) at Line 31, Under Other Publications, change "C arbon" to --Carbon--.

In Column 1 (page 10, item (56)) at Line 49, Under Other Publications, change "Tranducers" to --Transducers--.

In Column 2 (page 10, item (56)) at Line 65, Under Other Publications, change "H202" to --$H_2O_2$--.

In Column 2 (page 10, item (56)) at Line 67, Under Other Publications, change "H202" to --$H_2O_2$--.

In Column 1 (page 11, item (56)) at Line 17, Under Other Publications, change "H202" to --$H_2O_2$--.

In Column 1 (page 11, item (56)) at Line 15, Under Other Publications, change "daed" to --dated--.

In the Specification

In Column 12 at Line 30, Change "melenamic" to --mefenamic--.

In Column 12 at Line 34, Change "betamethesone," to --betamethasone,--.

In Column 12 at Line 48, Change "infiximab)," to --infliximab),--.

In Column 12 at Line 50, Change "methothrexate," to --methotrexate,--.

In Column 12 at Line 51, Change "vincristing, mitomycine," to --vincristine, mitomycin,--.

In Column 12 at Line 53, Change "batimstat," to --batimastat,--.

In Column 12 at Line 57, Change "catchins," to --catechins,--.

In Column 12 at Line 58, Change "Tesosentan," to --Tezosentan,--.

In Column 12 at Line 59, Change "Cerivasttin)," to --Cerivastatin),--.

In Column 12 at Line 67, Change "aminoclycosides" to --aminoglycosides--.

In Column 13 at Line 17, Change "sulfanilamidum" to --sulfanilamide--.

In Column 14 at Line 6, Change "Angiotropin," to --Angiotrofin,--.

In Column 14 at Line 10, Change "glenipin," to --genipin,--.

In Column 24 at Line 26, Change "cellosic" to --cellulosic--.

In Column 25 at Line 59, Change "can by" to --can be--.

In Column 30 at Line 59, Change "gentamycin," to --gentamicin,--.

In Column 33 at Line 5, Change "PA," to --1½,--.

In Column 48 at Line 34, Change "phospazenes," to --phosphazenes,--.

In Column 48 at Line 38, Change "hydyoxyethyl" to --hydroxyethyl--.

In Column 54 at Line 5, Change "US-2006-0016700A1." to --US-2006-0016700-A1.--.